US006399321B1

United States Patent
Tessier et al.

(10) Patent No.: US 6,399,321 B1
(45) Date of Patent: Jun. 4, 2002

(54) METHODS FOR SCREENING UDP-GLUCOSE:GLYCOPROTEIN GLUCOSYLTRANSFERASE (UGGT) ACTIVITY AND NUCLEIC ACID ENCODING FOR UGGT

(75) Inventors: Daniel C. Tessier, Pierrefonds; Daniel Dignard, Montréal; John J. M. Bergeron, Pointe Claire; David Y. Thomas, Montréal West, all of (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/376,330

(22) Filed: Aug. 18, 1999

(51) Int. Cl.$^7$ .................................................. C12Q 1/48
(52) U.S. Cl. ..................... 435/15; 435/193; 435/252.3; 435/320.1; 536/23.1; 536/23.2
(58) Field of Search .............................. 536/23.1, 23.2; 435/193, 15, 252.33, 320.1

(56) References Cited

PUBLICATIONS

Trombetta et al. Glucosylation of glycoproteins by mammalian, plant, fungal, and trypanosomatid protozoa microsomal membranes. Biochemistry. Oct. 3, 1989, vol. 28, pp. 8108–8116.*
Sousa et al. Recognition of the oligosaccharide and protein moieties of glycoproteins by the UDP–Glc:glycoprotein glucosyltransferase. Biochemistry. Jan. 14, 1992, vol. 31, pp. 97–105, especially pp. 103–104.*
Camirand et al. Glycoprotein biosynthesis in Saccharomyces cerevisiae, isolation and characterization of the gene encoding a specific processing alpha–mannosidase. The Journal of Biological Chemistry. Aug. 15, 1991, vol. 266, pp. 15120–15127, especially pp.*
Trombetta and Parodi. Purification to apparent homogeneity and partial characterization of ral liver UDP–glucose:glycoprotein glucosyltransferase. The Journal of Biological Chemistry. May 5, 1992, vol. 13, pp. 9236–9240, especially p. 9236.*
Preston, Gregory M. "Cloning gene family members using the polymerase chain reaction with degenerate oligonucleotide primers." In: cDNA Library Protocol. Edited by I.G. Cowell and C. A. Austin. New Jersey: Humana Press Inc., 1997, pp. 97–113.*
Arima, K. et al.(1983) *Nucl. Acids Res.* 11:1657–1672.
Bause, E. et al. (1986) *FEBS Letters* 206:208–212.
Bajwa, W. et al. (1984) *Nucl. Acids Res.* 12:7721–7739.
Bussey, H., et al. (1995) *Proc. Natl. Acad. Sci. U.S.A.* 92:3809–3813.
Camirand, A. et al.(1991) *J. Biol. Chem.* 266:15120–15127.
Casadaban, M. et al. (1980) *J. Mol. Biol.* 138:179–207.
Choudhury, P. et al. (1997) *J. Biol. Chem.* 272:13446–13451.
Cooper, H.M. et al. (1995) in Current Protocols in Immunology, 2nd Ed., (Coligan, J.E. et al. eds), vol. 1, Section 2, John Wiley and Sons, Inc., New York.
Fernández, F. et al. (1996) *EMBO J.* 15:705–713.
Graham, T.R. et al. (1992) *Yeast* 8:S458.
Hammond, C. et al. (1994) *Proc. Natl. Acad. Sci. U.S.A.* 91:913–917.
Hébert, D.N. et al. (1995) *Cell* 81:425–433.
Helenius, A. et al. (1997) *Trends Cell Biol.* 7:193–200.
Herscovics, A. et al. (1993) *FASEB J.* 7:540–550.
Holmes, D.S. et al. (1981) *Anal. Biochem.* 114:193–197.
Hubbard, S.C. et al. (1981) *Annu. Rev. Biochem.* 50:555–584.
Jelinek–Kelly, S. et al. (1988) *J. Biol. Chem.* 263:14757–14763.
Johnston, M., et al. (1994) *Science* 265:2077–2082.
Ou, W. J. et al. (1993) *Nature* 364:771–776.
Nakayama, K. et al.(1992) *EMBO J.* 11:2511–25.
Parlati, F. et al. (1995) *J. Biol. Chem.* 270:244–253.
Parodi, A.J. et al. (1984) *J. Biol. Chem.* 259: 6351–6357.
Parker, C.G. et al. (1995) *EMBO J.* 14:1294–1303.
Peterson, J. R. et al. (1995) *Mol. Biol. Cell* 6:1173–1184.
Rose, M.D. et al. (1990) in Methods in Yeast Genetics : A Laboratory Manual, Cold Spring Harbor Laboratory Press, New York.
Rodan, A. R. et al. (1996) *EMBO J.* 15:6921–6930.
Rudd, P.M. et al. (1994) *Biochemistry* 33:17–22.
Sousa, M. et al. (1995) *EMBO J.* 14:4196–4203.
Sousa, M.C. et al. (1992) *Biochemistry* 31: 97–105.
Tait–Kamradt, A.G. et al.(1986) *Mol. Cell. Biol.* 6:1855–1865.
Tessier, D.C. et al. (1991) *Gene* (Amst.) 98:177–183.
Trombetta, S.E et al. (1989) *Biochemistry* 28:8108–8116.
Trombetta, S.E. and Parodi, A.J. (1992) *J. Biol. Chem.* 267:9236–9240.
Wilson, R. et al. (1994) *Nature* 368:32–38.
Zapun, A. et al. (1997) *Cell* 88:29–38.
Zapun, A., Darby, N.J., Tessier, D.C., Michalak, M., Bergeron, J.J.M., and Thomas, D.Y. (1998) J. Biol. Chem. (in press).

* cited by examiner

*Primary Examiner*—Ponnathapu Achutamurthy
*Assistant Examiner*—Christian L. Fronda
(74) *Attorney, Agent, or Firm*—Swabey Ogilvy Renault; France Côté

(57) ABSTRACT

The present invention relates to a method for determining the effect of a test sample on UGGT activity. The method comprises the steps of: a) exposing an acceptor substrate of UGGT such as acid phosphatase to a labeled donor such as UDP-$^3$H-glucose in the presence of the test sample and UGGT; and b) detecting the amount of donor which was transferred to the acceptor substrate wherein a decrease of donor intake when compared to a control means that the test sample is a UGGT stimulator and a decrease means that the test sample is a UGGT inhibitor. The present invention also relates to an isolated mammalian cDNA which encodes for rat UGGT and to methods of producing mammalian UGGT using recombinant vectors.

7 Claims, 18 Drawing Sheets

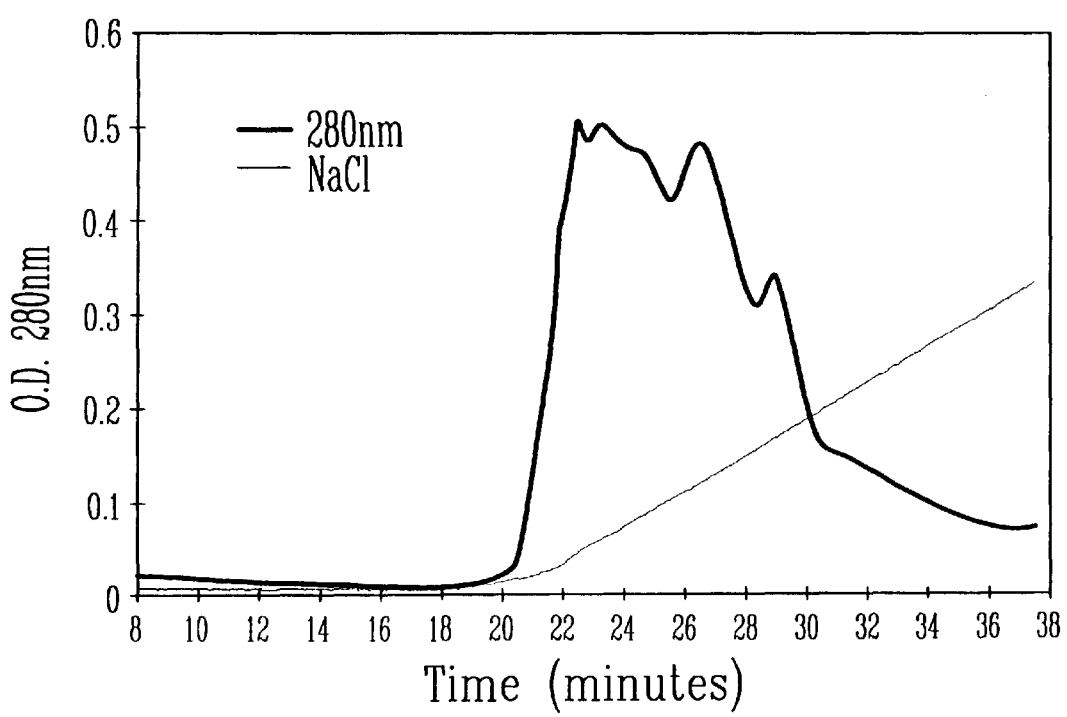

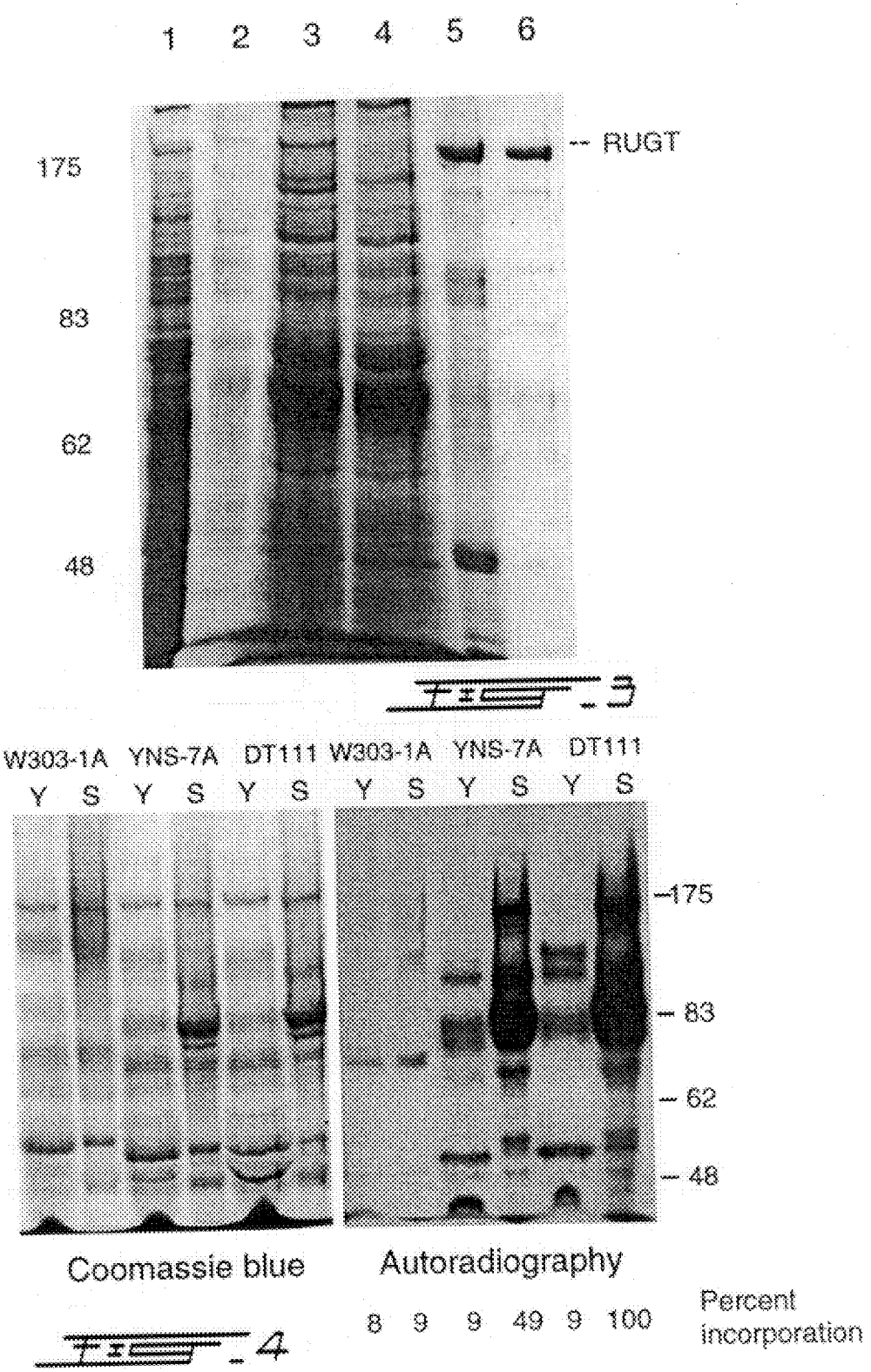

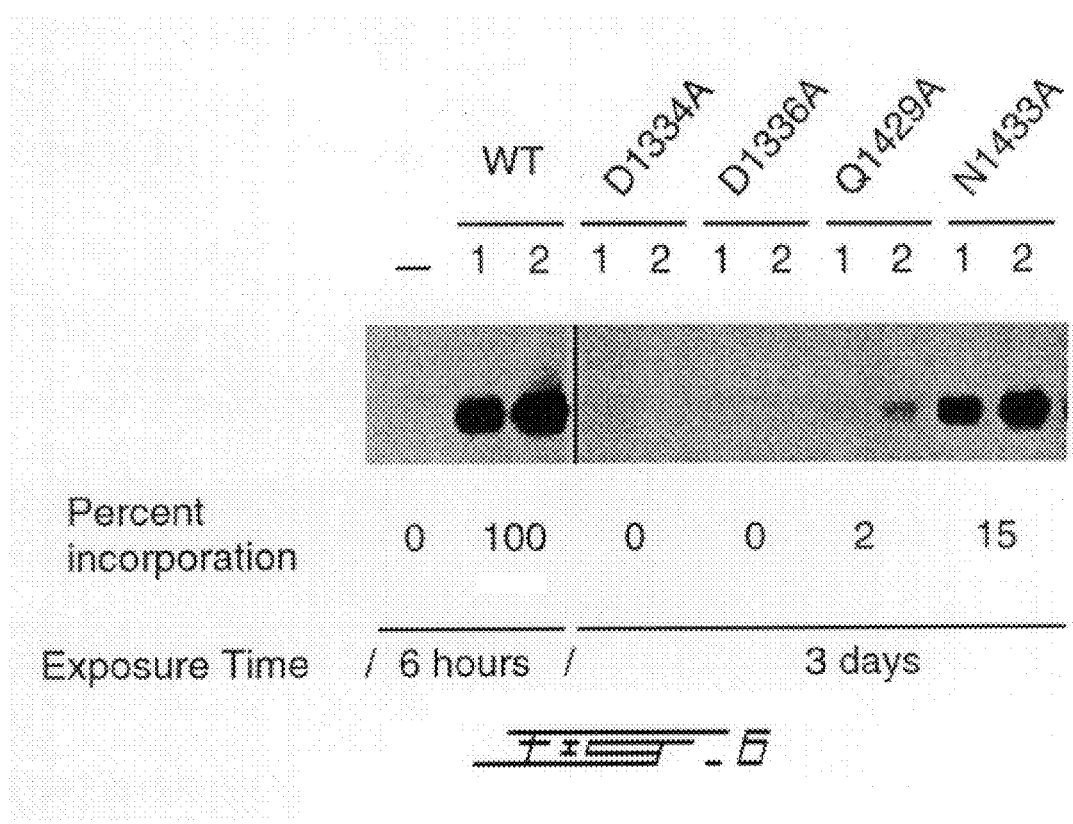

RUGT N-terminal sequence :

```
  M   G   L   L   I   A   L   A   L   L   C   L   F   S   L   A   E   A      (OF SEQ ID NO:2)
ATG GGA CTC CTG ATT GCA CTG GCC TTA CTG TGC CTG TTT TCC TTA GCA GAA GCC    (OF SEQ ID NO:1)
```

Melittin signal peptide sequence :

```
                   M   K   F   L   V   N   V   A   L   V   F   M   V   V   Y   I
CGGTCCGCACAAG  ATG AAA TTC TTA GTC AAC GTT GCA CTA GTT TTT ATG GTC GTG TAC ATT
  Rsr II                                         Spe I
```

```
  S   Y   I   Y   A      4
TCT TAC ATC TAT GCG     3
```

RUGT C-terminal sequence :

```
      Q   E   G   S   Q   K   H   E   E   L  Stop
... CAG GAA GGA TCT CAG AAG CAT GAA GAA TTA TGA
```

C-terminal (His)$_6$ tag :

```
      Q   E   G   S   Q   K   H   H   H   H   H   H StopStop        6
... CAG GAA GGA TCT CAG AAG CAT CAC CAT CAC CAT CAC TGA TAA  GGTACC  5
                                                             KpnI
```

FIG. 8A

Mutant D1334A RUGT :

```
                                1334    1336
       P    L    V    V    D    K    F    L    F    V    A    A    D    Q    I    V    R    T    D    8
... CCG  TTG  GTT  GTT  GAC  AAA  TTC  CTC  TTT  GTG  GCT  GCA  GAT  CAG  ATT  GTG  CGG  ACA  GAT...7
                                                   New PstI
```

Mutant D1336A RUGT :

```
                                1334    1336
       P    L    V    V    D    K    F    L    F    V    D    A    A    Q    I    V    R    T    D    10
... CCG  TTG  GTT  GTT  GAC  AAA  TTC  CTC  TTT  GTG  GAT  GCC  GCT  CAG  ATT  GTG  CGG  ACA  GAT...9
                                                        New BsrBI
```

Mutant Q1429A RUGT :

```
                           1429                1433
       Q    D    P    N    S    L    S    N    L    D    A    D    L    P    N    N    M    I    H    12
... CAG  GAT  CCC  AAC  AGT  CTT  TCA  AAT  CTA  GAT  GCA  GAT  TTG  CCC  AAT  AAC  ATG  ATC  CAT...11
       BamHI                         New XbaI
```

Mutant N1433A RUGT :

```
                           1429                1433
       Q    D    P    N    S    L    S    N    L    D    Q    D    L    P    A    N    M    I    H    14
... CAG  GAT  CCC  AAC  AGT  CTT  TCA  AAT  CTT  GAT  CAA  GAT  TTG  CCG  GCT  AAC  ATG  ATC  CAT ...13
       BamHI                                             New NaeI
```

FIG. 8B

```
              \ R
SEQ ID NO: 2 -Rat      MGLLITALALLCLFSLAEANSKAITTSLTTKWFSAPLLLEASEFLAEDSQEKFMSFVEASQN.IGS.SDQHDTDRSYDAILEAAFR..FLSPLQQNLLKFCLSRSYSASIQ  108
         15-Dm   MLRAVALCVSVVLIALYTPTSGESSQSYPITTLNAKWTQTPLYLEIAEVLADEQAGLFWDYVSGVTK.LDTVLNEYDTESQQYNAALELVKS..HVSSPQLPLLRLVVSMHSLTPRIQ  116
         16-Cel  MALTGLLIFFCHIAVIAALEKKGVHTSLKANWDSTSLLAEASEFIAEENEKLFVKFIDIVNKDVGTLNWEKLTDEQKYEYIKTAGK..VLSTSSVDLLKFAIALRQYSPRVQ  111
         17-Sp         MRWGFWFAIATLITICYAAKPLDVKIAATFNAPSFSALIAESLYQEKKEGFTWYLNHLSDLLDA...ENTTEKELYINVVNSLKREYVLSDEELSSLQFSLGFSGAPKLQ  108
         18-Kre5       MRLLALVLILLCAPLRAWTYSLRYGIPESAQVW...SIIVHL...LGDVDNQL....LTNLYPLVTGLDDEIDIQENLV.ALTSNVLRERYDKEDVADLLEYASIYPMG.MTQ  102
         19-cons                      K ITS  A W   SLL E   E LAE   LF          E DT    Y A      R  LS     LL F LSL  S    P IQ Rat     AFQQIAVDEPPPEG.CKS..FLSVHGK.QTCDLGTLESLL..LTAPDRPKPLL.FKGDHRYPSSNPESPVVIFYS..EIGHEEFSNIHHQLISK.SN.EGKINYVFRHYISNPRKE..    213
Dm      THFQLA.EELRSSGSCQSFTFAQVGSE.LACSFNELQKKLEVPLAKDSLDAPVTYSFDHIFPGSENNTRTVVLG..DLGSSQF.RTYHKLLEKEAN.AGRIRYILRHQLAKKDKR..    227
Cel     SFQQIAVE....YGE.KCDVFVVVGEQ.VSCEYTKLEKMIKDAKT....NSQVL..ESDHIF.GEKDLKQAAILYG..ELGTTSFAKAWEKL.SKLQ....KTKLIFRHFSKKTDSH..    208
Sp      AFSSIVQSR.....TCDCDTWLQLDEESQVC.FSDLPK..DSPLFSKLYSKNPLDYE...VVKTSATGIPYAVVT..SFERDLIP..FHELYYKLAL.EGKCNYVIRYSPPSSSKLNS   211
Kre5    ..HDISSN..AEQDDANSYFVLNGNRYEKPDDVFYLKSKDLTIQQKVPDVDVIQ.PYDVVI.GTNSEAPILLLYGCPTVIDSDEEFNRNLFMEAMNGEGKFRFIWR..........S    205
cons  F QIA         GCS   F  VG        C    LK     L       L      VL  DH  GS    P  ILYG    G   F   HLK N EGK  YI RH
```

FIG. 9A

```
Rat   PVHLSGYGVELAIKSTEYKAKDDTQVKGTEVNTTVIGENDPIDEVQGFLFGKLRELYPSLEGQLKEFRKHLVESTNEMAPLKVWQLQDLSFQTAARIIA.....APVELALVVMKDISQ 327
Dm    PVRLSGYGVELHLKSTEYKSQDDAPKPEA.GSTSEDLANES.DVQGFDFKVLKQKHPTLKRALDLRQRLLQGNDEIAQLKAWEFQDLGLQAAAAIAE.....IQGDETIQILQYTAH 339
Cel   PVSLSGYGVELAIKNTEYKAVDESSEKKNV...EEDEAD....LFGFNIKLLKELHPDSVDAIESFRVNLKES.DELTPLKRWELQDLSYQAAQKIVN.....AGPADAIGTLEEYSQ 313
Sp    KLYVKGFGTHVSLKRTDYLVVDREFPREKGDNPASFTSSRNKRSNERLFGMTSDSLQTVTP..........DKIAIL.....DL..LATQSIAS.....S..ADMLSAFRELTQ 302
Kre5  TCSLDG......KSVEYPLTHPLEITLQNGSRMSS..............IPQLKKILYTVPKEILVG.....ADNDDQLHDLEPEELRELDRVTSLISEFYQKKDITATLNFTKSIVN 300
cons  PV LSGYGVEL KSTEYK  DD       G               GF F  LK L P L   L  R L   DE A LK WELQDL QAA  I        L         Q Rat   NFPTKARAI.TKTAVSAQLRAEVEENQKYFKGTIGLQPGDSALFINGLHIDLDTQDIFSLFDTLRNEARVMEGLHRLGIEGLSLHNIIK.LNIQPSEDYAVDIRSP............ 432
Dm    NFPMLARTL.LAHKVTDGLRAEVKHNTEAFGRSLNVAPPDGALFINGLFFDADTMDLYSLIETLRSEMRVLESLHSNNVRGSLASSLLALDLTASSKKEFAIDIRDT........... 445
Cel   NFPTHARAL.AKTSVSDLLRKEVLQNRKMLEKA.SIEVGETSLYINGINQDINSLDFKLADLFKDGFHSMGINREYLSILVGMDTSDDEKTYAVDHREG.............. 418
Sp    DFPIYAHYLSIQPDVSNHLIEELNQFQSQY......VPEGINTIWLNGLSIDLEETDAFSILSLIKKEKDMFDRFEALGIKSSKVLDIVTNEAFANEDSDFKFVKFHCQDDIEDWK.... 412
Kre5  NFPLISKQLIKVSSVNKDI..ITSNEEL..NSKGFDYNMLGLYINCQNWKITSLTPYNLLTALKTEYQSLLKITNLLQELEPSKCILDSKFLLNKFSQFSLGKLQNLQPIKMDLHTIP 414
cons  NFP  AR L        VS LR EV N            G   L INGL   D    D FSL  LK E           H LGI          IL              FA D R            DIR
```

FIG. 9B

```
Rat    ....AISWNNLEVDSRYNSWPSSLQELLRPTFPGVIRQIRKNLHNMVFIVDPVHETTAELVSIAEMFLSNHIPLRIGFIFVNDSEDVDGMQDAGVAVLRAYNYVGQEVDGYHAFQTL   547
Dm     ....AVQWNDIENDVQYRRWPSSVMDLLRPTFPGMLRNIRKNVFNLVLVVDALQPTARSVIKLSESFVIHQAPIRLGLVFDARDANE.DNLADY.VAITCAYNYVSQKKDARAALSFL   558
Cel    ....YPFFINNLDTDKKYKQWGNSVKLMLQPYYPGMIRPIARNLFSLVFVVDPSTSEGRKFLRIGQTFNSHDIAMRIGYIFAVNQDTKASGETDLGVALINLFNFVSIDSSNADALKVL   533
Sp     ....AIHWNEIESNPKYDNWPKSIQILLKPIYPGQLHMLGKQLHTVIYPIFPSSPSSLPLLSELIQFSRRPSPVQTGMVCAANDDE......FAQTVCKSFFYISKESGTDSALKFL   521
Kre5   GFSESVIIFNDIESDPQYDELVNSVQAFFDKSKFGELPEIKQNWSEIIFVID.......FARLEDSEVKEALG...GLVRAVNVVSQGYPQR...VGLL.PF...SSDSDK....SVV   511
cons        A    WYN IE D  Y  WP SVQ LL P  PG LR I KNL  VFVVDP         F     P R G VFAVND      D  VA L  FNVS  SD   AL  L Rat    TQIYNKVRTGEKVKVEHVVSVLE.KKY...PYVEVNSILGIDSAYDQNRKEARGYYEQTGVG..PLPVVLFNGMPFEKEQLDPD.ELETITMHKILETTFFQRAVLGELSHDQDV.V   658
Dm     TDIYAAVGETKVVTKKDIVKQLT.KEFTSLSFAKAEEFLEEDSTYDYGRELAAEFIQRLGFGDKEQPQALLNGVPMPSNVVTADSDFEEAIFTEIMHTSNLQKAVVKGELT.DNDVAI   675
Cel    NNFLDDYR.SKDPTIEDIKEFFE.AKFSDASF...SDVFGVNSDYDKGRKHGFEFVQKTGLNSA..PKVLLNGFILDDEGVRGD.NIEETIMEVMKISPKIQRAIMEGKLTDRMNVG.   643
Sp     YKCLNSDSSADIYSL..LEEHLPLSEHDDTLANLKKDLS.SSFFDHYMSKSNSWVNRLGI.DSSASEVIVNG.....RIISHDENYDRSMYGIFLEDIPEVQIAVAEGKISEDDNL.L   630
Kre5   NKIYELKNSTD..NLTELKSFLETMLLADGLSANAKHSKHIPVP.D......VFHLLDELQIDETS...IIINGEIYPFR.....KWNYLIAKVIKKDTEFIRKELSNSS.PKNKQISV   613
cons      IY      IE    D  A   L  S YD  R           LG       PVL NG           DNE I I T    Q AV  GL D V
```

FIG. 9C

```
Rat    EYIMQPNVVPRINSRIL.TAKR.E.YLDL..TASNNFTVDDFARFSALDSRGKTAAIANSMNYLIKKGMSSKEIYDDSFIRPVTFWIVGDFDSPSGRQLLYDAIKHQKTSNNVRISMI    772
Dm     DYLMNQPHVMPRLNQRIL.SQEDVK.YLDINGVAYKN..LGNVGVLNRLSNRDMTATLMDNLKYF..GGKKSTELIGRTSLQFLTIWVFADLFTDQGRDLLTHALDYVQSGESVRVAFI    788
Cel    NWVLEQKDVMPRINKRIL.SAPSKKTVEILG.SMDCKSLKDV...ENLSDSDKAGCLLQTTKYLQKASADS........ILPVTLWVADAEAASGRFTYNSLQILKNSANSRVGII         749
Sp     DFILRDAS.LTR.NPLVYPSAKSSIKSIDIKRV......LENVG...SLNHEDILLIGSSNAKY..........................SFWLVADFNEKEGLEILSLLADLLSENKDANLMLI   718
Kre5   RDLLHYKSANLRHNK..........V........TPNYFADSV..YSSVNNTALESVCSERIGYYTKN..EEYNLLH.......TITLVDDFFGSIHALKRLRNLLH..TSFVGVRIRII    701
cons        L Q  V PR N RIL SA    Y DI     N L V    D     KY K    S                    TW VADF   GR L  L          VR        I Rat    NNPSR.EISDSSTPVSRAIWAALQTQTSNSAKNFITKMVKEE.TAEALAAGVDIGEFSVGGMD....VSLFKEVFESSRMDFILSHALYCRDVLKLKKGQRVISNGRIIGPLEDSELF    895
Dm     PNTES.SSASSRRNLNRLVWAAMQSLPPTQATEQVLKKPKEKIE.........................IPTQLEDILGSTELHLKMLRVYSQRVLGLNKSQRLVIGNGRLYGPLSSDESF    886
Cel    FNPESVEKACESNSISSYIRAALDFLPMDQAKRLIIKLSNEEYAADFISGKITFDDLSVGGMDTAKF...LADKKKLDCERTRLESQIV.KKVLDISSGGRVVGNALQVGPLESSEHF    864
Sp     .......QEGKNHVVPPLFAKLLSSPKRSSKHL........QEILNSSLDPSSGVNDMDKALK...FLKKSKAVVKELGLTGE..CKSALIL......NGRMICSF.SVDSL          804
Kre5   ...HVGDISD....IWVQLRGSLSQKDPIGSINTFIDALKLKKVKSHTYKKSGLNQL...GLHKWLPDIPLFELQK..GSFTALNGRFI..ILIKMKCQKQNISKAKII...KREAL    801
cons            AAL    P  AK KK  E        VGGMD L        K         L         VL L K QR VI NGR  IGPL S E  F

FIG. 9D
```

```
Rat    NQDDFHLLENIILKTSGQKIKSHIQQLR..VEE...DVASDLVMKVDALLSAQP......KGEARIEYQFFEDKHSA..IKLKPKEGE.TYYDVVAVDPVTREAQRLAPLLIVLAQLI    990
Dm     DSADFALLARFSSLQYSDKVRQVLKESAQDVNE....EFNSDTLLKLYASLLPRQT.....KTRFKLPTDLKTD.HSV..VKLPPKQEKLPHFDVAAVLDPASRAAQKLTPILLILPQVL    994
Cel    EAADFKLLESMLLSRGAEVISSHLKKWEFDVSN...GVGSNTVFSIAGHVCKHA......SSQKRTWSIQQDEHSV..VTLPADEMDRPAVDVLAVVDPLTMEAQKLGSILHLIKKVT    972
Sp     NTADLKMLMQMEYDNYLSKLKLNIAGSSRRLKNSRAISFLSSYLKTLESTPMSTSSPT...KEEKLFPRDFIYNKLGVGNAFETDDFSKAYYQFVAVLDPLSKDSQKWSAILEAVSKLN    920
Kre5   RTIDSVFALDLLFPGFSQEI..........INPDLIEMISSILTRLFYQGTHIYNNGIDYTESSLPRMDLSEFFRPNNLTM.FEDGKSASIDLLLILDPLEERTQMILSLVEQFRPLK    909
cons       ADF LL          KI        VN      S   L                                    KE  P       D HSV     TL    DV AVLDPL       AQKL IL     L x   x   x              xx
Rat    NMSLRVFMNCQSKLSDMPLKSFYRYVLEPEISFTADNSFAKGPIAKFLDMPQSPLFTLNLNTPESWMVESVRTPYDLDNIYLE.....EVDSIVAAFYELEYLILLEGHCYDITTGQPPR   1104
Dm     NCQLNLYLIPVPQHSDMPVKNFYRYVVEPEVQFEANGGRSDGPLAKFSGLPANPLLTQQLQVPENWLVEAVRAVVDLNIKLT......DIGGPVHSEFDLEYLILEGHCFDAASGAPPR   1108
Cel    NCEIKIVMNPKDKHSELPLKRFYRYAAASELSFDHNGNLNTN.VVRFDNLPSKQLLTLSLQAPDSWIVEAVSAKYDLDNIKME.....QANGDVTAEFFALQHLLLDGQCFDEVSGQPPR   1085
Sp     GVGVRIHLNPKQTISELPLTRFYRYSISAEPFDALGHLERSYV.EFDNLPADTLLTMDIEARDAWTWMQKDVDIDLFNIKLEHTSEAEALDSHTAIYELKNILVQGYSQEEFRKSPPR   1038
Kre5   FVNIQVILMPTLELNIVPIRRIY...VD.....DAD..IVKSITSE..DSRDDPEVDIEMDVPNSFIVDN...NVRIKKLLIELHS..........FSSKTVLSTGN....IDGM..G    996
cons   N    LNP  LS  PLKRFYRY    E   FDA G           F   LP PLLT  L  P SW VE V      YDLDNIKLE            V AEF  L    LLL G C D    G PPR
```

FIG. 9E

```
Rat   GLQFTLGTSANPTTVD.TIVMANLGYFQL...KANPGAWILRLRLRKGRSDDIYRIYSH.DGTDSPPD.A..NDVVILNFKSKIIKVKVQKKADMANEDLLSDGTNEN..ESGFWDSFK 1213
Dm    GLQIVIGTQSQPTLVD.TIVMANLGYFQL...KANPGAWSLRLREGKSADIYAI.SHIEGTNTHHS.AGSSEVQVLITSLRSHVVKLRVSKKPGMQQAELLSD.DNEQAAQSGMWNSIA 1220
Cel   GLQFTLGTDKNPKQFD.TIVMANLGYFQL...KANPGAWKLEIRDGKSSEIYKIGSHV.GAE...K.IGEDVLQWVIDSFTGKSVRVRVEKREGMEERNLLSDD......EEGVWSSLS 1189
Sp    GMQLKIGNLTNSHVTD.TIVLSNLGYFQL...KANPGVWTLEPMDGRSSQFYEILS.LNKKNSYKD.P....QVIVDSFEGVTLNPVMRRKPGFESADIMDEDLSSHKFEDKIKKSLS 1146
Kre5  GVCLAL.VDSAGNIIDKTTMKTFGYGQFHTDKFLKGCY.IKSCDSR....YTVQSF..STDGHPDFIPSDSLDIL..SYNPQKIAVKISEEP.........THEEEYEEG...... 1088
cons  GLQL  LGT  NP  D TIVMANLGYFQL    KANPGAW  L  RDGRS   IY I SH GT   D       QV   SF       V V KKPGM       LLSD   E    E G W S
                                      ————x—K————————————                                                                    ¤

Rat   WGFSGQKTEEVKQDKD.DIINIFSV.ASG.HLYERFLRIMMLSVLKN..TKTPVKFWFLKN.YLSPTFKEFLPYMAKKYNFQYELV..QYKWPRWLHQQ..TEKQRIIWGYKILFLDVL 1322
Dm    SSFGGGSANQAASDEDTETINIFSV.ASG.HLYERLLRIMMVSLLKH..TKSPVKFWFLKN.YLSPQFTDFLPHMASEYNFQYELV..QYKWPRWLHQQ..TEKQRTIWGYKILFLDVL 1330
Cel   NLVS.......SKEKTQEVINVFSL.ASG.HLYERFMRIMIVSVMKN..TKHPVKFWLLKN.YLSPQFKETLPTLAKHYGEYELI..EKWPRWLHQQ..KEKQRIMWGFKILFLDVL 1292
Sp    ..FFNEKREAS.......INIFSV.ASG.HLYERFLYIMTKSVIEH.TDKKVKFWFIEN.FLSPCFKSSIPAIAKKYNFEYEYI..TYNWPHWLRKQ..EEKQREIWGYKILFLDVL 1247
Kre5  ........RNNDT.IINIFTILESGPDEEERYMQ.MILSILSKCPETQKVNFFILDQPFISDTLRKSCEYINSSDEMRGNVIFLNVEWPQWLRPQRFSSRRRDV..SRFLFLDVL 1191
cons             F         D   INIFSV ASG HLYERFLRIM  SVLK    TK PVKFWFLKN  SVLK    P   AK YNF YELI    YKWPRWLHQQ    EKQR IWGYKILFLDVL
                                                                x          x                 ·_
```

FIG. 9F

```
                      xx  x
Rat     FPLWDKFLFVDADQIVRTDLKELRDFN.LDGAPYGYTPFCDSRREMDGYRFWKSGYWASHLAGRK...YHISALYVVDLKFFRKIAAGDRLRGQYQGLSQDPNSLSNLDQDLPNNMIH  1437
Dm      FPLNVRKIIFVDADAIVRTDIKELYDMD.IGGAPYAYTPFCDSRKEMEGFRFWKQGYWRSHLMGRR...YHISALYVVDLKRFRKIAAGDRLRGQYQALSQDPNSLSNLDQDLPNNMIH  1445
Cel     FPLDVQKVIFVDADQVVRADIMELMKED.IGNAPYGVPFCESRKEMDGFRFWKQGYWANHLAGRR...YHISALYVIDLQKFRQIAAGDRLRGQYQGLSGDPNSLANLDQDLPNNMIH  1407
Sp      FPLELHKVIYVDA.QIVRADIQELMDMD.LHGAPYGTPMCDSREEMEGFRFWKGYWKKFLRGLK...YHISALYVVDLDRFRKMGAGDLLRRQYQLLSADPNSLSNLDQDLPNHLQH  1361
Kre5    LPQNISKVLYMSPTE.VPLDPFDIFQGLKRAPIGLF.....RMSGDGY..WKEGYWEKMLRENNLEFYSTEPAFLVNLERFRELDAGDKYRIHYQRISTDAMSLVNIGQDLVNNLQL  1302
cons    FPL V KVIFVDADQIVR DL EL DFD L GAPYGYTPFCDSR EMDGFRFWK GYW   HL GR     YHISALYVVDL RFRKIAAGDRLRGQYQ LS DPNSLSNLDQDLPNNMIH Rat     QVPIKSLPQEW...LWCETWCDDASKRAKTIDLCNNPMTKEPKLEAAVRIVPEWQDYDQEIKQLQTLFQEEKELGTLHEETQEGS............QKHEEL          1527
Dm      QVAIKSLPDDW...LWCQTWCSDSNFKTAKVIDLCNNPQTKEAKLTAAQRIVPEWKDYDAELKTIMSRIEDHENSHSRDSAVDDSVDDSVEVTVTPSHEPKHGEL        1548
Cel     QVKIKSLPQEW...LWCETWCDDGSKKNAKTIDLCNNPLTKEPKLDSAARIIGEWKTYDDEIREVIS....GHSSDNPSDNVISEND............DSHTEL        1493
Sp      LIPIYSLPQDW...LWCETWCSDESLKTAKTIDLCQNPLTKEKKLDRARRQVSEWTSYDNEIASVL....QTASSQSDKEFEEKDNN............SSPDEL        1447
Kre5    EVPIRFLKGSYKKKLVINDECVSEWKK..KINKFASSPGDEDVPGES...VSSKYQDSDN.AA..........................................PLHDEL  1365
cons    QVPIKSLPQ W   LWCETWC  D SKK AKTIDLCNNP TKE KL  A  RIV  EW DYD EI L                                          H EL
```

FIG. 9G

```
UGGT-rat   : PLVVDKFLFVDADQIVRTDIKEIRDFNID-GAPYGYTPFCDSRREMDGYRFWKSGYWASHL---- OF SEQ ID NO 2
UGGT-H.sap: PLAVDKIIFVDADAIVRTDIKEIRDFDLD-GAPYGYTPFCDSRREMDGYRFWKTGYWASHL---- OF SEQ ID NO 15
UGGT-D.mel: PLNVRKLIFVDADAIVRTDIKELYDMDLG-GAPYAYTPFCDSRKEMEGFRFWKQGYWRSHL---- OF 16
UGGT-C.ele: PLDVQKVIFVDADQVVRADIMEIMKFDLG-NAPYGYVPFCESRKEMDGFRFWKQGYWANHL---- OF 17
UGGT-S.pom: PLELHKVIYVDA-QIVRADIQEIMDMDLH-GAPYGYTPMCDSREEMEGFRFWKKGYWKKFL---- 21
UGGT-A.tha: PLSLEKVIFVDADQIIRXDMGELYDMDIK-GRPLAYTPFCDNNRXMDYKFWKQGFWKEHL---- 22
UGGT-O.sat: PLSLRKVIFVDADQIVRADMGELYDMNIK-GRPLAYTPFCDNNKEMDGYRFWKQGFWKDHL----
GALT-E.col: INKAPKVIYLDADIICQGTIEPLINFSFPDDKVAMVV-------TEGQADWW-EKRAHSLGVA 23
GALT-S.typ: QIKQIKVIYLDADIACKGSIQELIDLNFAENEIAAVV-------AEGELEWW-TNARLSLATP 24
GLUT-E.col: GITLDRLIYLDADVVCKGDISQILHLGIN-GAVAAVVKDV-------EPMQEKAVSRLSDP 25
GLUT-S.typ: SKKVNTLIYLDADVVCKGSIADILQIDIT-EKIAAVVKDV-------DSIQNKVNERLSAF 26
IKNIEKAIYIDVDTLTNSSIQEIWNIDITNYYLAACR-------DTFIDVKNEAYKKTIGLE 27
GLYT-N.gon: IADCDKVIYLDTDVIVRDGIKPIWDTDIGGNWVGACI-------DLFVEROEGYKQKIGMAD 28
GSPA-B.sub: DESIKRMIYIDCDAIVLEDISKIWDIDIAPYTVAAVE-------DAGQHERLKEMNVTD--- 29
Q48480-K.p: FRRYDKVVFIDSDTVWKADIGELLDVPLGNNLVAAV-KDIVMEGFVKFSAMSASDDGVMPAGEY 30
GLYC-H.sap: LTQYSKCVEMDADTIVLANIDDLFREELSAAPDPGWPDC------ 31
GLYC-O.cun: LTQYSKCVEMDADTIVLANIDDLFEREELSAAPDPGWPDC------ 32
GLYC-C.ele: LTQYTKCVFLDADTIVLRNADELFTRPDFSAASDIGWPDS------ 33
WSIP-O.sat: FVEYERMVYLDADIQVFDNIDHLFDLKGAFYAVKDCFCEKTWSHTPQYDIGYCQQRPDEVAWP 34
Q12096-S.c: QTEFDRVIYLDNDAIIRSSIDELFFLPN-----------------YIKFAAPLTYWF--ISNS 35
```

```
UGGT-rat    :    ------------AGRKYHISALYVVDLKKFRKIAAGDRLRGQYQGLSQDPNSLSNLDQDLPNMIHQ
UGGT-H.sap  :    ------------LRRKYHISALYVVDLKKFRRIGAGDRLRGQYQALSQDPNSLSNLDQDLPNMIHQ
UGGT-D.mel  :    ------------MGRRYHISALYVVDLKKFRFRKIAAGDRLRGQYQALSQDPNSLSNLDQDLPNMIHQ
UGGT-C.ele  :    ------------AGRRYHISALYVIDLQKFRQIAAGDRLRGQYQGLSGDPNSLANLDQDLPNMIHQ
UGGT-S.pom  :    ------------RGLKYHISALYVVDLDRFRKMGAGDLLRRQYQLLSADPNSLSNLDQDLPNHLQHL
UGGT-A.tha  :    ------------RGRPYHIQCSIRC~~~~~~~~~~~~~~~~~~~~~~~~~~~~~~~~~~~~~~~~
UGGT-O.sat  :    ------------RGRPYHISALYVVDLAKFRQTASGDTLRVFYETLSKDPNSLSNLDQDLPNYAQHT
GALT-E.col  :    ------------GIAKGYFNSGFLLINTAQWAAAQQVSARAIAMINE-PEIIKKITHPDQDVLMLLAD
GALT-S.typ  :    ------------GLVSGYFNAGFILIXIPLWTAENISKKAIEMLKD-PEVVQRITHLDQDVLNIFLVN
GLUT-E.col  :    ------------ELLGQYFNSGVVYIDLKKWADAKLTEKALSIIMS---KDNVYKYPDQDVMNVLLKG
GLUT-S.typ  :    ------------NLQGGYFNSGVVFVNLKIWKENALTKKAFLILAG---KEADSFKYPDQDVLNILQD
GLUT-H.inf  :    ------------GYSYFNAGILLINLNKKEENIFQKSINWMNKY----NNVMKYQDDILNGICKG
GLYT-N.gon  :    ------------GEYYFNAGVLLINLKKWRRHDIFKMSCEWVEQY---KDVMQYQDDILNGLFKG
GSPA-B.sub  :    ------------TGKYFNSGIMIIDFESWRKQNITEKVINFINE-HPDEDELVLHDQDALNAILYD
Q48480-K.p  :    LQKTLNNNPDEYFQAGIIVFNVKQMVEENTFAELMRVLK------AKKYWFLDQDIMNKVFYS
GLYC-H.sap  :    ------------FNSGVFVYQ--------------PSVETYNQLLHIASEQGSFDGGDQGLLNTFSS
GLYC-O.cun  :    ------------FNSGVFVYQ--------------PSVETYNQLLHVASEQGSFDGGDQGLLNTFFNS
GLYC-C.ele  :    ------------FNSGVFVYV--------------PNNETYRQLVDFAVTHGSYDGGDQGLLNDFFSN
WSIP-O.sat  :    ---ERELGPPPLYFNAGMFVHE--------------PGLGTAKDLLDALVTPTPFAEQDFLNMFFRE
Q12096-S.c  :    ----------DLEKSYHETRHREKQ------------PINLQSYTKVLTKRIGKGMIYNHLPSL
```

METHODS FOR SCREENING UDP-GLUCOSE:GLYCOPROTEIN GLUCOSYLTRANSFERASE (UGGT) ACTIVITY AND NUCLEIC ACID ENCODING FOR UGGT

BACKGROUND OF THE INVENTION (a) Field of the Invention

The present invention relates to methods for detecting the effect of test samples on UDP-glucose:glycoprotein glucosyltransferase (UGGT) activity. The present invention also relates to the nucleic acid encoding for mammalian UGGT and to recombinant mammalian UGGT.

(b) Description of the Prior Art

The quality control system of the endoplasmic reticulum (ER) ensures that only folded proteins proceed further along the secretory pathway. Some of the abundant ER proteins are components of molecular chaperone systems which bind to unfolded proteins, retaining them in the ER. The folding enzymes are also abundant in the ER and comprise several disulfide isomerases and prolyl peptidyl isomerases (1, 2). How chaperones and folding enzymes interact to facilitate protein folding in the ER is not known.

Calnexin and calreticulin participate in a molecular chaperone system which integrates the processes of N-glycosylation and quality control (3, 4). They both are lectins that bind N-glycans of the form GlcNAc2Man9Glc1 which result from the removal of the two outer glucoses from GlcNAc2Man9Glc3 oligosaccharides by the sequential action of glucosidases I and II. Removal of the last glucose by glucosidase II prevents binding by calnexin and calreticulin. Then, if the glycoprotein is unfolded, a glucose residue is added back to the high mannose core by the enzyme UDP-glucose:glycoprotein glucosyltransferase (UGGT) which recognizes unfolded proteins (5). Consequently, during folding glycoproteins undergo cycles of binding and release from calnexin and calreticulin which are driven by the addition and removal of a glucose residue (4). As a result of the specificity of UGGT, only unfolded glycoproteins bind to calnexin and calreticulin in vivo (6, 7), even though these lectins do not recognize the conformation of their protein substrates (8, 9).

Monoglucosylated glycoproteins, in addition to binding to calnexin and calreticulin, can also be cross-linked to the ER protein ERp57 (10, 11) (also known as ER-60, ERp60, ERp61, GRP58, P58, HIP-70 or Q-2; ref. (11) and refs therein). ERp57 is homologous to protein disulfide isomerase (PDI) and has been shown to exhibit thiol-disulfide oxidoreductase activity in vitro (12).

UDP-glucose glycoprotein:glucosyltransferase (UGGT) is a soluble enzyme of the endoplasmic reticulum (ER) which catalyzes the addition of a glucose residue onto asparagine-linked oligosaccharides of the form [GlcNAc]2-(Man)7–9 which are present on incorrectly folded glycoproteins (Parodi, 1984; Trombetta, 1989; Sousa, 1992). UGGT is now thought to be responsible for the prolonged binding of unfolded glycoproteins to the ER lectins calnexin and calreticulin (Ou, 1993; Peterson, 1995), and is therefore a key component of the quality control system of the ER which ensures that only correctly folded and assembled protein are exported.

N-linked glycans are synthesized as a dolichol-anchored unit of 14 residues [GlcNAc]2-(Man)9-(Glc)3 (Herscovics, 1993). After transfer of the oligosaccharide to a protein in the ER, the terminal glucose is removed by glucosidase I (Bause, 1986). Then, glucosidase II successively removes the two remaining glucose residues (Hubbard, 1981) leaving the [GlcNAc]2-(Man)9 core oligosaccharide. If the glycoprotein is not correctly folded, the innermost glucose is added back by UGGT, which can discriminate between folded and unfolded substrates (Trombetta, 1989; Sousa, 1995). The known specificity of UGGT for unfolded proteins and the in vivo abrogation of binding to calnexin by inhibitors of the two glucosidases led to the formulation of a model whereby only monoglucosylated glycoproteins bind to calnexin or calreticulin (Hammond, 1994; Helenius, 1997). Unfolded glycoproteins are thought to undergo cycles of binding to and release from calnexin and calreticulin. Glucosidase II does not recognize the conformation of the polypeptide but removes indiscriminately the glucose which is present (Rodan, 1996). If the glycoprotein is folded, it is not reglucosylated by UGGT and escapes from the cycle. If the glycoprotein is still unfolded, it is reglucosylated and remains trapped in the cycle (Hébert, 1995). The ensemble of UGGT, glucosidase II, calnexin and calreticulin can be considered as a molecular chaperone system as their interplay results in the binding and release of unfolded proteins. The binding of unfolded glycoproteins to calnexin and calreticulin relies on the specificity of UGGT for unfolded substrates, as both lectins were shown not to recognize the conformation of their substrates (Rodan, 1996; Zapun, 1997).

UGGT has been previously purified to homogeneity from rat liver and shown to have an apparent molecular weight of about 150 kDa on denaturing gels and 270 kDa in native conditions (Trombetta, 1992). This enzyme catalyzes the transfer of the glucose residue from UDP-glucose onto the distal mannose residue of the longest branch of the core oligosaccharide in an α-1,3 linkage (Trombetta, 1989). [GlcNAc]2-(Man)9 was found to be a better acceptor for the glucose transfer than [GlcNAc]2-(Man)8, which in turn is better than [GlcNAc]2-(Man)7 (Sousa, 1992). Oligosaccharides with a lower mannose content are not substrates of UGGT. Most importantly, the glucosylation reaction is far more efficient if the glycoprotein substrate is unfolded. The effect of denaturation is not to expose the oligosaccharides but to make protein determinants required for enzymatic activity accessible to UGGT (Sousa, 1992). The enzyme was also shown to have some affinity for hydrophobic peptides (Sousa, 1995) and unfolded proteins are known to expose hydrophobic residues that are normally buried in the folded conformation. Unfolded glycoproteins treated with endo-β-N-acetylglucosaminidase H (EndoH) were found to be competitive inhibitors of the reaction whereas denatured non-glycosylated proteins were not. This finding indicated that the innermost N-acetylglucosamine residue, which remains attached to the denatured polypeptide after treatment with EndoH, is presumably required for substrate recognition (Sousa, 1992).

The cDNA encoding UGGT from Drosophila melanogaster has been cloned (Parker, 1995; Accession #U20554) as well as from the fission yeast *Schizosaccharomyces pombe*, GPT1 (Fernández, 1996; Accession # U38417). The sequence of the gene encoding UGGT from *Ceanorabditis elegans* is also available as a result of the genome sequencing project of this organism (Wilson, 1994; Accession #U28735). These genes all encode proteins of about 1500 amino acids with a N-terminal signal sequence and a C-terminal retention signal, as expected for ER luminal proteins. The gene for UGGT is not essential in *S. pombe* and no apparent phenotype can be observed upon its disruption (Fernández, 1996).

One of the major hurdle in the study of UGGT is the scarcity of appropriate substrates for detailed in vitro studies. High mannose oligosaccharides are transient species in the cell as they are further modified along the secretory pathway following their exit from the ER. Most secreted glycoproteins do not contain the [GlcNAc]2-(Man)7-9 acceptor glycans and when they do, the appropriate oligosaccharides constitute only a small fraction of the total, as it is the case for bovine pancreatic ribonuclease B (RNase B) (Rudd, 1994; Zapun, 1997). As the pathways of oligosaccharide biosynthesis in *Saccharomyces cerevisiae* are well characterized, this organism provides a mean to produce various forms of glycans by genetic engineering.

In yeast, the transfer of N-linked oligosaccharides onto proteins is analogous to that in mammals. However, after glucose trimming, the remaining [GlcNAc]2-(Man)9 core oligosaccharide is modified differently (Herscovics, 1993). One of the terminal mannose residues is removed by the action of an ER α-mannosidase, product of the gene MNS1 (Jelinek-Kelly, 1988). The remaining terminal mannose units are the acceptors for the addition of further mannose residues by an α-1,3-mannosyltransferase encoded by the gene MNN1 (Graham, 1992). Finally, one of the GlcNAc residue is also the site of attachement of an additional mannose residue by an α-1,6-mannosyltransferase encoded by the OCH1 gene (Nakayama, 1992). A long polysaccharide chain is then built onto this additional mannose residue to produce the typically hyperglycosylated yeast proteins. A yeast strain having these three genes disrupted is expected to produce glycoproteins which have only [GlcNAc]2-(Man)9 oligosaccharides.

SUMMARY OF THE INVENTION

It is an aim of the present invention to provide a method for determining UGGT activity.

It is also an aim of the present invention to provide an isolated nucleic acid comprising a nucleotide sequence encoding for a mammalian UGGT.

It is also an aim of the present invention to provide a recombinant mammalian UGGT.

In accordance with the present invention there is provided a method for determining the effect of a test sample on UGGT activity which comprises the steps of:
a) exposing a UGGT substrate to a labeled donor in the presence of the test sample and UGGT; and
b) detecting the amount of labeled donor which was transferred to the UGGT substrate wherein an increase of donor intake when compared to a control means that the test sample is a UGGT stimulator and a decrease means that the test sample is a UGGT inhibitor.

In accordance with the present invention, there is provided an isolated nucleic acid comprising a nucleotide sequence or an analogue thereof provided that the nucleotide sequence or an analogue thereof encodes for mammalian UGGT.

BRIEF DESCRIPTION OF THE DRAWINGS

FIG. 3 represents an SDS-PAGE stained with Coomassie blue showing samples of crude and purified RUGT (1) Total cell extract, (2) Supernatant culture medium, (3) Concentrated/diafiltrated culture medium; column load and (4) flow through fraction from the Ni++−NTA column, (5) Ni++−NTA-purified RUGT, (6) POROS 20HQ-purified RUGT. (M) Molecular weight standards.

FIG. 4 represents a comparison of acid phosphatase produced in various yeast strains grown in YPD medium (Y) or SD—Pi medium (S) Crude supernatants from W303-1A, YNS-7A and DT111 cultures were concentrated on Centriprep-30 (Amicon) and lyophilized. Total proteins (10 µg) from each culture were glucosylated with RUGT and loaded on SDS-PAGE for Coomassie-blue staining, fluorography or TCA precipitated to quantitate the incorporation of $^3$H-glucose. The numbers below the autoradiogram indicate the percent incorporation of $^3$H-glucose in each of the protein samples relative to the sample which gave maximum incorporation (100%).

FIG. 6 represents the electrophoretic analysis of acid phosphatase glucosylated by wild-type and mutant RUGT. (Approximately 1 µg of acid phosphatase was glucosylated with either no RUGT (−), 0.25 µg (1) or 0.5 µg (2) of wild-type (WT) or mutant RUGT. The numbers below the autoradiogram indicate the percent incorporation of $^3$H-glucose for each mutant relative to the wild-type RUGT.

FIG. 8 represents DNA sequences from the 5' and 3'ends of the RUGT constructs and mutants in pFastBac-1; and FIGS. 9A–9G represents the protein sequence alignment of RUGT compared to other UGGTs (A) Full sequence alignment of RUGT, *D. melanogaster* UGGT, *C. elegans* UGGT, *S. pombe* UGGT and *S. cerevisiae* KRE5. The open arrowhead indicates the site of signal peptidase cleavage of RUGT. The closed arrowheads indicate the potential N-glycosylation sites of RUGT.

FIGS. 10A–10B is the sequence alignment of RUGT and other glycosyltransferases between residues 1324 and 1438. Residues D1334, D1336, Q1429 and N1433 are identified.

DETAILED DESCRIPTION OF THE INVENTION

Figure 1:
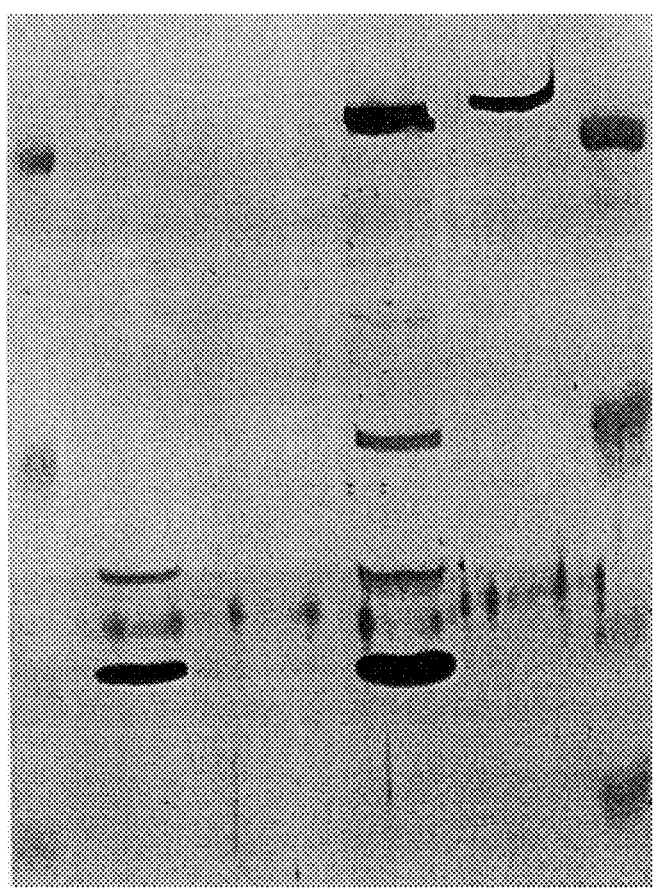
FIG. 1 represents a Western blot analysis of total cell extracts (C) and supernatant medium (S) taken at Day 0 and Day 3 from Sf9 insect cells infected with an RUGT-containing recombinant. The blot was probed with a rabbit antiserum raised against a 15 mer peptide corresponding to the C-terminus of RUGT. (M) Molecular weight standards.
Figure 2A:
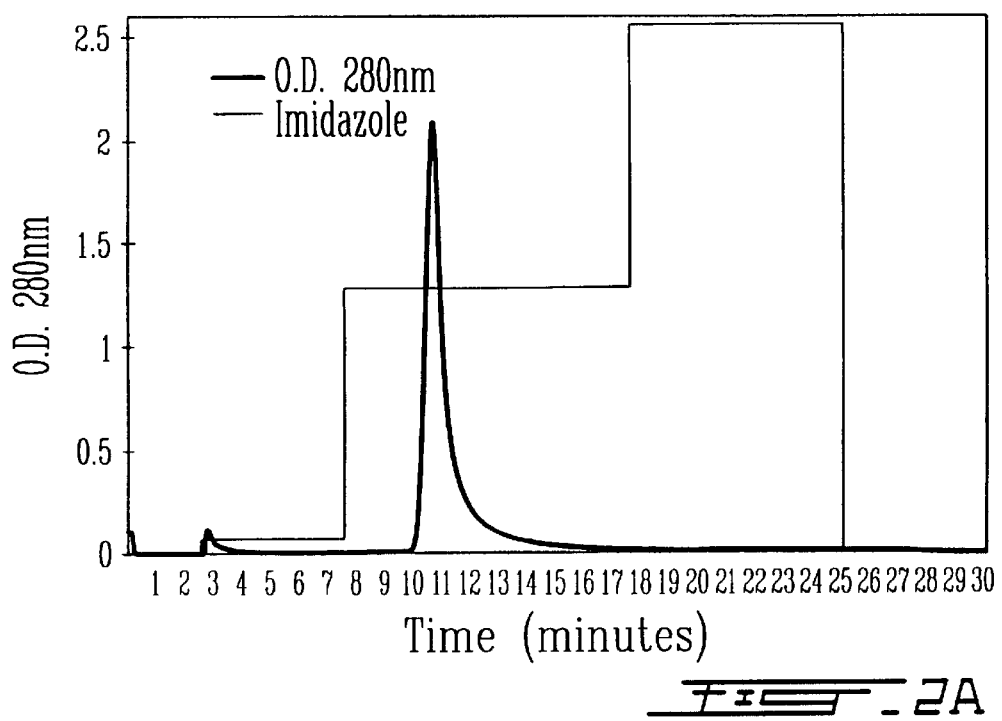
FIG. 2 represents chromatograms for the purification of RUGT and yeast acid phosphatase ((A) Elution profile of RUGT from Ni++−NTA Superflow column. The insect cell culture medium was concentrated, buffer exchanged and loaded on the column in buffer containing 10 mM imidazole. Proteins were eluted using 200 mM imidazole in 40 mM Tris-HCl ph 7.5, 500 mM NaCl, 5 mM $CaCl_2$. (B) Elution profile of RUGT from POROS 20HQ column. RUGT fractions from the Ni++−NTA column were pooled, diluted 10 fold and loaded on POROS 20HQ. RUGT was eluted using an NaCl gradient of 0–600 mM over 30 column volumes. The arrowhead indicates the RUGT peak. (C) Elution of yeast acid phosphatase from POROS 20HQ column. Yeast culture medium was concentrated, buffer exchanged and loaded onto POROS 20HQ. The enzyme was eluted over 30 column volumes using an NaCl gradient of 0–200 mM. The arrowhead indicates the peak of maximum acid phosphatase activity).
Figure 2B:
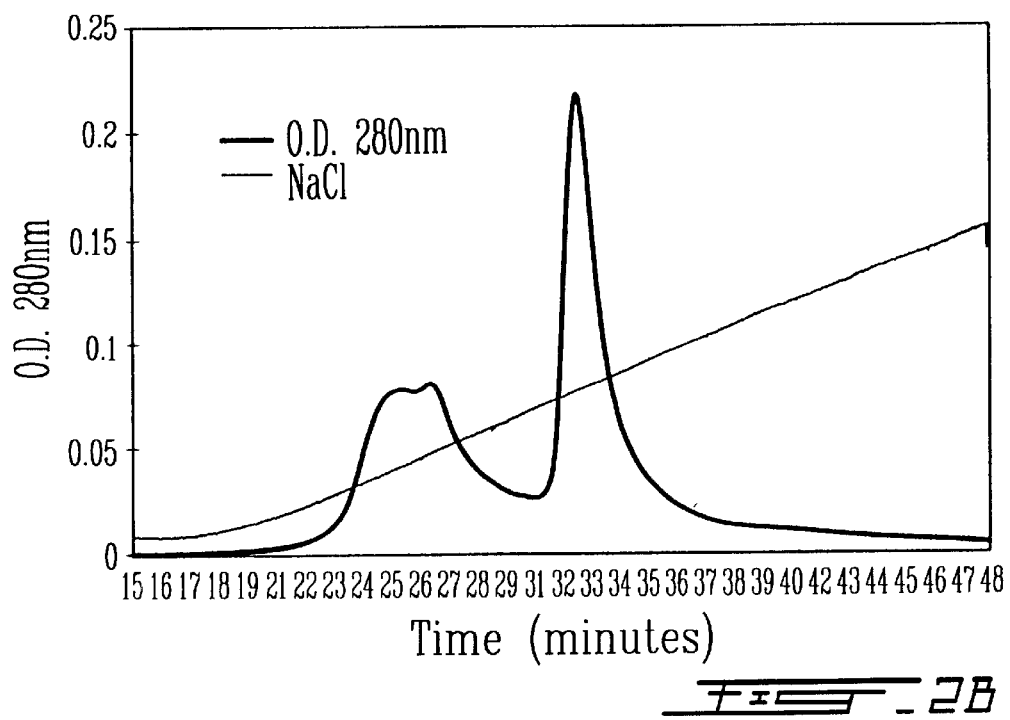

Prior to setting forth this invention it may be helpful to first define certain terms that will be used herein.

"test sample" means a sample to be assayed in the method of the present invention. The sample can include one or more compounds and can be a dry solid or a solution. The test sample can also be formulated when necessary.

"a UGGT acceptor substrate" means an unfolded protein which is found in the [GlcNAc]$_2$ (Man) 7–9 form and which can be glucosylated by UGGT by methods well known in the art. For example the substrate can be labeled by Glycoprotein [GlcNAc]$_2$ (Man) 7–9 denatred+UDP-[$^3$H]Glucose+UGGT.

"labeled donor" means a nucleoside diphosphate which is a suitable donor substrate for UGGT.

"folded protein" means a secretory protein in its biologically active form.

"unfolded protein" means a secretory protein in a non biologically active form or no longer in a bioactive form.

In a preferred embodiment of the present invention the UGGT acceptor substrate is selected from a group consisting of: yeast acid phosphatase, bovine pancreatic RNAse B, bovine thyroglobulin, soybean agglutinin, yeast exo (B-1,3) glucanase and a yeast α-galactosidase.

More preferably the UGGT acceptor substrate is yeast exo (B-1,3) glucanase, α-galactosidase and RNase B.

Most preferably the UGGT acceptor substrate is acid phosphatase.

In a preferred embodiment of the present invention the labeled donor is UDP-$^3$H-glucose.

The general conditions necessary for the method of the present invention are as follows:

10–20 mM Tris-HCl pH 7.5
5–10 mM CaCl$_2$
2.5–20 μM UDP-[$^3$H]Glucose
20–100 mM UGGT
0.5–1 μM acceptor substrate
37° C., 30 min—4 hours.

In accordance with the present invention there is provided an isolated nucleic acid comprising a cDNA as set forth in SEQ ID No:1.

In accordance with the present invention there is provided a recombinant vector comprising the isolated nucleic acid of the present invention.

In accordance with the present invention there is provided a host cell transfected with a recombinant vector comprising the isolated nucleic acid of the present invention.

In accordance with the present invention, there is provided a process for preparing a recombinant mammalian UGGT comprising the steps of:

a) culturing a host cell transfected with a recombinant vector comprising the isolated nucleic acid of the present invention under conditions wherein the said nucleic acid is expressed; and
b) recovering the mammalian UGGT so produced.

Preferably, the conditions are elution profile of RUGT from Ni++–NTA Superflow column. The insect cell culture medium was concentrated, buffer exchanged and loaded on the column in buffer containing 10 mM imidazole. Proteins were eluted using 20 mM imidazole in 40 mM Tris-HCl ph 7.5, 500 mM NaCl, 5 mM CaCl$_2$. (B) Elution profile of RUGT from POROS 20HQ column. RUGT fractions from the Ni++–NTA column were pooled, diluted 10 fold and loaded on POROS 20HQ. RUGT was eluted using an NaCl gradient of 0–600 mM over 30 column volumes. The arrowhead indicates the RUGT peak.

Preferably the host cell is a mammalian cell or an insect cell. More preferably the host cell is SF9 insect cells.

The eukaryotic host cells appropriate for use in the invention include, preferably, vertebrate cells and, more preferably, mammalian cells. Murine cell lines are especially preferred. However, in addition, other eukaryotes such as yeast cells may also be employed.

The elements of the recombinant vector are constructed using standard recombinant DNA techniques. The recombinant vectors of the present invention comprise a transcriptional promoter which is upstream of and operably linked to the isolated nucleic acid of the present invention. By "operably linked" is meant that the elements are ligated in such a fashion that their intended functions may be fulfilled. Thus, the promoter "operably linked" to the isolated nucleic acid of the present invention is ligated in such a position and manner as to be capable of effecting the transcription of these DNAs into mRNA.

Typically a host expression vector is constructed which includes the transcription promoter operably linked to the isolated nucleic acid of the present invention followed by termination control sequences such as transcription terminator sequences and polyadenylation sites. These termination controls can be supplied from appropriate host sources such as those that control the termination of transcription of eucaryotic mRNAs such as SV40 mRNAs.

Typical polylinker sequences for gene insertion can be constructed synthetically and will include a variety of restriction sites.

The expression vectors constructed according to the method of the invention are transfected or transformed into suitable recombinant host cells which are then cultured under conditions which permit the regulated production of the mammalian UGGT. The choice of host will depend on the nature of the transcription and translation-regulating elements selected for the expression system. Typically, the transfected cells are cultured under conditions where expression is repressed until a high density of cells is achieved. Then conditions appropriate for the induction of expression are superimposed on the culture and protein production is commenced. The mammalian UGGT produced is then recovered either from the supernatant or by cell lysis and purified using conventional means.

In accordance with the present invention, there is provided a cDNA or an analog thereof wherein said cDNA or analog thereof encodes for UGGT.

In accordance with the present invention, there is provided the first cloned mammalian UGGT successfully expressed in a baculovirus/insect cell system. Active RUGT was purified to homogeneity and exhibits the same preference for unfolded glycoproteins charged with N-linked [GlcNAc]2-(Man)9 glycans as the enzyme purified from rat liver. The enzyme shows homology to other UGGTs throughout the protein but more so in the C-terminal 300 residues of the *D. melanogaster, C. elegans* and *S. pombe* gene products.

The rat liver UGGT is the first mammalian UGGT to be sequenced. It shows a high degree of homology with the three other available sequences from the yeast *Schizosaccharomyces pombe*, the nematode *Ceanorabditis elegans*, and the fruit fly *Drosophila melanogaster*, with 31%, 43% and 43% of identity respectively, reflecting the evolutionary distance between these organisms (FIG. 9A). The sequence homology, although extending over the entire protein, is particularly high in a C-terminal region of about 300 residues from the end of the protein where the identity between the RUGT sequence and that of the *S. pombe* UGGT is 50%. A domain homologous to this C-terminal segment was found in other glycosyltransferases from various organisms such as bacterial lipopolysaccharide glucosyl- and galactosyltransferases and mammalian glycogenins. A few other proteins of unknown functions also appear to contain a similar domain. The UGGTs, the bacterial lipopolysaccharide, monosaccharide transferases and the glycogenins all catalyze the transfer of a monosaccharide from a nucleoside diphosphate donor onto a variety of different substrates. It is therefore likely that their regions of homology would contain the active site where the donor substrate is bound, while the rest of the protein may be involved in the recognition of the acceptor substrate.

Two short stretches are particularly conserved, corresponding to residues 1329 to 1351, and 1428 to 1435 of the mature RUGT (FIG. 9B). Four residues are entirely conserved suggesting a potential role in the function of these various proteins. In RUGT, these residues are D1334, D1336, Q1429, and N1433. To test if these residues are important for the function of RUGT, they were all individually mutated for alanines (FIG. 8) and the activity of the resulting proteins was determined. These four amino acid residues appear to be involved at various degrees in catalytic activity. The first two residues completely abolish enzyme activity when they are mutated to alanines. The other two mutants retain about 2% and 20% of the activity of the wild-type. These residues are responsible either for the binding of the donor-substrate UDP-glucose to RUGT or in the actual catalytic transfer of the glucose residue to the acceptor-substrate.

Two models emerge whereby RUGT would glucosylate every N-linked glycan on the acceptor-substrate like beads on a string or it may only recognize and glucosylate one or very few key sites along the denatured polypeptide chain. The first model could explain the possible substrate/product inhibition observed in the experiment designed to determine the Km for acid phosphatase as incompletely glucosylated substrate molecules would remain bound to the enzyme thus preventing binding of other substrate molecules. The second model is much more appealing in that it implies that the oligosaccharide alone cannot constitute a complete target for RUGT and that other peptide-specific determinants exposed in the unfolded polypeptide chain have to be recognized as well. This selective glucosylation model would imply the existence of specific/strategic sites for the binding of calnexin and/or calreticulin in the mechanism of refolding of glycoproteins in the ER.

In accordance with the present invention there is provided a strain of S. cerevisiae capable of producing asparagine-linked [GlcNAc]2-(Man) 9 glycoproteins. Acid phosphatase, a naturally secreted yeast protein, was overexpressed in this strain and constitutes an excellent source of substrate for UGGT.

For expression in baculovirus/insect cells, the full cDNA encoding RUGT was subcloned in pFastBac-1. The native signal sequence of RUGT was substituted for the honeybee melittin signal peptide to improve secretion (Tessier 1991). Furthermore, the ER retention signal HEEL at the C-terminal end of the protein was replaced by 6 histidine residues to allow release from the ER and facilitate purification. At 72 hours post-infection, approximately 50% of the expressed RUGT was secreted in the insect cell culture medium (FIG. 8). The secreted form of RUGT was purified to approximately 40% homogeneity by immobilized metal-chelate affinity chromatography and further to greater than 95% by anion exchange chromatography (FIG. 3; lane 6). From 400 ml of culture medium, 500 μg of RUGT could be purified to near homogeneity as judged by Coomassie-blue staining (FIG. 3). Similar yields were obtained with all four RUGT mutants D1334A, D1336A, Q1429A, and N1433A indicating that the mutations do not appear to affect the stability of the enzyme.

To produce a substrate for RUGT, the S. cerevisiae strain YNS-7A known to produce mainly [GlcNAc]2-(Man)8 oligosaccharides was further deleted of its MNS1 gene which encodes an ER α-mannosidase responsible for the trimming of the [GlcNAc]2-(Man)9 oligosaccharides to [GlcNAc]2-(Man)8 (Jelinek-Kelly, 1988 and Camirand, 1991). The resulting strain was called DT111. Secreted proteins from YNS-7A and DT111 were found to be much better substrates for RUGT than proteins secreted from the wild-type W303-1A strain regardless of the growth conditions (FIG. 4). Furthermore, the incorporation of $^3$H-glucose was even better in proteins secreted from DT111 than from YNS-7A, as [GlcNAc]2-(Man)9 glycans are known to be better acceptors than [GlcNAc]2-(Man)8 (Sousa, 1992).

These glycosylation deficient strains could eventually be used to produce recombinant proteins with tailored oligosaccharides. The yeast protein, acid phosphatase was a good candidate as it is highly glycosylated. Moreover, acid phosphatase loses activity at neutral pH suggesting that it may unfold under these conditions, thus by-passing the need for a denaturation step prior to the glucosylation reaction. Four acid phosphatase isoforms are encoded by four different genes PHO3, PHO5, PHO11 and PHO12 (Bajwa, 1984; Arima, 1983; Bussey, 1995; Johnson, 1994). PHO5 is responsible for the majority of the acid phosphatase synthesized and is further derepressed when cells are starved for inorganic phosphate (Tait-Kamradt, 1986). The PHO5 gene product has a predicted molecular weight of 51.1 kDa, a theoretical pI of 4.60 and has 12 potential glycosylation sites.

Figure 5:
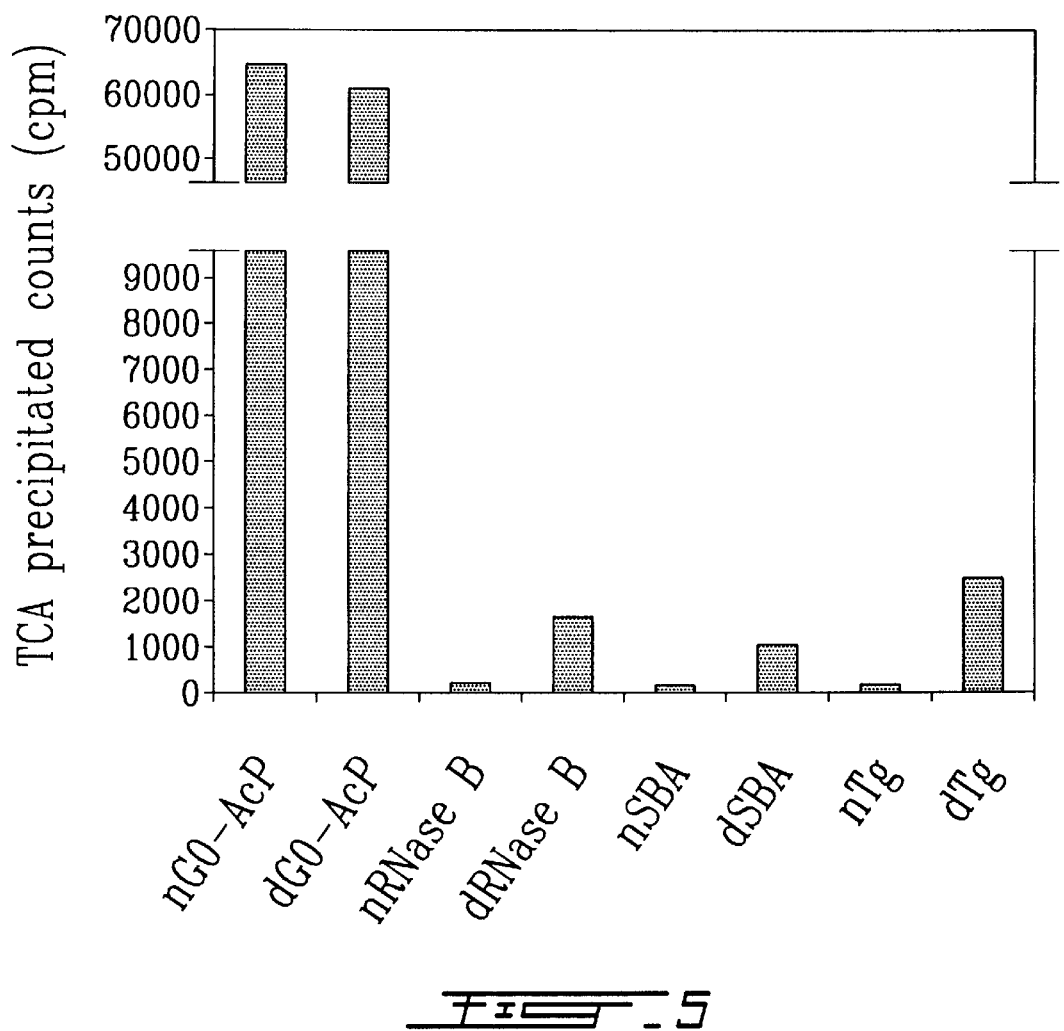
FIG. 5 represents the incorporation of $^3$H-glucose in various glycoprotein acceptor-substrates. Native (n) and denatured (d) acid phosphatase (AcP), RNase B, soybean agglutinin (SBA) and thyroglobulin (Tg), 1 µg of each, were glucosylated by RUGT. Note: Native AcP is fully denatured at pH 7.5.

Under inorganic phosphate starvation, the secretion of high molecular weight proteins seems to be stimulated in strain W303-1A (FIG. 4). These proteins appearing as a smear on SDS-PAGE are expected for acid phosphatase because it would be heterogenously hyperglycosylated in a wild-type strain. In YNS-7A and DT111, the secretion of a protein of about 80 kDa was increased under inorganic phosphate starvation. This molecular weight would be expected for acid phosphatase having [GlcNAc]2-(Man)8 and [GlcNAc]2-(Man)9 core oligosaccharides respectively. Although crude culture supernatants from DT111 could be used as substrate for RUGT, a simple change of buffer by ultrafiltration followed by anion exchange chromatography could yield a single protein of ~80 kDa. N-terminal sequencing of the purified protein has revealed the identity of acid phosphatase. Complete treatment of purified acid phosphatase with EndoH resulted in a reduction of >20 kDa of the apparent molecular weight on SDS-PAGE indicative of ~12 glycosylation sites (data not shown). About 7 mg of >90% pure acid phosphatase could be obtained from 14 liters of DT111 cells grown in SD—Pi medium in a bioreactor to a maximum O.D.600 nm of 2. The activity of the purified recombinant RUGT was tested towards various substrates. As expected the enzyme showed a greater activity towards reduced unfolded RNase B than towards the native protein. Similarly, heat-treated soybean agglutinin and urea-treated bovine thyroglobulin were better substrates than the native proteins (FIG. 5). These results demonstrate that the recombinant enzyme has the same specificity for incorrectly folded proteins as the enzyme purified from rat liver.

Denatured acid phosphatase purified from DT111 is a much better acceptor substrate for RUGT than the previously used bovine thyroglobulin and soybean agglutinin. Assuming MW of 14 kDa, 31 kDa and 303 kDa for RNase B, SBA and Tg, acid phosphatase can incorporate $^3$H-glucose on a molar basis 130× better than RNase B, 100× more than SBA and 4 times more than tg. When UDP-glucose was used in large excess, and the glucosylation reaction allowed to proceed to completion, the maximum incororation indicated that nearly all 12 glycosylation sites of acid phosphatase are used for glucosylation. This suggested that complete denaturation of acid phosphatase by reduction of its disulfide bonds in the presence of 6M guanidinium hydrochloride (Zapun, 1998) followed by desalting prior to glucosylation, did not result in a better incorporation of $^3$H-glucose (FIG. 5). Thus, it would appear that all of the N-linked glycans in acid phosphatase are recognized and used as targets for glucosylation by RUGT.

The activity of the four RUGT mutants was compared with that of the wild-type enzyme using purified acid phosphatase. The D1334A and D1336A mutants exhibited no activity at all, whereas the N1433A and Q1429A mutant showed approximately 2% and 20% of the activity of the wild-type enzyme (FIG. 6). The autoradiogram was overexposed to show the weak labeling of acid phosphatase by RUGT- Q1429A and N1433A.

Figure 7A:
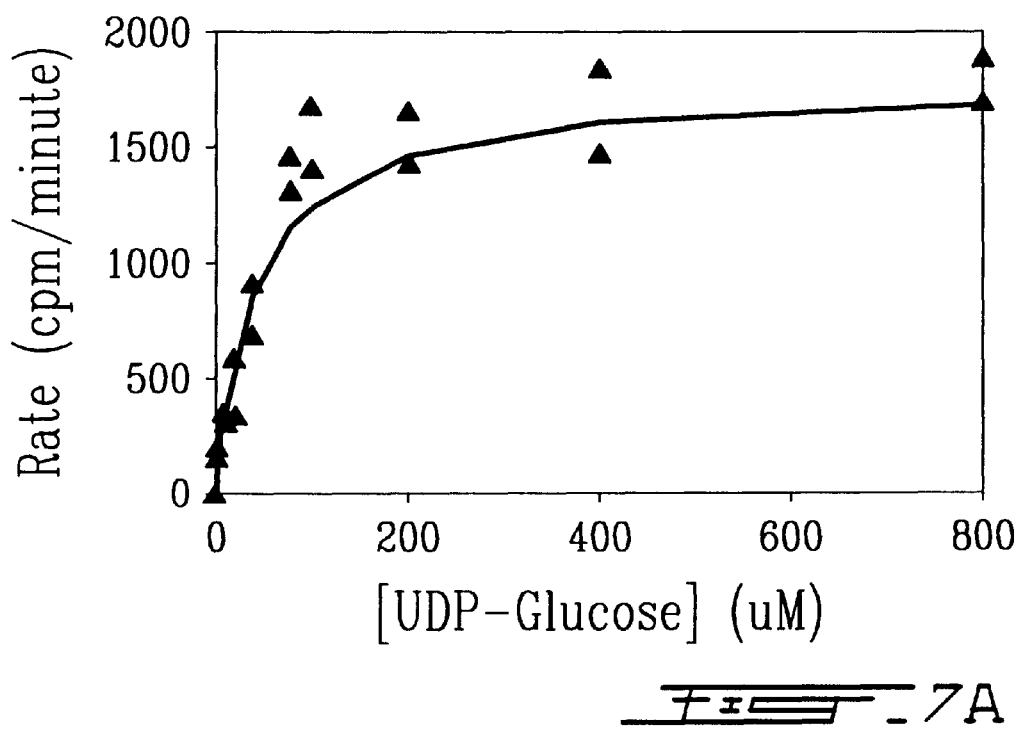
FIG. 7 represents the determination of the Km of UDP-glucose (A) and acid phosphatase (B) for RUGT. Plots of rate vs. substrate concentration.
Figure 7B:
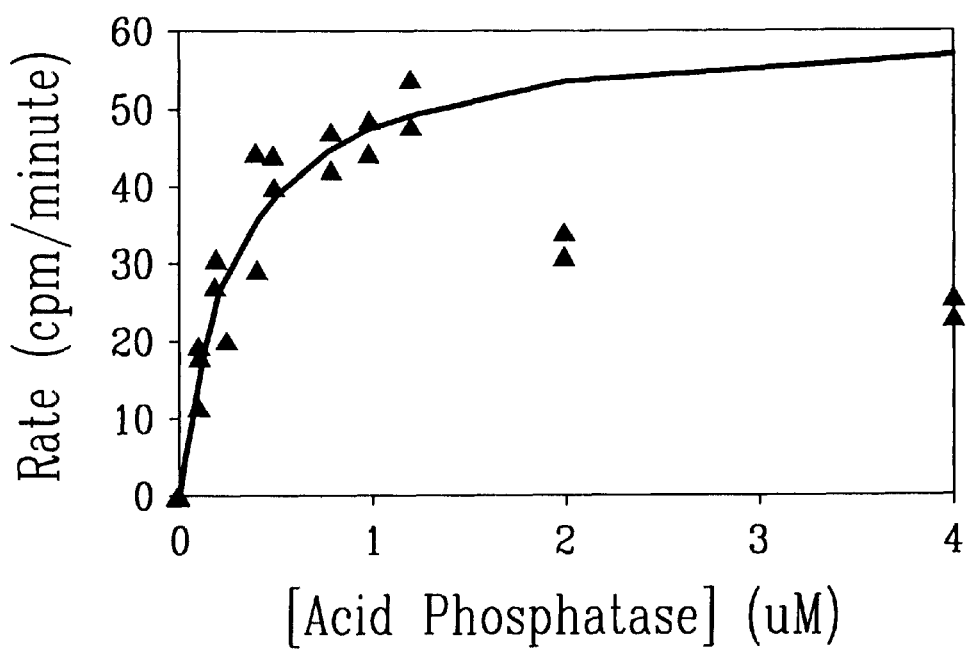

Preliminary kinetic characterization of RUGT was conducted and its Km for UDP-glucose and acid phosphatase was determined. In the presence of 0.5 μM acid phosphatase, the enzyme exhibited classical Michaelis-Menten kinetics (FIG. 7A) and it was possible to calculate a Km of 44 μM for UDP-glucose. A Km of 18 μM was previously obtained by Trombetta using both soybean agglutinin or bovine thyroglubulin as acceptor substrates for rat liver-purified UGGT in 10 mM Tris-HCl pH7.5, 10 mM CaCl2 (unpublished results). However, in the presence of 5 μM UDP-glucose, an apparent Vmax at 1.0 μM acid phosphatase was observed (FIG. 7B). As the acid phosphatase concentration was increased to 2.0 and 4.0 μM, the rate of glucosylation continued to decrease perhaps indicative of substrate and/or product inhibition. In any case, the apparent Km for acid phosphatase was calculated to be 0.3 μM. This result could be explained if the acid phosphatase did not get released from RUGT following glucosylation. Although it has been shown in vivo that association of a secretion-incompetent variant of α1-antitrypsin to UGGT is prevented in the presence of UDP-glucose (Choudhury, 1996).

Other characteristics and advantages of the present invention will appear from the following example. The following example is intended to document the invention, without limiting its scope.

EXAMPLE I

Cloning and Expression in Insect Cells of Active Rat Liver UDP-Glucose Glycoprotein:Glucosyltransferase and Development of an Adequate Substrate for this Enzyme Cloning of RUGT Restriction and modification enzymes were obtained from Pharmacia Biotech Inc., New England BioLabs and MBI Fermentas Inc. Plasmid pFastBac1, *E.coli* DH10Bac and the 5' RACE System for Rapid Amplification of cDNA Ends (Version 2.0) were all purchased from Gibco/Life Technologies Inc. The Marathon cDNA Amplification Kit and Marathon-Ready cDNA were purchased from Clontech. Plasmids were propagated in *E.coli* MC1061 (Casadaban, 1980) and prepared as described previously (Holmes, 1981). Oligonucleotides were synthesized on an Expedite DNA Synthesizer (PerSeptive Biosystems, Inc.) and sequencing was done by dideoxy dye termination on an ABI Prism 377 DNA Sequencer (Applied Biosystems Inc.).

In order to obtain the coding sequence of the rat UGGT, a strategy of cDNA "walking" was first followed. Based on peptide sequence information and a 300 bp stretch of sequence at the 3' end of the gene, oligonucleotide probes were designed and used to screen a rat liver cDNA library in Lambda ZAP (Stratagene). Two similar clones of 3.3 kb were isolated which contained an open reading frame encoding the C-terminal 385 amino acids, including an ER retention sequence and a poly(A) tail at the 3'end. The screening of a new rat liver cDNA library in λgt10 (Clontech) with a second probe corresponding to the 5'end of the 3.3 kb clone isolated in the first screening gave several overlapping clones. The most interesting one extended the 3.3 kb clone further with 1.7 kb of sequence from which a third probe was designed. In this third screening, only one positive clone was obtained which extended the open reading frame by 540 bp to 3360 bp. A fourth probe was designed based on this additional sequence information but failed to produce useful clones. Subsequently, no full length sequence of the RUGT ORF were found in any library used.

To complete the sequence, the 5' RACE System was used on rat liver mRNAs. The reverse transcriptase reaction was primed with an oligonucleotide corresponding to the 5'end of the 540 bp of sequence information revealed in the third screening. The first strand cDNA was later tailed with poly(dC) using terminal deoxynucleotidyl transferase. An amplified fragment of 1.4 kb was cloned and sequenced. The 5' sequence of this clone consisted of a poly-dG stretch followed by a GC-rich segment of 39 bp preceeding the open reading frame. Using this sequence information, RT-PCR was carried out using Clontech's Marathon cDNA kits to clone the full length cDNA as a single fragment of 4.6 kb using primers immediately flanking the coding region. Two clones from independent reactions were sequenced.

For expression, the gene was cloned in the RsrII and KpnI sites of pFastBac1 using the following strategy. At the 5'end of the gene, the sequence coding for the first 18 amino acids of RUGT was replaced by the sequence coding for the 21 amino acids of the honeybee melittin signal peptide to facilitate the secretion of the protein from baculovirus-infected insect cells (Tessier, 1991). At the extreme 3'end of the gene, the sequence coding for the ER localization signal HEEL was replaced by the sequence coding for a terminal (His)6 tag to facilitate purification of the protein (FIG. 8).

Based on sequence alignments with other nucleoside diphosphate glycosyltransferases, four independent RUGT mutants D1334A, D1336A, Q1429A and N1433A were designed, amplified by PCR, cloned and sequenced to confirm the presence of diagnostic PstI, BsrBI, XbaI and NaeI sites respectively (FIG. 8).

Recombinant Baculovirus Production and Expression in Insect Cells

Recombinant RUGT constructs in pFastBac1 were transformed in *E.coli* DH10Bac to produce recombinant bacmids as described by the manufacturer. The presence of the gene was verified by PCR. Sf9 insect cells were transfected for 3 days with the recombinant bacmid DNA using CellFectin (Gibco/Life Technologies Inc.) as described by the manufacturer to produce stocks of recombinant RUGT baculovirus.

Sf9 insect cells were grown for 3–4 days in Sf900 II SFM serum-free medium (Gibco/Life Technologies Inc.) to a density of 2–3×106 cells/ml in 500 ml micro-carrier Spinner flasks (Bellco Glass Inc.) and infected with ⅟20 of the culture volume of a recombinant RUGT baculovirus stock representing an approximate M.O.I. of 2–5 pfu/cell. The infected cells were then incubated at 27° C. for up to 3 days. Aliquots of the infected cells and of the culture supernatant were analyzed on 5% stacking/8% resolving SDS-polyacrylamide gels (SDS-PAGE) followed by Western blotting.

Purification of RUGT

Cells were removed by centrifugation at 3,000×g for 10 minutes. The supernatant medium was collected on ice and adjusted to 40 mM Tris-HCl pH 7.5, 0.5M NaCl. The medium was concentrated approximately 20 fold at 4° C. on YM30 membranes (Amicon) in the presence of 2 mg/ml of the protease inhibitors aprotinin, leupeptin, pepstatin A and E-64 (Boehringer Mannheim Canada). Two buffer exchanges were performed using Buffer ATC/PI (40 mM Tris-HCl pH 7.5, 0.5M NaCl, 5 mM CaCl2 with Protease Inhibitors).

The concentrated/diafiltrated medium was centrifuged at 3,000×g for 10 minutes to remove some precipitated proteins and 10 mM imidazole was added to the supernatant before loading twice by gravity flow onto a 1 ml $Ni^{++}$-NTA Superflow column (Qiagen Inc.) in a Pharmacia FPLC C-type column assembly. The Ni++-NTA resin had been previously washed with 20 column volumes of ddH2O and equilibrated in Buffer ATC/PI+10 mM imidazole. After loading, the column was washed by gravity flow with 20 column volumes of Buffer ATC/PI+10 mM imidazole. Elution was carried out on a BioCAD Perfusion Chromatography Workstation (PerSeptive Biosystems, Inc.). The column was first washed with 10 column volumes of Buffer ATC/PI+10 mM imidazole at 2 ml/min and proteins eluted with Buffer ATC/PI+200 mM imidazole for 20 column volumes at the same flow rate. Fractions of 1 ml were collected and aliquots analyzed by SDS-PAGE and Western blot to confirm the presence of the protein.

RUGT-containing fractions from the $Ni^{++}$-NTA column were diluted 10 fold with HQ buffer (40 mM Tris-HCl pH 7.5, 2 mM CaCl2) before injecting onto a 1 ml POROS 20HQ column (PerSeptive Biosystem, Inc.) in an Pharmacia FPLC HR5/5 column assembly on a BioCAD. Flow rates for the binding and the elution were set at 1 ml/min while the washes were done at 3 ml/min. The protein was eluted with an NaCl gradient of 0–750 mM in HQ buffer over 30 column volumes. RUGT eluted at approximately 350 mM NaCl. Fractions of 1 ml were collected and aliquots analyzed by SDS-PAGE to assess the purity of the protein and to test for RUGT activity.

Production of Acid Phosphatase

The *Saccharomyces cerevisiae* yeast strains used in this study were : W303-1A (MATa, ade2, his3, leu2, trp1, ura3, can1) (Parlati, 1995), YNS-7A (MAT a, och1::LEU2, mnn1, his1, his3, ura3; generous gift from Y. Jigami) (Nakayama, 1991) and DT111 (MAT a, och1::LEU2, mnn1, mns1, his1, his3, ura3). Acid phosphatase was produced from DT111 which secretes glycoproteins with asparagine-linked [GlcNAc]2-(Man) 9 glycans. DT111 was constructed by disrupting the MNS1 gene of YNS-7A using an mns1::URA3 cassette (Camirand, 1991) from plasmid pBHE5 (generous gift from A. Herscovics). The URA3 gene was later deleted by selecting for 5-FOA-resistant colonies (Rose, 1990). DT111 was grown in YPD medium supplemented with 150 mM KCl as an osmotic stabilizer at 30° C. until the O.D.600 nm reached about 5. The inoculum was diluted 50 fold in SD—Pi medium supplemented with 150 mM KCl and 2% glucose and grown at 30° C. to an O.D. 600 nm of 2. The SD medium (Rose, 1990) was prepared without inorganic phosphate to induce the expression of endogenous acid phosphatase. Acid phosphatase was purified from the culture medium by 50 fold concentration/diafiltration against 10 mM sodium acetate pH 5.0 followed by anion exchange chromatography on a 1 ml POROS 20HQ column (PerSeptive Biosystems, Inc.) in a Pharmacia HR5/5 assembly in 20 mM sodium acetate pH 5.0 on a BioCAD. The flow rates were set at 1 ml/min for the binding and 3 ml/min for the washes. Proteins were eluted at 1 ml/min over 30 column volumes using a linear gradient of 0–600 mM NaCl. Acid phosphatase eluted at approximately 100 mM NaCl. Fractions of 1 ml were collected and aliquots analyzed by SDS-PAGE to confirm the presence of the protein. Acid phosphatase activity was monitored at O.D.405 nm following the hydrolysis of 1 mg/ml p-nitrophenyl phosphate (pNPP; Sigma 104) at 37° C. for 10–60 minutes in 25 mM sodium acetate pH 4.0.

Glucosyltransferase Assay and Kinetics Measurements

Acid phosphatase was the major substrate glycoprotein used to determine RUGT activity in this study. RNase B was prepared as described elsewhere (Zapun, 1998). Soybean agglutinin (Sigma) was denatured by heating at 100° C. for 15 minutes. Bovine thyroglobulin (Sigma) was denatured with 8M urea and dialyzed against ddH2O. The acid phosphatase acceptor-substrate (~1 µg) was mixed with RUGT in a 20 µl mixture containing TC buffer (10 mM Tris-HCl pH 7.5, 10 mM CaCl2) and 5 µM uridine diphospho-D-[6-$^3$H]-glucose (2–15 Ci/mmol; Amersham Life Science Inc.) and incubated at 37° C. for 2 hours. Reactions were either analyzed by SDS-PAGE followed by fluorography using Amplify (Amersham Life Science Inc.) or precipitated with ice-cold 10% trichloroacetic acid (TCA), washed twice with TCA and the pellets resuspended in 50 µl 1M Tris-HCl pH 8.0 before counting in a beta counter to quantitate the incorporation of $^3$H-glucose in acid phosphatase.

For the determination of the Km of UDP-glucose, 46 nM RUGT was mixed with 1 µM of purified acid phosphatase and 5–800 µM UDP-glucose (mixture of labeled and unlabeled) in TC buffer in a final volume of 20 ml. For the determination of the Km for acid phosphatase, 10 nM RUGT was mixed with 100 µM UDP-glucose (mixture of labeled and unlabeled) and 0.1–4 µM of purified acid phosphatase in TC buffer in a final volume of 20 µl. Glucosylation reactions were incubated at 37° C. and TCA precipitated at various times up to 120 minutes to determine the rate of incorporation of $^3$H-glucose in acid phosphatase.

Production of Polyclonal Antibodies Directed Against the C-terminus of RUGT

The 15 mer peptide EEKELGTLHEEETQE (amino acid residues 1505–1519) was synthesized on an 8-branch MAP core (Applied Biosystems) on an MPS 396 Peptide Synthesizer (Advanced Chemtech) using Fmoc chemistry and desalted on C18 Sep-Pak reverse phase chromatography cartridges (Millipore/Waters). Rabbits were immunized as described by previously (Cooper, 1995). Periodical bleedings were tested for immunoreactivity to RUGT by Western blotting and visualized by enhanced chemiluminescence (ECL; Amersham Life Science Inc.). Antibodies generated for this study showed cross-reactivity to two insect cell proteins of about 62 and 70 kDa respectively (FIG. 1).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for determining the effect of a test sample on UGGT activity which comprises the steps of:
   a) exposing an acceptor substrate for UDP-glucose:glycoprotein glucosyltransferase (UGGT) to a labeled donor in the presence of the test sample and UGGT of amino acid sequence as set forth in SEQ ID NO: 2; and
   b) detecting the amount of donor intake which was transferred to the UGGT acceptor substrate wherein a decrease of donor intake when compared to a control means that the test sample is a UGGT stimulator and a decrease means that the test sample is a UGGT inhibitor.

2. An isolated nucleic acid comprising a cDNA as set forth in SEQ ID NO: 1 which encodes for UGGT.

3. A recombinant vector comprising an isolated nucleic acid as described in claim 2.

4. A host cell transfected with a recombinant vector as defined in claim 3.

5. A process for preparing a recombinant mammalian UGGT comprising the steps of
   a) culturing the transfected host cell as defined in claim 4 under conditions wherein said nucleic acid is expressed; and
   b) recovering the mammalian UGGT so produced.

6. An *S. cerevisiae* strain DT111 which produces asparagine-linked [GlcNAc]2-(Man)9 glycoproteins.

7. The method of claim 1, wherein said acceptor substrate for UGGT is produced by the *S. cerevisiae* strain DT111.

* * * * *

SEQUENCE LISTING

<160> NUMBER OF SEQ ID NOS: 35

<210> SEQ ID NO 1
<211> LENGTH: 5053
<212> TYPE: DNA
<213> ORGANISM: Rat RUGT
<220> FEATURE:
<221> NAME/KEY: CDS
<222> LOCATION: (40)...(4623)

<400> SEQUENCE: 1

```
tgcgcggctg cgcggcgggt gacagggctc tgttacaac atg gga ctc ctg att                54
                                            Met Gly Leu Leu Ile
                                             1               5 gca ctg gcc tta ctg tgc ctg ttt tcc tta gca gaa gcc aat tca aaa               102
Ala Leu Ala Leu Leu Cys Leu Phe Ser Leu Ala Glu Ala Asn Ser Lys
             10                  15                  20 gcc att acc acc tct ctc acc act aag tgg ttt tct gct cca ctg ctg              150
Ala Ile Thr Thr Ser Leu Thr Thr Lys Trp Phe Ser Ala Pro Leu Leu
         25                  30                  35 cta gaa gcc agt gag ttc cta gca gaa gac agt caa gag aaa ttt tgg             198
Leu Glu Ala Ser Glu Phe Leu Ala Glu Asp Ser Gln Glu Lys Phe Trp
     40                  45                  50 agt ttt gta gaa gcc agt caa aac att gga tca tca gat caa cat gat             246
Ser Phe Val Glu Ala Ser Gln Asn Ile Gly Ser Ser Asp Gln His Asp
 55                  60                  65 acc gac cgt tcc tat tat gat gcc ata ttg gaa gct gcg ttt cgg ttc             294
Thr Asp Arg Ser Tyr Tyr Asp Ala Ile Leu Glu Ala Ala Phe Arg Phe
 70                  75                  80                  85 ctg tca cct ctg cag cag aat ttg ttg aag ttt tgt ctc tct ctc cgt             342
Leu Ser Pro Leu Gln Gln Asn Leu Leu Lys Phe Cys Leu Ser Leu Arg
             90                  95                 100 tcc tac tca gcc tca att caa gcc ttc cag cag ata gca gtc gac gag             390
Ser Tyr Ser Ala Ser Ile Gln Ala Phe Gln Gln Ile Ala Val Asp Glu
            105                 110                 115 cct cca cca gaa gga tgc aag tca ttt ctc tca gtg cat gga aag cag             438
Pro Pro Pro Glu Gly Cys Lys Ser Phe Leu Ser Val His Gly Lys Gln
            120                 125                 130 act tgt gat ctg ggc act ctt gag agc ctt ctg ctg act gca cct gac             486
Thr Cys Asp Leu Gly Thr Leu Glu Ser Leu Leu Leu Thr Ala Pro Asp
            135                 140                 145 aga cct aaa cct tta ttg ttc aaa gga gat cac aga tat ccc tca tca             534
Arg Pro Lys Pro Leu Leu Phe Lys Gly Asp His Arg Tyr Pro Ser Ser
150                 155                 160                 165 aat cct gaa agt cca gtg gtc att ttt tat tct gag att ggc cat gaa             582
Asn Pro Glu Ser Pro Val Val Ile Phe Tyr Ser Glu Ile Gly His Glu
                170                 175                 180 gaa ttt tct aat att cac cac caa ctt ata tca aaa agc aat gaa gga             630
Glu Phe Ser Asn Ile His His Gln Leu Ile Ser Lys Ser Asn Glu Gly
            185                 190                 195 aaa att aat tat gtg ttc aga cat tat ata tct aat ccc agg aag gag             678
Lys Ile Asn Tyr Val Phe Arg His Tyr Ile Ser Asn Pro Arg Lys Glu
            200                 205                 210 ccg gtc cac ctt tct ggc tat ggt gta gaa ttg gcc att aag agc acg             726
Pro Val His Leu Ser Gly Tyr Gly Val Glu Leu Ala Ile Lys Ser Thr
            215                 220                 225 gag tac aag gcc aag gat gat act cag gtg aaa ggg acc gag gta aac             774
Glu Tyr Lys Ala Lys Asp Asp Thr Gln Val Lys Gly Thr Glu Val Asn
230                 235                 240                 245
```

-continued

| | |
|---|---|
| acc aca gtc att ggg gag aac gat cct att gat gaa gtt cag ggg ttc<br>Thr Thr Val Ile Gly Glu Asn Asp Pro Ile Asp Glu Val Gln Gly Phe<br>          250                 255                 260 | 822 |
| ctc ttt gga aaa tta aga gaa ctg tac ccc agc ttg gaa gga cag ttg<br>Leu Phe Gly Lys Leu Arg Glu Leu Tyr Pro Ser Leu Glu Gly Gln Leu<br>      265                 270                 275 | 870 |
| aaa gag ttc cgg aag cat ctc gtg gag agc acc aat gaa atg gcc ccc<br>Lys Glu Phe Arg Lys His Leu Val Glu Ser Thr Asn Glu Met Ala Pro<br>  280                 285                 290 | 918 |
| ttg aaa gtc tgg cag ctg caa gac ctc agt ttc cag act gct gcc cgc<br>Leu Lys Val Trp Gln Leu Gln Asp Leu Ser Phe Gln Thr Ala Ala Arg<br>295                 300                 305 | 966 |
| atc ttg gct gct cct gtg gag tta gct ctg gtg gtg atg aag gac att<br>Ile Leu Ala Ala Pro Val Glu Leu Ala Leu Val Val Met Lys Asp Ile<br>310                 315                 320                 325 | 1014 |
| agt cag aac ttt cct acc aaa gcc aga gca ata aca aaa aca gct gtg<br>Ser Gln Asn Phe Pro Thr Lys Ala Arg Ala Ile Thr Lys Thr Ala Val<br>          330                 335                 340 | 1062 |
| agc gca cag ctt aga gcg gaa gtg gaa gag aac cag aag tat ttc aag<br>Ser Ala Gln Leu Arg Ala Glu Val Glu Glu Asn Gln Lys Tyr Phe Lys<br>      345                 350                 355 | 1110 |
| gga act ata gga tta cag cct gga gac tca gct ctc ttc atc aac gga<br>Gly Thr Ile Gly Leu Gln Pro Gly Asp Ser Ala Leu Phe Ile Asn Gly<br>  360                 365                 370 | 1158 |
| ctt cat att gat tta gac acc cag gat atc ttc agt ctg ttt gat act<br>Leu His Ile Asp Leu Asp Thr Gln Asp Ile Phe Ser Leu Phe Asp Thr<br>375                 380                 385 | 1206 |
| ctg aga aat gaa gcc cgg gta atg gag ggt cta cat aga cta gga ata<br>Leu Arg Asn Glu Ala Arg Val Met Glu Gly Leu His Arg Leu Gly Ile<br>390                 395                 400                 405 | 1254 |
| gaa ggc ctt tct cta cat aat att ttg aag ctc aac atc cag ccg tct<br>Glu Gly Leu Ser Leu His Asn Ile Leu Lys Leu Asn Ile Gln Pro Ser<br>          410                 415                 420 | 1302 |
| gag act gac tac gca gta gac atc agg agt cct gct att tcc tgg gtc<br>Glu Thr Asp Tyr Ala Val Asp Ile Arg Ser Pro Ala Ile Ser Trp Val<br>      425                 430                 435 | 1350 |
| aac aac cta gag gtt gat agc cga tat aac tca tgg cct tca agt tta<br>Asn Asn Leu Glu Val Asp Ser Arg Tyr Asn Ser Trp Pro Ser Ser Leu<br>  440                 445                 450 | 1398 |
| caa gag tta ctt cgc ccc acg ttt cct ggc gtt ata cgg cag atc aga<br>Gln Glu Leu Leu Arg Pro Thr Phe Pro Gly Val Ile Arg Gln Ile Arg<br>455                 460                 465 | 1446 |
| aag aac cta cat aac atg gtt ttc att gtt gat cct gtt cat gag acc<br>Lys Asn Leu His Asn Met Val Phe Ile Val Asp Pro Val His Glu Thr<br>470                 475                 480                 485 | 1494 |
| acg gca gag ctg gtt agc ata gcc gag atg ttc ctc agc aat cat ata<br>Thr Ala Glu Leu Val Ser Ile Ala Glu Met Phe Leu Ser Asn His Ile<br>          490                 495                 500 | 1542 |
| cca cta agg att ggt ttt atc ttt gtg gtc aat gat tct gaa gat gtt<br>Pro Leu Arg Ile Gly Phe Ile Phe Val Val Asn Asp Ser Glu Asp Val<br>      505                 510                 515 | 1590 |
| gat ggg atg caa gat gct gga gtc gct gtt ctg aga gca tat aat tat<br>Asp Gly Met Gln Asp Ala Gly Val Ala Val Leu Arg Ala Tyr Asn Tyr<br>  520                 525                 530 | 1638 |
| gtg ggt cag gaa gtg gat ggc tac cat gcc ttc cag act ctc acc cag<br>Val Gly Gln Glu Val Asp Gly Tyr His Ala Phe Gln Thr Leu Thr Gln<br>535                 540                 545 | 1686 |
| atc tac aac aaa gtg agg act gga gaa aag gtg aaa gtt gag cat gtg<br>Ile Tyr Asn Lys Val Arg Thr Gly Glu Lys Val Lys Val Glu His Val<br>550                 555                 560                 565 | 1734 |

-continued

```
gtc agt gtc ttg gag aag aag tac ccg tat gtt gaa gtg aat agc att     1782
Val Ser Val Leu Glu Lys Lys Tyr Pro Tyr Val Glu Val Asn Ser Ile
            570                 575                 580 ctg ggg att gat tct gct tat gat cag aat cgg aag gaa gcc aga ggc     1830
Leu Gly Ile Asp Ser Ala Tyr Asp Gln Asn Arg Lys Glu Ala Arg Gly
                585                 590                 595 tac tat gag cag act ggt gta ggc ccc ttg cct gtt gtc ttg ttc aat     1878
Tyr Tyr Glu Gln Thr Gly Val Gly Pro Leu Pro Val Val Leu Phe Asn
            600                 605                 610 ggg atg ccc ttt gaa aag gag cag tta gac ccc gac gag ctg gaa acc     1926
Gly Met Pro Phe Glu Lys Glu Gln Leu Asp Pro Asp Glu Leu Glu Thr
615                 620                 625 atc aca atg cac aag atc ttg gag acg acc acc ttc ttc caa aga gcc     1974
Ile Thr Met His Lys Ile Leu Glu Thr Thr Thr Phe Phe Gln Arg Ala
            630                 635                 640                 645 gtg tat ttg ggt gaa ctg tca cat gat caa gac gtg gta gag tac atc     2022
Val Tyr Leu Gly Glu Leu Ser His Asp Gln Asp Val Val Glu Tyr Ile
                650                 655                 660 atg aat cag ccg aat gtt gtt cca aga atc aac tct agg att ttg aca     2070
Met Asn Gln Pro Asn Val Val Pro Arg Ile Asn Ser Arg Ile Leu Thr
            665                 670                 675 gct aag cga gag tat ctg gat cta aca gca agc aat aat ttt tat gtg     2118
Ala Lys Arg Glu Tyr Leu Asp Leu Thr Ala Ser Asn Asn Phe Tyr Val
                680                 685                 690 gat gac ttt gcc aga ttt tct gcc ttg gac tct cgg ggc aag act gct     2166
Asp Asp Phe Ala Arg Phe Ser Ala Leu Asp Ser Arg Gly Lys Thr Ala
            695                 700                 705 gct att gcc aac agt atg aac tat ctg aca aaa aaa gga atg tcc tcc     2214
Ala Ile Ala Asn Ser Met Asn Tyr Leu Thr Lys Lys Gly Met Ser Ser
710                 715                 720                 725 aag gaa atc tat gat gat tcc ttt att agg cca gtg act ttt tgg att     2262
Lys Glu Ile Tyr Asp Asp Ser Phe Ile Arg Pro Val Thr Phe Trp Ile
            730                 735                 740 gtt gga gat ttt gat agc cct tct ggg cgg cag tta tta tat gac gcc     2310
Val Gly Asp Phe Asp Ser Pro Ser Gly Arg Gln Leu Leu Tyr Asp Ala
                745                 750                 755 att aaa cat cag aaa acc agt aac aat gtt agg ata agt atg atc aat     2358
Ile Lys His Gln Lys Thr Ser Asn Asn Val Arg Ile Ser Met Ile Asn
            760                 765                 770 aac ccc agc cga gag ata agt gac tca agc acc ccc gtc tcc aga gcc     2406
Asn Pro Ser Arg Glu Ile Ser Asp Ser Ser Thr Pro Val Ser Arg Ala
775                 780                 785 atc tgg gca gct ctc cag aca cag acc tcc aac tct gct aag aac ttc     2454
Ile Trp Ala Ala Leu Gln Thr Gln Thr Ser Asn Ser Ala Lys Asn Phe
790                 795                 800                 805 atc acc aag atg gtc aaa gag gag acg gca gag gcc ctg gcc gca gga     2502
Ile Thr Lys Met Val Lys Glu Glu Thr Ala Glu Ala Leu Ala Ala Gly
            810                 815                 820 gtg gac att ggg gaa ttc tct gtc ggg ggc atg gat gtc agt ctt ttt     2550
Val Asp Ile Gly Glu Phe Ser Val Gly Gly Met Asp Val Ser Leu Phe
                825                 830                 835 aaa gag gtc ttt gag tct tcc aga atg gat ttc att ttg tct cat gcc     2598
Lys Glu Val Phe Glu Ser Ser Arg Met Asp Phe Ile Leu Ser His Ala
            840                 845                 850 ctg tac tgc agg gat gtt ctg aaa ctg aag aag gga cag aga gtg gtg     2646
Leu Tyr Cys Arg Asp Val Leu Lys Leu Lys Lys Gly Gln Arg Val Val
855                 860                 865 atc agc aac gga agg atc att ggg cca ctg gag gac agt gag ctc ttc     2694
Ile Ser Asn Gly Arg Ile Ile Gly Pro Leu Glu Asp Ser Glu Leu Phe
```

-continued

```
          870                 875                 880                 885 aac caa gat gat ttc cac ctc ctg gaa aat atc att ctg aaa aca tcg         2742
Asn Gln Asp Asp Phe His Leu Leu Glu Asn Ile Ile Leu Lys Thr Ser
                    890                 895                 900 gga cag aaa atc aag tct cat atc caa cag ctt cgc gta gaa gaa gat         2790
Gly Gln Lys Ile Lys Ser His Ile Gln Gln Leu Arg Val Glu Glu Asp
            905                 910                 915 gtg gcc agt gat ttg gta atg aag gtg gat gct ctc ctg tca gcg caa         2838
Val Ala Ser Asp Leu Val Met Lys Val Asp Ala Leu Leu Ser Ala Gln
        920                 925                 930 ccc aaa gga gag gcg agg atc gag tac cag ttc ttt gaa gat aag cac         2886
Pro Lys Gly Glu Ala Arg Ile Glu Tyr Gln Phe Phe Glu Asp Lys His
    935                 940                 945 agt gca att aaa ctg aag ccc aaa gaa ggg gag aca tac tat gat gtg         2934
Ser Ala Ile Lys Leu Lys Pro Lys Glu Gly Glu Thr Tyr Tyr Asp Val
950                 955                 960                 965 gta gct gtt gtc gac cct gtc aca aga gaa gca cag agg ctc gcc ccc         2982
Val Ala Val Val Asp Pro Val Thr Arg Glu Ala Gln Arg Leu Ala Pro
                970                 975                 980 ttg ctc ttg gtt ttg gct cag ctg ata aac atg agt ctg aga gta ttc         3030
Leu Leu Leu Val Leu Ala Gln Leu Ile Asn Met Ser Leu Arg Val Phe
            985                 990                 995 atg aat tgc caa tcc aag ctt tcc gac atg cct tta aaa agc ttt tac         3078
Met Asn Cys Gln Ser Lys Leu Ser Asp Met Pro Leu Lys Ser Phe Tyr
        1000                1005                1010 cgt tat gtc tta gag ccg gag att tct ttc act gca gac aac agc ttt         3126
Arg Tyr Val Leu Glu Pro Glu Ile Ser Phe Thr Ala Asp Asn Ser Phe
    1015                1020                1025 gcc aag gga cca ata gca aag ttt ctg gat atg cct cag tct ccg ctg         3174
Ala Lys Gly Pro Ile Ala Lys Phe Leu Asp Met Pro Gln Ser Pro Leu
1030                1035                1040                1045 ttt act ttg aat ttg aac aca ccc gag agt tgg atg gta gaa tct gtc         3222
Phe Thr Leu Asn Leu Asn Thr Pro Glu Ser Trp Met Val Glu Ser Val
                1050                1055                1060 aga aca ccc tat gat ctt gat aat att tac cta gaa gag gtg gac agt         3270
Arg Thr Pro Tyr Asp Leu Asp Asn Ile Tyr Leu Glu Glu Val Asp Ser
            1065                1070                1075 ata gtg gct gct gag tat gag ctg gag tat ctg tta ctg gaa ggt cat         3318
Ile Val Ala Ala Glu Tyr Glu Leu Glu Tyr Leu Leu Leu Glu Gly His
        1080                1085                1090 tgt tac gac atc acc aca ggc cag ccc cct cga gga ctg cag ttc acg         3366
Cys Tyr Asp Ile Thr Thr Gly Gln Pro Pro Arg Gly Leu Gln Phe Thr
    1095                1100                1105 tta gga act tca gcc aac cca aca act gtg gac aca atc gtg atg gcc         3414
Leu Gly Thr Ser Ala Asn Pro Thr Thr Val Asp Thr Ile Val Met Ala
1110                1115                1120                1125 aat ctg gga tat ttt cag ctc aaa gcc aac cca gga gcc tgg att ctg         3462
Asn Leu Gly Tyr Phe Gln Leu Lys Ala Asn Pro Gly Ala Trp Ile Leu
                1130                1135                1140 aga ctg agg aag ggg cgc tcg gat gac att tat agg atc tac agc cat         3510
Arg Leu Arg Lys Gly Arg Ser Asp Asp Ile Tyr Arg Ile Tyr Ser His
            1145                1150                1155 gac gga aca gat tcc cct cct gat gca aat gac gtt gtt gtc atc ctc         3558
Asp Gly Thr Asp Ser Pro Pro Asp Ala Asn Asp Val Val Val Ile Leu
        1160                1165                1170 aat aac ttc aag agc aag atc atc aaa gtg aag gtt cag aag aag gcc         3606
Asn Asn Phe Lys Ser Lys Ile Ile Lys Val Lys Val Gln Lys Lys Ala
    1175                1180                1185 gac atg gct aat gaa gac ttg ctg agc gac ggg acg aat gag aat gag         3654
```

```
                                                          -continued

Asp Met Ala Asn Glu Asp Leu Leu Ser Asp Gly Thr Asn Glu Asn Glu
1190                1195                1200                1205 tct gga ttc tgg gac tca ttc aag tgg ggc ttc tca gga cag aag act       3702
Ser Gly Phe Trp Asp Ser Phe Lys Trp Gly Phe Ser Gly Gln Lys Thr
                    1210                1215                1220 gag gaa gta aag caa gat aag gac gac ata atc aat att ttc tct gtt       3750
Glu Glu Val Lys Gln Asp Lys Asp Asp Ile Ile Asn Ile Phe Ser Val
            1225                1230                1235 gca tct ggt cat ctc tac gaa agg ttt ctt cgc atc atg atg cta tca       3798
Ala Ser Gly His Leu Tyr Glu Arg Phe Leu Arg Ile Met Met Leu Ser
        1240                1245                1250 gtc ctg aag aat acc aaa act cct gtg aaa ttc tgg ttc ttg aag aat       3846
Val Leu Lys Asn Thr Lys Thr Pro Val Lys Phe Trp Phe Leu Lys Asn
    1255                1260                1265 tat ttg tcc ccc aca ttt aag gag ttt ata cct tac atg gcc aaa aaa       3894
Tyr Leu Ser Pro Thr Phe Lys Glu Phe Ile Pro Tyr Met Ala Lys Lys
1270                1275                1280                1285 tac aat ttc cag tat gag ctt gtt cag tac aaa tgg cca cgg tgg ctt       3942
Tyr Asn Phe Gln Tyr Glu Leu Val Gln Tyr Lys Trp Pro Arg Trp Leu
                1290                1295                1300 cac cag cag acc gag aag cag cga att atc tgg ggc tac aag atc ctc       3990
His Gln Gln Thr Glu Lys Gln Arg Ile Ile Trp Gly Tyr Lys Ile Leu
            1305                1310                1315 ttc ctg gat gtg ctt ttc ccg ttg gtt gtt gac aaa ttc ctc ttt gtg       4038
Phe Leu Asp Val Leu Phe Pro Leu Val Val Asp Lys Phe Leu Phe Val
        1320                1325                1330 gat gct gat cag att gtg cgg aca gat ctg aag gag tta aga gat ttc       4086
Asp Ala Asp Gln Ile Val Arg Thr Asp Leu Lys Glu Leu Arg Asp Phe
    1335                1340                1345 aat ttg gat ggt gca cct tac ggt tac acg ccc ttc tgc gac agc agg       4134
Asn Leu Asp Gly Ala Pro Tyr Gly Tyr Thr Pro Phe Cys Asp Ser Arg
1350                1355                1360                1365 aga gag atg gat ggc tac cgc ttc tgg aag tca ggc tac tgg gcc agt       4182
Arg Glu Met Asp Gly Tyr Arg Phe Trp Lys Ser Gly Tyr Trp Ala Ser
                1370                1375                1380 cat ttg gct gga cga aag tat cac atc agt gcg ctg tat gtc gtg gat       4230
His Leu Ala Gly Arg Lys Tyr His Ile Ser Ala Leu Tyr Val Val Asp
            1385                1390                1395 ctg aag aag ttt agg aaa ata gct gct ggt gac aga ctc aga gga cag       4278
Leu Lys Lys Phe Arg Lys Ile Ala Ala Gly Asp Arg Leu Arg Gly Gln
        1400                1405                1410 tac caa ggt ctg agt cag gat ccc aac agt ctt tca aat ctt gat caa       4326
Tyr Gln Gly Leu Ser Gln Asp Pro Asn Ser Leu Ser Asn Leu Asp Gln
    1415                1420                1425 gat ttg ccc aat aac atg atc cat cag gtg cca atc aaa tcg ctc cct       4374
Asp Leu Pro Asn Asn Met Ile His Gln Val Pro Ile Lys Ser Leu Pro
1430                1435                1440                1445 cag gag tgg ctt tgg tgt gag acg tgg tgt gat gat gcc tct aag aag       4422
Gln Glu Trp Leu Trp Cys Glu Thr Trp Cys Asp Asp Ala Ser Lys Lys
                1450                1455                1460 cgg gcc aag acc atc gac ctg tgt aat aat ccc atg act aag gag ccc       4470
Arg Ala Lys Thr Ile Asp Leu Cys Asn Asn Pro Met Thr Lys Glu Pro
            1465                1470                1475 aaa ctg gag gct gct gtg cgg atc gtc cct gag tgg caa gac tac gac       4518
Lys Leu Glu Ala Ala Val Arg Ile Val Pro Glu Trp Gln Asp Tyr Asp
        1480                1485                1490 cag gag atc aag cag ttg cag acc ctc ttc caa gag gag aaa gag ttg       4566
Gln Glu Ile Lys Gln Leu Gln Thr Leu Phe Gln Glu Glu Lys Glu Leu
    1495                1500                1505
```

-continued

```
ggg acc ctg cat gaa gag gag aca cag gaa gga tct cag aag cat gaa    4614
Gly Thr Leu His Glu Glu Glu Thr Gln Glu Gly Ser Gln Lys His Glu
1510            1515                1520                1525 gaa tta tga tctctggagg aagataggg acccacgtct gacagttttg             4663
Glu Leu tactaaatgc tgtttctttc tgatcttttg aaacaactgc tgatgaactg actgattggg  4723
caggtgtatc acacctattg atctgagcat ttgattagac tactgcaccc tagtgggtgc  4783
tagatccttg gggctaaggc tctgttggat ttgtacctca gaggaagaca agtgaccgat  4843
cttctgggac tctcttctcg ccagagggaa ctgaaagaag cccagtcttc ggtgcccaca  4903
tcccagagca cacattgttg tgctggtcca ggagctggcc agaaaggtca ccatgctctt  4963
ccttacctca gtttacctgc agccctcgct gcagtgcaga tgcccacctg taccaggtca  5023
ggccggcaga tgcttcatcc atgcctcgag                                   5053
```

<210> SEQ ID NO 2
<211> LENGTH: 1527
<212> TYPE: PRT
<213> ORGANISM: Rat RUGT

<400> SEQUENCE: 2

```
Met Gly Leu Leu Ile Ala Leu Ala Leu Leu Cys Leu Phe Ser Leu Ala
 1               5                  10                  15

Glu Ala Asn Ser Lys Ala Ile Thr Thr Ser Leu Thr Thr Lys Trp Phe
            20                  25                  30

Ser Ala Pro Leu Leu Leu Glu Ala Ser Glu Phe Leu Ala Glu Asp Ser
        35                  40                  45

Gln Glu Lys Phe Trp Ser Phe Val Glu Ala Ser Gln Asn Ile Gly Ser
    50                  55                  60

Ser Asp Gln His Asp Thr Asp Arg Ser Tyr Tyr Asp Ala Ile Leu Glu
65                  70                  75                  80

Ala Ala Phe Arg Phe Leu Ser Pro Leu Gln Gln Asn Leu Leu Lys Phe
                85                  90                  95

Cys Leu Ser Leu Arg Ser Tyr Ser Ala Ser Ile Gln Ala Phe Gln Gln
            100                 105                 110

Ile Ala Val Asp Glu Pro Pro Glu Gly Cys Lys Ser Phe Leu Ser
        115                 120                 125

Val His Gly Lys Gln Thr Cys Asp Leu Gly Thr Leu Glu Ser Leu Leu
    130                 135                 140

Leu Thr Ala Pro Asp Arg Pro Lys Pro Leu Phe Lys Gly Asp His
145                 150                 155                 160

Arg Tyr Pro Ser Ser Asn Pro Glu Ser Pro Val Val Ile Phe Tyr Ser
                165                 170                 175

Glu Ile Gly His Glu Glu Phe Ser Asn Ile His His Gln Leu Ile Ser
            180                 185                 190

Lys Ser Asn Glu Gly Lys Ile Asn Tyr Val Phe Arg His Tyr Ile Ser
        195                 200                 205

Asn Pro Arg Lys Glu Pro Val His Leu Ser Gly Tyr Gly Val Glu Leu
    210                 215                 220

Ala Ile Lys Ser Thr Glu Tyr Lys Ala Lys Asp Asp Thr Gln Val Lys
225                 230                 235                 240

Gly Thr Glu Val Asn Thr Thr Val Ile Gly Glu Asn Asp Pro Ile Asp
                245                 250                 255

Glu Val Gln Gly Phe Leu Phe Gly Lys Leu Arg Glu Leu Tyr Pro Ser
            260                 265                 270
```

-continued

```
Leu Glu Gly Gln Leu Lys Glu Phe Arg Lys His Leu Val Glu Ser Thr
            275                 280                 285

Asn Glu Met Ala Pro Leu Lys Val Trp Gln Leu Gln Asp Leu Ser Phe
    290                 295                 300

Gln Thr Ala Ala Arg Ile Leu Ala Ala Pro Val Glu Leu Ala Leu Val
305                 310                 315                 320

Val Met Lys Asp Ile Ser Gln Asn Phe Pro Thr Lys Ala Arg Ala Ile
                325                 330                 335

Thr Lys Thr Ala Val Ser Ala Gln Leu Arg Ala Glu Val Glu Glu Asn
            340                 345                 350

Gln Lys Tyr Phe Lys Gly Thr Ile Gly Leu Gln Pro Gly Asp Ser Ala
            355                 360                 365

Leu Phe Ile Asn Gly Leu His Ile Asp Leu Asp Thr Gln Asp Ile Phe
    370                 375                 380

Ser Leu Phe Asp Thr Leu Arg Asn Glu Ala Arg Val Met Glu Gly Leu
385                 390                 395                 400

His Arg Leu Gly Ile Glu Gly Leu Ser Leu His Asn Ile Leu Lys Leu
                405                 410                 415

Asn Ile Gln Pro Ser Glu Thr Asp Tyr Ala Val Asp Ile Arg Ser Pro
            420                 425                 430

Ala Ile Ser Trp Val Asn Asn Leu Glu Val Asp Ser Arg Tyr Asn Ser
            435                 440                 445

Trp Pro Ser Ser Leu Gln Glu Leu Leu Arg Pro Thr Phe Pro Gly Val
    450                 455                 460

Ile Arg Gln Ile Arg Lys Asn Leu His Asn Met Val Phe Ile Val Asp
465                 470                 475                 480

Pro Val His Glu Thr Thr Ala Glu Leu Val Ser Ile Ala Glu Met Phe
                485                 490                 495

Leu Ser Asn His Ile Pro Leu Arg Ile Gly Phe Ile Phe Val Val Asn
            500                 505                 510

Asp Ser Glu Asp Val Asp Gly Met Gln Asp Ala Gly Val Ala Val Leu
            515                 520                 525

Arg Ala Tyr Asn Tyr Val Gly Gln Glu Val Asp Gly Tyr His Ala Phe
    530                 535                 540

Gln Thr Leu Thr Gln Ile Tyr Asn Lys Val Arg Thr Gly Glu Lys Val
545                 550                 555                 560

Lys Val Glu His Val Val Ser Val Leu Glu Lys Tyr Pro Tyr Val
                565                 570                 575

Glu Val Asn Ser Ile Leu Gly Ile Asp Ser Ala Tyr Asp Gln Asn Arg
            580                 585                 590

Lys Glu Ala Arg Gly Tyr Tyr Glu Gln Thr Gly Val Gly Pro Leu Pro
            595                 600                 605

Val Val Leu Phe Asn Gly Met Pro Phe Glu Lys Glu Gln Leu Asp Pro
    610                 615                 620

Asp Glu Leu Glu Thr Ile Thr Met His Lys Ile Leu Glu Thr Thr Thr
625                 630                 635                 640

Phe Phe Gln Arg Ala Val Tyr Leu Gly Glu Leu Ser His Asp Gln Asp
                645                 650                 655

Val Val Glu Tyr Ile Met Asn Gln Pro Asn Val Val Pro Arg Ile Asn
            660                 665                 670

Ser Arg Ile Leu Thr Ala Lys Arg Glu Tyr Leu Asp Leu Thr Ala Ser
            675                 680                 685
```

-continued

```
Asn Asn Phe Tyr Val Asp Asp Phe Ala Arg Phe Ser Ala Leu Asp Ser
    690                 695                 700

Arg Gly Lys Thr Ala Ala Ile Ala Asn Ser Met Asn Tyr Leu Thr Lys
705                 710                 715                 720

Lys Gly Met Ser Ser Lys Glu Ile Tyr Asp Asp Ser Phe Ile Arg Pro
                725                 730                 735

Val Thr Phe Trp Ile Val Gly Asp Phe Asp Ser Pro Ser Gly Arg Gln
            740                 745                 750

Leu Leu Tyr Asp Ala Ile Lys His Gln Lys Thr Ser Asn Asn Val Arg
        755                 760                 765

Ile Ser Met Ile Asn Asn Pro Ser Arg Glu Ile Ser Asp Ser Ser Thr
    770                 775                 780

Pro Val Ser Arg Ala Ile Trp Ala Ala Leu Gln Thr Gln Thr Ser Asn
785                 790                 795                 800

Ser Ala Lys Asn Phe Ile Thr Lys Met Val Lys Glu Thr Ala Glu
                805                 810                 815

Ala Leu Ala Ala Gly Val Asp Ile Gly Glu Phe Ser Val Gly Gly Met
            820                 825                 830

Asp Val Ser Leu Phe Lys Glu Val Phe Glu Ser Ser Arg Met Asp Phe
        835                 840                 845

Ile Leu Ser His Ala Leu Tyr Cys Arg Asp Val Leu Lys Leu Lys Lys
    850                 855                 860

Gly Gln Arg Val Val Ile Ser Asn Gly Arg Ile Ile Gly Pro Leu Glu
865                 870                 875                 880

Asp Ser Glu Leu Phe Asn Gln Asp Asp Phe His Leu Leu Glu Asn Ile
                885                 890                 895

Ile Leu Lys Thr Ser Gly Gln Lys Ile Lys Ser His Ile Gln Gln Leu
            900                 905                 910

Arg Val Glu Glu Asp Val Ala Ser Asp Leu Val Met Lys Val Asp Ala
        915                 920                 925

Leu Leu Ser Ala Gln Pro Lys Gly Glu Ala Arg Ile Glu Tyr Gln Phe
    930                 935                 940

Phe Glu Asp Lys His Ser Ala Ile Lys Leu Lys Pro Lys Glu Gly Glu
945                 950                 955                 960

Thr Tyr Tyr Asp Val Val Ala Val Val Asp Pro Val Thr Arg Glu Ala
                965                 970                 975

Gln Arg Leu Ala Pro Leu Leu Leu Val Leu Ala Gln Leu Ile Asn Met
            980                 985                 990

Ser Leu Arg Val Phe Met Asn Cys Gln Ser Lys Leu Ser Asp Met Pro
        995                 1000                1005

Leu Lys Ser Phe Tyr Arg Tyr Val Leu Glu Pro Glu Ile Ser Phe Thr
    1010                1015                1020

Ala Asp Asn Ser Phe Ala Lys Gly Pro Ile Ala Lys Phe Leu Asp Met
1025                1030                1035                1040

Pro Gln Ser Pro Leu Phe Thr Leu Asn Leu Asn Thr Pro Glu Ser Trp
                1045                1050                1055

Met Val Glu Ser Val Arg Thr Pro Tyr Asp Leu Asp Asn Ile Tyr Leu
            1060                1065                1070

Glu Glu Val Asp Ser Ile Val Ala Ala Glu Tyr Glu Leu Glu Tyr Leu
        1075                1080                1085

Leu Leu Glu Gly His Cys Tyr Asp Ile Thr Thr Gly Gln Pro Pro Arg
    1090                1095                1100

Gly Leu Gln Phe Thr Leu Gly Thr Ser Ala Asn Pro Thr Thr Val Asp
```

-continued

```
      1105              1110             1115              1120
Thr Ile Val Met Ala Asn Leu Gly Tyr Phe Gln Leu Lys Ala Asn Pro
              1125              1130              1135
Gly Ala Trp Ile Leu Arg Leu Arg Lys Gly Arg Ser Asp Asp Ile Tyr
              1140              1145              1150
Arg Ile Tyr Ser His Asp Gly Thr Asp Ser Pro Pro Asp Ala Asn Asp
              1155              1160              1165
Val Val Val Ile Leu Asn Asn Phe Lys Ser Lys Ile Ile Lys Val Lys
      1170              1175              1180
Val Gln Lys Lys Ala Asp Met Ala Asn Glu Asp Leu Leu Ser Asp Gly
1185              1190              1195              1200
Thr Asn Glu Asn Glu Ser Gly Phe Trp Asp Ser Phe Lys Trp Gly Phe
              1205              1210              1215
Ser Gly Gln Lys Thr Glu Glu Val Lys Gln Asp Lys Asp Asp Ile Ile
              1220              1225              1230
Asn Ile Phe Ser Val Ala Ser Gly His Leu Tyr Glu Arg Phe Leu Arg
              1235              1240              1245
Ile Met Met Leu Ser Val Leu Lys Asn Thr Lys Thr Pro Val Lys Phe
      1250              1255              1260
Trp Phe Leu Lys Asn Tyr Leu Ser Pro Thr Phe Lys Glu Phe Ile Pro
1265              1270              1275              1280
Tyr Met Ala Lys Lys Tyr Asn Phe Gln Tyr Glu Leu Val Gln Tyr Lys
              1285              1290              1295
Trp Pro Arg Trp Leu His Gln Gln Thr Glu Lys Gln Arg Ile Ile Trp
              1300              1305              1310
Gly Tyr Lys Ile Leu Phe Leu Asp Val Leu Phe Pro Leu Val Val Asp
              1315              1320              1325
Lys Phe Leu Phe Val Asp Ala Asp Gln Ile Val Arg Thr Asp Leu Lys
      1330              1335              1340
Glu Leu Arg Asp Phe Asn Leu Asp Gly Ala Pro Tyr Gly Tyr Thr Pro
1345              1350              1355              1360
Phe Cys Asp Ser Arg Arg Glu Met Asp Gly Tyr Arg Phe Trp Lys Ser
              1365              1370              1375
Gly Tyr Trp Ala Ser His Leu Ala Gly Arg Lys Tyr His Ile Ser Ala
              1380              1385              1390
Leu Tyr Val Val Asp Leu Lys Lys Phe Arg Lys Ile Ala Ala Gly Asp
              1395              1400              1405
Arg Leu Arg Gly Gln Tyr Gln Gly Leu Ser Gln Asp Pro Asn Ser Leu
      1410              1415              1420
Ser Asn Leu Asp Gln Asp Leu Pro Asn Asn Met Ile His Gln Val Pro
1425              1430              1435              1440
Ile Lys Ser Leu Pro Gln Glu Trp Leu Trp Cys Glu Thr Trp Cys Asp
              1445              1450              1455
Asp Ala Ser Lys Lys Arg Ala Lys Thr Ile Asp Leu Cys Asn Asn Pro
              1460              1465              1470
Met Thr Lys Glu Pro Lys Leu Glu Ala Ala Val Arg Ile Val Pro Glu
              1475              1480              1485
Trp Gln Asp Tyr Asp Gln Glu Ile Lys Gln Leu Gln Thr Leu Phe Gln
              1490              1495              1500
Glu Glu Lys Glu Leu Gly Thr Leu His Glu Glu Thr Gln Glu Gly
1505              1510              1515              1520
Ser Gln Lys His Glu Glu Leu
              1525
```

```
<210> SEQ ID NO 3
<211> LENGTH: 76
<212> TYPE: DNA
<213> ORGANISM: Melittin Signal Peptide sequence
<220> FEATURE:
<221> NAME/KEY: CDS
<222> LOCATION: (14)...(76)
<221> NAME/KEY: misc_feature
<222> LOCATION: (1)...(7)
<223> OTHER INFORMATION: Rsr II restriction site
<220> FEATURE:
<221> NAME/KEY: misc_feature
<222> LOCATION: (37)...(42)
<223> OTHER INFORMATION: Spe  restriction siteI

<400> SEQUENCE: 3
cggtccgcac aag atg aaa ttc tta gtc aac gtt gca cta gtt ttt atg         49
            Met Lys Phe Leu Val Asn Val Ala Leu Val Phe Met
              1               5                  10 gtc gtg tac att tct tac atc tat gcg                                    76
Val Val Tyr Ile Ser Tyr Ile Tyr Ala
         15                  20

<210> SEQ ID NO 4
<211> LENGTH: 21
<212> TYPE: PRT
<213> ORGANISM: Melittin Signal Peptide sequence

<400> SEQUENCE: 4

Met Lys Phe Leu Val Asn Val Ala Leu Val Phe Met Val Val Tyr Ile
  1               5                  10                  15

Ser Tyr Ile Tyr Ala
             20

<210> SEQ ID NO 5
<211> LENGTH: 48
<212> TYPE: DNA
<213> ORGANISM: C-terminal (His)6 tag
<220> FEATURE:
<221> NAME/KEY: CDS
<222> LOCATION: (1)...(36)
<221> NAME/KEY: misc_feature
<222> LOCATION: (43)...(48)
<223> OTHER INFORMATION: Kpn I restriction site

<400> SEQUENCE: 5 cag gaa gga tct cag aag cat cac cat cac cat cac tgataaggta             46
Gln Glu Gly Ser Gln Lys His His His His His His
  1               5                  10 cc                                                                     48

<210> SEQ ID NO 6
<211> LENGTH: 12
<212> TYPE: PRT
<213> ORGANISM: C-terminal (His)6 tag

<400> SEQUENCE: 6

Gln Glu Gly Ser Gln Lys His His His His His His
  1               5                  10

<210> SEQ ID NO 7
<211> LENGTH: 57
<212> TYPE: DNA
<213> ORGANISM: Mutant D1334A RUGT
<220> FEATURE:
<221> NAME/KEY: CDS
```

```
<222> LOCATION: (1)...(57)
<221> NAME/KEY: misc_feature
<222> LOCATION: (32)...(37)
<223> OTHER INFORMATION: Pst I restriction site

<400> SEQUENCE: 7 ccg ttg gtt gtt gac aaa ttc ctc ttt gtg gct gca gat cag att gtg      48
Pro Leu Val Val Asp Lys Phe Leu Phe Val Ala Ala Asp Gln Ile Val
 1               5                  10                  15 cgg aca gat                                                          57
Arg Thr Asp <210> SEQ ID NO 8
<211> LENGTH: 19
<212> TYPE: PRT
<213> ORGANISM: Mutant D1334A RUGT

<400> SEQUENCE: 8

Pro Leu Val Val Asp Lys Phe Leu Phe Val Ala Ala Asp Gln Ile Val
 1               5                  10                  15

Arg Thr Asp

<210> SEQ ID NO 9
<211> LENGTH: 57
<212> TYPE: DNA
<213> ORGANISM: Mutant D1336A RUGT
<220> FEATURE:
<221> NAME/KEY: CDS
<222> LOCATION: (1)...(57)
<221> NAME/KEY: misc_feature
<222> LOCATION: (35)...(40)
<223> OTHER INFORMATION: BsrBI restriction site

<400> SEQUENCE: 9 ccg ttg gtt gtt gac aaa ttc ctc ttt gtg gat gcc gct cag att gtg      48
Pro Leu Val Val Asp Lys Phe Leu Phe Val Asp Ala Ala Gln Ile Val
 1               5                  10                  15 cgg aca gat                                                          57
Arg Thr Asp <210> SEQ ID NO 10
<211> LENGTH: 19
<212> TYPE: PRT
<213> ORGANISM: Mutant D1336A RUGT

<400> SEQUENCE: 10

Pro Leu Val Val Asp Lys Phe Leu Phe Val Asp Ala Ala Gln Ile Val
 1               5                  10                  15

Arg Thr Asp

<210> SEQ ID NO 11
<211> LENGTH: 57
<212> TYPE: DNA
<213> ORGANISM: Mutant Q1429A RUGT
<220> FEATURE:
<221> NAME/KEY: CDS
<222> LOCATION: (1)...(57)
<221> NAME/KEY: misc_feature
<222> LOCATION: (3)...(8)
<223> OTHER INFORMATION: BamHI restriction site
<220> FEATURE:
<221> NAME/KEY: misc_feature
<222> LOCATION: (24)...(29)
<223> OTHER INFORMATION: Xba I restriction site

<400> SEQUENCE: 11
```

```
cag gat ccc aac agt ctt tca aat cta gat gca gat ttg ccc aat aac    48
Gln Asp Pro Asn Ser Leu Ser Asn Leu Asp Ala Asp Leu Pro Asn Asn
  1               5                  10                  15 atg atc cat                                                        57
Met Ile His
```

<210> SEQ ID NO 12
<211> LENGTH: 19
<212> TYPE: PRT
<213> ORGANISM: Mutant Q1429A RUGT

<400> SEQUENCE: 12

```
Gln Asp Pro Asn Ser Leu Ser Asn Leu Asp Ala Asp Leu Pro Asn Asn
  1               5                  10                  15

Met Ile His
```

<210> SEQ ID NO 13
<211> LENGTH: 57
<212> TYPE: DNA
<213> ORGANISM: Mutant N1433A RUGT
<220> FEATURE:
<221> NAME/KEY: CDS
<222> LOCATION: (1)...(57)
<221> NAME/KEY: misc_feature
<222> LOCATION: (3)...(8)
<223> OTHER INFORMATION: Bam HI restriction Site
<220> FEATURE:
<221> NAME/KEY: misc_feature
<222> LOCATION: (39)...(44)
<223> OTHER INFORMATION: Nae I restriction site

<400> SEQUENCE: 13

```
cag gat ccc aac agt ctt tca aat ctt gat caa gat ttg ccg gct aac    48
Gln Asp Pro Asn Ser Leu Ser Asn Leu Asp Gln Asp Leu Pro Ala Asn
  1               5                  10                  15 atg atc cat                                                        57
Met Ile His
```

<210> SEQ ID NO 14
<211> LENGTH: 19
<212> TYPE: PRT
<213> ORGANISM: Mutant N1433A RUGT

<400> SEQUENCE: 14

```
Gln Asp Pro Asn Ser Leu Ser Asn Leu Asp Gln Asp Leu Pro Ala Asn
  1               5                  10                  15

Met Ile His
```

<210> SEQ ID NO 15
<211> LENGTH: 1548
<212> TYPE: PRT
<213> ORGANISM: Artificial Sequence
<220> FEATURE:
<223> OTHER INFORMATION: D. melanogaster UGGT

<400> SEQUENCE: 15

```
Met Leu Arg Ala Val Ala Leu Cys Val Ser Val Val Leu Ile Ala Leu
  1               5                  10                  15

Tyr Thr Pro Thr Ser Gly Glu Ser Ser Gln Ser Tyr Pro Ile Thr Thr
                 20                  25                  30

Leu Ile Asn Ala Lys Trp Thr Gln Thr Pro Leu Tyr Leu Glu Ile Ala
             35                  40                  45

Glu Tyr Leu Ala Asp Glu Gln Ala Gly Leu Phe Trp Asp Tyr Val Ser
         50                  55                  60
```

-continued

```
Gly Val Thr Lys Leu Asp Thr Val Leu Asn Glu Tyr Asp Thr Glu Ser
 65                  70                  75                  80

Gln Gln Tyr Asn Ala Ala Leu Glu Leu Val Lys Ser His Val Ser Ser
                 85                  90                  95

Pro Gln Leu Pro Leu Leu Arg Leu Val Val Ser Met His Ser Leu Thr
            100                 105                 110

Pro Arg Ile Gln Thr His Phe Gln Leu Ala Glu Glu Leu Arg Ser Ser
            115                 120                 125

Gly Ser Cys Gln Ser Phe Thr Phe Ala Gln Val Gly Ser Glu Leu Ala
        130                 135                 140

Cys Ser Phe Asn Glu Leu Gln Lys Lys Leu Glu Val Pro Leu Ala Lys
145                 150                 155                 160

Asp Ser Leu Asp Ala Pro Val Val Thr Tyr Ser Phe Asp His Ile Phe
                165                 170                 175

Pro Gly Ser Glu Asn Asn Thr Arg Thr Val Val Leu Tyr Gly Asp Leu
            180                 185                 190

Gly Ser Ser Gln Phe Arg Thr Tyr His Lys Leu Leu Glu Lys Glu Ala
        195                 200                 205

Asn Ala Gly Arg Ile Arg Tyr Ile Leu Arg His Gln Leu Ala Lys Lys
210                 215                 220

Asp Lys Arg Pro Val Arg Leu Ser Gly Tyr Gly Val Glu Leu His Leu
225                 230                 235                 240

Lys Ser Thr Glu Tyr Lys Ser Gln Asp Asp Ala Pro Lys Pro Glu Ala
                245                 250                 255

Gly Ser Thr Ser Asp Glu Asp Leu Ala Asn Glu Ser Asp Val Gln Gly
            260                 265                 270

Phe Asp Phe Lys Val Leu Lys Gln Lys His Pro Thr Leu Lys Arg Ala
        275                 280                 285

Leu Asp Gln Leu Arg Gln Arg Leu Leu Gln Gly Asn Asp Glu Ile Ala
        290                 295                 300

Gln Leu Lys Ala Trp Glu Phe Gln Asp Leu Gly Leu Gln Ala Ala Ala
305                 310                 315                 320

Ala Ile Ala Glu Ile Gln Gly Asp Glu Thr Leu Gln Ile Leu Gln Tyr
                325                 330                 335

Thr Ala His Asn Phe Pro Met Leu Ala Arg Thr Leu Leu Ala His Lys
            340                 345                 350

Val Thr Asp Gly Leu Arg Ala Glu Val Lys His Asn Thr Glu Ala Phe
        355                 360                 365

Gly Arg Ser Leu Asn Val Ala Pro Pro Asp Gly Ala Leu Phe Ile Asn
370                 375                 380

Gly Leu Phe Phe Asp Ala Asp Thr Met Asp Leu Tyr Ser Leu Ile Glu
385                 390                 395                 400

Thr Leu Arg Ser Glu Met Arg Val Leu Glu Ser Leu His Ser Asn Asn
                405                 410                 415

Val Arg Gly Ser Leu Ala Ser Ser Leu Leu Ala Leu Asp Leu Thr Ala
            420                 425                 430

Ser Ser Lys Lys Glu Phe Ala Ile Asp Ile Arg Asp Thr Ala Val Gln
        435                 440                 445

Trp Val Asn Asp Ile Glu Asn Asp Val Gln Tyr Arg Arg Trp Pro Ser
450                 455                 460

Ser Val Met Asp Leu Leu Arg Pro Thr Phe Pro Gly Met Leu Arg Asn
465                 470                 475                 480
```

-continued

```
Ile Arg Lys Asn Val Phe Asn Leu Val Leu Val Val Asp Ala Leu Gln
            485                 490                 495
Pro Thr Ala Arg Ser Val Ile Lys Leu Ser Glu Ser Phe Val Ile His
            500                 505                 510
Gln Ala Pro Ile Arg Leu Gly Leu Val Phe Asp Ala Arg Asp Ala Asn
            515                 520                 525
Glu Asp Asn Leu Ala Asp Tyr Val Ala Ile Thr Cys Ala Tyr Asn Tyr
            530                 535                 540
Val Ser Gln Lys Lys Asp Ala Arg Ala Ala Leu Ser Phe Leu Thr Asp
545                 550                 555                 560
Ile Tyr Ala Ala Val Gly Glu Thr Lys Val Val Thr Lys Lys Asp Ile
            565                 570                 575
Val Lys Gln Leu Thr Lys Glu Phe Thr Ser Leu Ser Phe Ala Lys Ala
            580                 585                 590
Glu Glu Phe Leu Glu Glu Asp Ser Thr Tyr Asp Tyr Gly Arg Glu Leu
            595                 600                 605
Ala Ala Glu Phe Ile Gln Arg Leu Gly Phe Gly Asp Lys Glu Gln Pro
            610                 615                 620
Gln Ala Leu Leu Asn Gly Val Pro Met Pro Ser Asn Val Val Thr Ala
625                 630                 635                 640
Asp Ser Asp Phe Glu Glu Ala Ile Phe Thr Glu Ile Met Thr His Thr
            645                 650                 655
Ser Asn Leu Gln Lys Ala Val Tyr Lys Gly Glu Leu Thr Asp Asn Asp
            660                 665                 670
Val Ala Ile Asp Tyr Leu Met Asn Gln Pro His Val Met Pro Arg Leu
            675                 680                 685
Asn Gln Arg Ile Leu Ser Gln Glu Asp Val Lys Tyr Leu Asp Ile Asn
690                 695                 700
Gly Val Ala Tyr Lys Asn Leu Gly Asn Val Gly Val Leu Asn Arg Leu
705                 710                 715                 720
Ser Asn Arg Asp Met Thr Ala Thr Leu Met Asp Asn Leu Lys Tyr Phe
            725                 730                 735
Gly Gly Lys Lys Ser Thr Glu Leu Ile Gly Arg Thr Ser Leu Gln Phe
            740                 745                 750
Leu Thr Ile Trp Val Phe Ala Asp Leu Glu Thr Asp Gln Gly Arg Asp
            755                 760                 765
Leu Leu Thr His Ala Leu Asp Tyr Val Gln Ser Gly Glu Ser Val Arg
            770                 775                 780
Val Ala Phe Ile Pro Asn Thr Glu Ser Ser Ala Ser Ser Arg Arg
785                 790                 795                 800
Asn Leu Asn Arg Leu Val Trp Ala Ala Met Gln Ser Leu Pro Pro Thr
            805                 810                 815
Gln Ala Thr Glu Gln Val Leu Lys Trp Leu Lys Pro Lys Glu Lys
            820                 825                 830
Ile Glu Ile Pro Thr Gln Leu Glu Asp Ile Leu Gly Ser Thr Glu Leu
            835                 840                 845
His Leu Lys Met Leu Arg Val Tyr Ser Gln Arg Val Leu Gly Leu Asn
            850                 855                 860
Lys Ser Gln Arg Leu Val Ile Gly Asn Gly Arg Leu Tyr Gly Pro Leu
865                 870                 875                 880
Ser Ser Asp Glu Ser Phe Asp Ser Ala Asp Phe Ala Leu Leu Ala Arg
            885                 890                 895
Phe Ser Ser Leu Gln Tyr Ser Asp Lys Val Arg Gln Val Leu Lys Glu
```

-continued

```
              900             905             910
Ser Ala Gln Asp Val Asn Glu Glu Phe Asn Ser Asp Thr Leu Leu Lys
        915                 920             925

Leu Tyr Ala Ser Leu Leu Pro Arg Gln Thr Lys Thr Arg Phe Lys Leu
    930                 935             940

Pro Thr Asp Leu Lys Thr Asp His Ser Val Val Lys Leu Pro Pro Lys
945                 950             955                 960

Gln Glu Lys Leu Pro His Phe Asp Val Ala Ala Val Leu Asp Pro Ala
                965             970             975

Ser Arg Ala Ala Gln Lys Leu Thr Pro Ile Leu Ile Leu Leu Pro Gln
            980             985             990

Val Leu Asn Cys Gln Leu Asn Leu Tyr Leu Ile Pro Val Pro Gln His
        995             1000            1005

Ser Asp Met Pro Val Lys Asn Phe Tyr Arg Tyr Val Glu Pro Glu
    1010            1015            1020

Val Gln Phe Glu Ala Asn Gly Gly Arg Ser Asp Gly Pro Leu Ala Lys
1025                1030            1035            1040

Phe Ser Gly Leu Pro Ala Asn Pro Leu Leu Thr Gln Gln Leu Gln Val
            1045                1050            1055

Pro Glu Asn Trp Leu Val Glu Ala Val Arg Ala Val Tyr Asp Leu Asp
            1060                1065            1070

Asn Ile Lys Leu Thr Asp Ile Gly Gly Pro Val His Ser Glu Phe Asp
            1075                1080            1085

Leu Glu Tyr Leu Leu Leu Glu Gly His Cys Phe Asp Ala Ala Ser Gly
            1090                1095            1100

Ala Pro Pro Arg Gly Leu Gln Leu Val Leu Gly Thr Gln Ser Gln Pro
1105                1110            1115                1120

Thr Leu Val Asp Thr Ile Val Met Ala Asn Leu Gly Tyr Phe Gln Leu
            1125            1130            1135

Lys Ala Asn Pro Gly Ala Trp Ser Leu Arg Leu Arg Glu Gly Lys Ser
            1140                1145            1150

Ala Asp Ile Tyr Ala Ile Ser His Ile Glu Gly Thr Asn Thr His His
            1155                1160            1165

Ser Ala Gly Ser Ser Glu Val Gln Val Leu Ile Thr Ser Leu Arg Ser
            1170            1175            1180

His Val Val Lys Leu Arg Val Ser Lys Lys Pro Gly Met Gln Gln Ala
1185                1190            1195                1200

Glu Leu Leu Ser Asp Asp Asn Glu Gln Ala Ala Gln Ser Gly Met Trp
                1205            1210            1215

Asn Ser Ile Ala Ser Ser Phe Gly Gly Gly Ser Ala Asn Gln Ala Ala
            1220            1225            1230

Ser Asp Glu Asp Thr Glu Thr Ile Asn Ile Phe Ser Val Ala Ser Gly
            1235            1240            1245

His Leu Tyr Glu Arg Leu Leu Arg Ile Met Met Val Ser Leu Leu Lys
    1250                1255            1260

His Thr Lys Ser Pro Val Lys Phe Trp Phe Leu Lys Asn Tyr Leu Ser
1265                1270            1275                1280

Pro Gln Phe Thr Asp Phe Leu Pro His Met Ala Ser Glu Tyr Asn Phe
            1285            1290            1295

Gln Tyr Glu Leu Val Gln Tyr Lys Trp Pro Arg Trp Leu His Gln Gln
            1300            1305            1310

Thr Glu Lys Gln Arg Thr Ile Trp Gly Tyr Lys Ile Leu Phe Leu Asp
        1315            1320            1325
```

-continued

```
Val Leu Phe Pro Leu Asn Val Arg Lys Ile Ile Phe Val Asp Ala Asp
    1330                1335                1340

Ala Ile Val Arg Thr Asp Ile Lys Glu Leu Tyr Asp Met Asp Leu Gly
1345                1350                1355                1360

Gly Ala Pro Tyr Ala Tyr Thr Pro Phe Cys Asp Ser Arg Lys Glu Met
                1365                1370                1375

Glu Gly Phe Arg Phe Trp Lys Gln Gly Tyr Trp Arg Ser His Leu Met
            1380                1385                1390

Gly Arg Arg Tyr His Ile Ser Ala Leu Tyr Val Val Asp Leu Lys Arg
        1395                1400                1405

Phe Arg Lys Ile Ala Ala Gly Asp Arg Leu Arg Gly Gln Tyr Gln Ala
    1410                1415                1420

Leu Ser Gln Asp Pro Asn Ser Leu Ser Asn Leu Asp Gln Asp Leu Pro
1425                1430                1435                1440

Asn Asn Met Ile His Gln Val Ala Ile Lys Ser Leu Pro Asp Asp Trp
                1445                1450                1455

Leu Trp Cys Gln Thr Trp Cys Ser Asp Ser Asn Phe Lys Thr Ala Lys
            1460                1465                1470

Val Ile Asp Leu Cys Asn Asn Pro Gln Thr Lys Glu Ala Lys Leu Thr
        1475                1480                1485

Ala Ala Gln Arg Ile Val Pro Glu Trp Lys Asp Tyr Asp Ala Glu Leu
    1490                1495                1500

Lys Thr Leu Met Ser Arg Ile Glu Asp His Glu Asn Ser His Ser Arg
1505                1510                1515                1520

Asp Ser Ala Val Asp Asp Ser Val Asp Ser Val Glu Val Thr Thr
                1525                1530                1535

Val Thr Pro Ser His Glu Pro Lys His Gly Glu Leu
        1540                1545

<210> SEQ ID NO 16
<211> LENGTH: 1493
<212> TYPE: PRT
<213> ORGANISM: Artificial Sequence
<220> FEATURE:
<223> OTHER INFORMATION: C. elegans UGGT

<400> SEQUENCE: 16

Met Asn Leu Thr Gly Leu Leu Ile Phe Phe Cys His Ile Ala Val Leu
1               5                   10                  15

Ala Ala Leu Glu Lys Lys Gly Val His Thr Ser Leu Lys Ala Asn Trp
            20                  25                  30

Asp Ser Thr Ser Leu Leu Ala Glu Ala Ser Glu Phe Ile Ala Glu Glu
        35                  40                  45

Asn Glu Lys Leu Phe Val Lys Phe Ile Asp Ile Val Asn Lys Asp Val
    50                  55                  60

Gly Thr Leu Asn Trp Glu Lys Leu Thr Asp Glu Gln Lys Tyr Glu Tyr
65                  70                  75                  80

Thr Ile Lys Thr Ala Gly Lys Val Leu Ser Thr Ser Ser Val Asp Leu
                85                  90                  95

Leu Lys Phe Ala Leu Ala Leu Arg Gln Tyr Ser Pro Arg Val Gln Ser
            100                 105                 110

Phe Gln Gln Ile Ala Val Glu Tyr Gly Glu Lys Cys Asp Val Phe Val
        115                 120                 125

Val Val Gly Glu Gln Val Ser Cys Glu Tyr Thr Lys Leu Glu Lys Met
    130                 135                 140
```

-continued

```
Ile Lys Asp Ala Lys Thr Asn Ser Gln Val Leu Glu Ser Asp His Ile
145                 150                 155                 160

Phe Gly Glu Lys Asp Leu Lys Gln Ala Ala Ile Leu Tyr Gly Glu Leu
                165                 170                 175

Gly Thr Thr Ser Phe Ala Lys Ala Trp Glu Lys Leu Ser Lys Leu Gln
            180                 185                 190

Lys Thr Lys Leu Ile Phe Arg His Phe Ser Lys Lys Thr Asp Ser His
        195                 200                 205

Pro Val Ser Leu Ser Gly Tyr Gly Val Glu Leu Ala Ile Lys Asn Thr
        210                 215                 220

Glu Tyr Lys Ala Val Asp Glu Ser Ser Glu Lys Lys Asn Val Glu Glu
225                 230                 235                 240

Asp Glu Ala Asp Leu Phe Gly Phe Asn Ile Lys Leu Leu Lys Glu Leu
                245                 250                 255

His Pro Asp Ser Val Asp Ala Ile Glu Ser Phe Arg Val Asn Leu Lys
                260                 265                 270

Glu Ser Asp Glu Leu Thr Pro Leu Lys Arg Trp Glu Leu Gln Asp Leu
            275                 280                 285

Ser Tyr Gln Ala Ala Gln Lys Ile Val Asn Ala Gly Pro Ala Asp Ala
        290                 295                 300

Ile Gly Thr Leu Glu Glu Tyr Ser Gln Asn Phe Pro Thr His Ala Arg
305                 310                 315                 320

Ala Leu Ala Lys Thr Ser Val Ser Asp Leu Leu Arg Lys Glu Val Leu
                325                 330                 335

Gln Asn Arg Lys Met Leu Glu Lys Ala Ser Ile Glu Val Gly Glu Thr
                340                 345                 350

Ser Leu Tyr Ile Asn Gly Ile Asn Gln Asp Ile Asn Ser Leu Asp Leu
            355                 360                 365

Phe Lys Leu Ala Asp Leu Leu Lys Gln Glu Asn Lys Leu Ala Asp Gly
        370                 375                 380

Phe His Ser Met Gly Ile Asn Arg Glu Tyr Leu Ser Ile Leu Val Gly
385                 390                 395                 400

Met Asp Thr Ser Asp Asp Glu Lys Thr Thr Tyr Ala Val Asp His Arg
                405                 410                 415

Glu Gly Tyr Pro Phe Phe Ile Asn Asn Leu Asp Thr Asp Lys Lys Tyr
                420                 425                 430

Lys Gln Trp Gly Asn Ser Val Lys Leu Met Leu Gln Pro Tyr Tyr Pro
            435                 440                 445

Gly Met Ile Arg Pro Ile Ala Arg Asn Leu Phe Ser Leu Val Phe Val
450                 455                 460

Val Asp Pro Ser Thr Ser Glu Gly Arg Lys Phe Leu Arg Ile Gly Gln
465                 470                 475                 480

Thr Phe Asn Ser His Asp Ile Ala Met Arg Ile Gly Tyr Ile Phe Ala
                485                 490                 495

Val Asn Gln Asp Thr Lys Ala Ser Gly Glu Thr Asp Leu Gly Val Ala
                500                 505                 510

Leu Leu Asn Leu Phe Asn Phe Val Ser Ile Asp Ser Ser Asn Ala Asp
            515                 520                 525

Ala Leu Lys Val Leu Asn Asn Phe Leu Asp Asp Tyr Arg Ser Lys Asp
        530                 535                 540

Pro Thr Ile Glu Asp Ile Lys Glu Phe Glu Ala Lys Phe Ser Asp
545                 550                 555                 560
```

-continued

```
Ala Ser Phe Ser Asp Val Phe Gly Val Asn Ser Asp Tyr Asp Lys Gly
            565                 570                 575

Arg Lys His Gly Phe Glu Phe Val Gln Lys Thr Gly Leu Asn Ser Ala
        580                 585                 590

Pro Lys Val Leu Leu Asn Gly Phe Ile Leu Asp Asp Glu Gly Val Arg
        595                 600                 605

Gly Asp Asn Ile Glu Glu Thr Ile Met Met Glu Val Met Lys Ile Ser
    610                 615                 620

Pro Lys Ile Gln Arg Ala Ile Met Glu Gly Lys Leu Thr Asp Arg Met
625                 630                 635                 640

Asn Val Gly Asn Trp Val Leu Glu Gln Lys Asp Val Met Pro Arg Ile
            645                 650                 655

Asn Lys Arg Ile Leu Ser Ala Pro Ser Lys Lys Thr Tyr Val Glu Ile
            660                 665                 670

Leu Gly Ser Met Asp Cys Lys Ser Leu Lys Asp Val Glu Asn Leu Ser
        675                 680                 685

Asp Ser Asp Lys Ala Gly Cys Leu Leu Gln Thr Thr Lys Tyr Leu Gln
    690                 695                 700

Lys Ala Ser Ala Asp Ser Ile Leu Pro Val Thr Leu Trp Val Val Ala
705                 710                 715                 720

Asp Ala Glu Ala Ala Ser Gly Arg Arg Phe Ile Tyr Asn Ser Leu Gln
            725                 730                 735

Ile Leu Lys Asn Ser Ala Asn Ser Arg Val Gly Ile Ile Phe Asn Pro
            740                 745                 750

Glu Ser Val Glu Lys Ala Cys Glu Ser Asn Ser Ile Ser Ser Tyr Ile
        755                 760                 765

Arg Ala Ala Leu Asp Phe Leu Pro Met Asp Gln Ala Lys Arg Leu Ile
    770                 775                 780

Leu Lys Leu Ser Asn Glu Glu Tyr Ala Ala Asp Phe Ile Ser Gly Lys
785                 790                 795                 800

Ile Thr Phe Asp Asp Leu Ser Val Gly Gly Met Asp Thr Ala Lys Phe
            805                 810                 815

Leu Ala Asp Lys Lys Leu Asp Cys Glu Arg Thr Arg Leu Glu Ser
            820                 825                 830

Gln Ile Val Lys Lys Val Leu Asp Ile Ser Ser Gly Gly Arg Val Val
        835                 840                 845

Val Gly Asn Ala Leu Gln Val Gly Pro Leu Glu Ser Ser Glu His Phe
    850                 855                 860

Glu Ala Ala Asp Phe Lys Leu Leu Glu Ser Met Leu Leu Ser Arg Gly
865                 870                 875                 880

Ala Glu Val Ile Ser Ser His Leu Lys Lys Trp Glu Phe Asp Val Ser
            885                 890                 895

Asn Gly Val Gly Ser Asn Thr Val Phe Ser Ile Ala Gly His Val Gly
            900                 905                 910

Lys His Ala Ser Ser Gln Lys Arg Thr Trp Val Ser Ile Gln Gly Asp
        915                 920                 925

Glu His Ser Val Val Thr Leu Pro Ala Asp Glu Met Asp Arg Pro Ala
    930                 935                 940

Val Asp Val Leu Ala Val Val Asp Pro Leu Thr Met Glu Ala Gln Lys
945                 950                 955                 960

Leu Gly Ser Ile Leu His Leu Ile Lys Lys Val Thr Asn Cys Glu Ile
            965                 970                 975

Lys Ile Val Met Asn Pro Lys Asp Lys His Ser Glu Leu Pro Leu Lys
```

-continued

```
              980            985            990
Arg Phe Tyr Arg Tyr Ala Ala Ala Ser Glu Leu Ser Phe Asp His Asn
            995            1000           1005

Gly Asn Leu Asn Thr Asn Val Val Arg Phe Asp Asn Leu Pro Ser Lys
    1010           1015           1020

Gln Leu Leu Thr Leu Ser Leu Gln Ala Pro Asp Ser Trp Ile Val Glu
1025           1030           1035           1040

Ala Val Ser Ala Lys Tyr Asp Leu Asp Asn Ile Lys Met Glu Gln Ala
            1045           1050           1055

Asn Gly Asp Val Thr Ala Glu Phe Ala Leu Gln His Leu Leu Leu Asp
            1060           1065           1070

Gly Gln Cys Phe Asp Glu Val Ser Gly Gln Pro Pro Arg Gly Leu Gln
            1075           1080           1085

Phe Thr Leu Gly Thr Asp Lys Asn Pro Lys Gln Phe Asp Thr Ile Val
            1090           1095           1100

Met Ala Asn Leu Gly Tyr Phe Gln Leu Lys Ala Asn Pro Gly Ala Trp
1105           1110           1115           1120

Lys Leu Glu Ile Arg Asp Gly Lys Ser Ser Glu Ile Tyr Lys Ile Gly
            1125           1130           1135

Ser His Val Gly Ala Glu Lys Ile Gly Glu Asp Val Leu Gln Val Val
            1140           1145           1150

Ile Asp Ser Phe Thr Gly Lys Ser Val Arg Val Arg Val Glu Lys Arg
            1155           1160           1165

Glu Gly Met Glu Glu Arg Asn Leu Leu Ser Asp Asp Glu Glu Gly Val
            1170           1175           1180

Trp Ser Ser Leu Ser Asn Leu Val Ser Ser Lys Glu Lys Thr Gln Glu
1185           1190           1195           1200

Val Ile Asn Val Phe Ser Leu Ala Ser Gly His Leu Tyr Glu Arg Phe
            1205           1210           1215

Met Arg Ile Met Ile Val Ser Val Met Lys Asn Thr Lys His Pro Val
            1220           1225           1230

Lys Phe Trp Leu Leu Lys Asn Tyr Leu Ser Pro Gln Phe Lys Glu Thr
            1235           1240           1245

Leu Pro Thr Leu Ala Lys His Tyr Gly Phe Glu Tyr Glu Leu Ile Glu
            1250           1255           1260

Tyr Lys Trp Pro Arg Trp Leu His Gln Gln Lys Glu Lys Gln Arg Ile
1265           1270           1275           1280

Met Trp Gly Phe Lys Ile Leu Phe Leu Asp Val Leu Phe Pro Leu Asp
            1285           1290           1295

Val Gln Lys Val Ile Phe Val Asp Ala Asp Gln Val Val Arg Ala Asp
            1300           1305           1310

Leu Met Glu Leu Met Lys Phe Asp Leu Gly Asn Ala Pro Tyr Gly Tyr
            1315           1320           1325

Val Pro Phe Cys Glu Ser Arg Lys Glu Met Asp Gly Phe Arg Phe Trp
            1330           1335           1340

Lys Gln Gly Tyr Trp Ala Asn His Leu Ala Gly Arg Arg Tyr His Ile
1345           1350           1355           1360

Ser Ala Leu Tyr Val Ile Asp Leu Gln Lys Phe Arg Gln Ile Ala Ala
            1365           1370           1375

Gly Asp Arg Leu Arg Gly Gln Tyr Gln Gly Leu Ser Gly Asp Pro Asn
            1380           1385           1390

Ser Leu Ala Asn Leu Asp Gln Asp Leu Pro Asn Asn Met Ile His Gln
            1395           1400           1405
```

-continued

```
Val Lys Ile Lys Ser Leu Pro Gln Glu Trp Leu Trp Cys Glu Thr Trp
    1410                1415                1420

Cys Asp Asp Gly Ser Lys Lys Asn Ala Lys Thr Ile Asp Leu Cys Asn
1425                1430                1435                1440

Asn Pro Leu Thr Lys Glu Pro Lys Leu Asp Ser Ala Ala Arg Ile Ile
                1445                1450                1455

Gly Glu Trp Lys Thr Tyr Asp Asp Glu Ile Arg Glu Val Ile Ser Gly
                1460                1465                1470

His Ser Ser Asp Asn Pro Ser Asp Asn Val Ile Ser Glu Asn Asp Asp
        1475                1480                1485

Ser His Thr Glu Leu
    1490

<210> SEQ ID NO 17
<211> LENGTH: 1447
<212> TYPE: PRT
<213> ORGANISM: Artificial Sequence
<220> FEATURE:
<223> OTHER INFORMATION: S. pombe UGGT

<400> SEQUENCE: 17

Met Arg Trp Gly Phe Trp Phe Ala Ile Ala Thr Leu Ile Thr Ile Cys
1               5                   10                  15

Tyr Ala Ala Lys Pro Leu Asp Val Lys Ile Ala Ala Thr Phe Asn Ala
            20                  25                  30

Pro Ser Phe Ser Ala Leu Ile Ala Glu Ser Leu Tyr Gln Glu Lys Lys
        35                  40                  45

Glu Gly Phe Ile Trp Tyr Leu Asn His Leu Ser Asp Leu Leu Asp Ala
    50                  55                  60

Glu Asn Thr Thr Glu Lys Glu Leu Tyr Ile Asn Val Asn Ser Leu
65                  70                  75                  80

Lys Arg Glu Tyr Val Leu Ser Asp Glu Leu Ser Ser Leu Gln Phe
                85                  90                  95

Ser Leu Gly Leu Phe Ser Gly Ala Pro Lys Leu Gln Ala Phe Ser Ser
            100                 105                 110

Ile Val Gln Ser Arg Thr Cys Asp Cys Asp Thr Trp Leu Gln Leu Asp
        115                 120                 125

Glu Glu Ser Gln Val Cys Phe Ser Asp Leu Pro Lys Asp Ser Pro Leu
    130                 135                 140

Phe Ser Lys Leu Tyr Ser Lys Asn Pro Leu Asp Tyr Glu Val Val Lys
145                 150                 155                 160

Thr Ser Ala Thr Gly Ile Pro Tyr Ala Val Val Thr Ser Phe Glu
                165                 170                 175

Arg Asp Leu Ile Pro Phe His Glu Leu Tyr Tyr Lys Leu Ala Leu Glu
            180                 185                 190

Gly Lys Cys Asn Tyr Val Ile Arg Tyr Ser Pro Ser Ser Ser Lys
        195                 200                 205

Leu Asn Ser Lys Leu Tyr Val Lys Gly Phe Gly Thr His Val Ser Leu
    210                 215                 220

Lys Arg Thr Asp Tyr Leu Val Val Asp Arg Glu Phe Pro Arg Glu
225                 230                 235                 240

Lys Gly Asp Asn Pro Ala Ser Phe Thr Ser Arg Asn Lys Arg Ser
                245                 250                 255

Asn Glu Arg Leu Phe Gly Met Thr Ser Asp Ser Leu Gln Thr Val Thr
            260                 265                 270
```

```
Pro Asp Lys Ile Ala Ile Leu Asp Leu Leu Ala Thr Gln Ser Ile Ala
            275                 280                 285

Ser Ser Ala Asp Met Leu Ser Ala Phe Arg Glu Leu Thr Gln Asp Phe
        290                 295                 300

Pro Ile Tyr Ala His Tyr Leu Ser Ile Gln Pro Asp Val Ser Asn His
305                 310                 315                 320

Leu Ile Glu Glu Leu Asn Gln Phe Gln Ser Gln Tyr Val Pro Glu Gly
                325                 330                 335

Ile Asn Thr Ile Trp Leu Asn Gly Leu Ser Leu Asp Leu Glu Glu Thr
            340                 345                 350

Asp Ala Phe Ser Ile Leu Ser Leu Ile Lys Lys Glu Lys Asp Met Phe
        355                 360                 365

Asp Arg Phe Glu Ala Leu Gly Ile Lys Ser Ser Lys Val Leu Asp Ile
370                 375                 380

Val Thr Asn Glu Ala Phe Ala Asn Glu Asp Ser Asp Phe Lys Phe Val
385                 390                 395                 400

Lys Phe His Cys Gln Asp Asp Ile Glu Asp Trp Lys Ala Ile His Trp
                405                 410                 415

Val Asn Glu Ile Glu Ser Asn Pro Lys Tyr Asp Asn Trp Pro Lys Ser
            420                 425                 430

Ile Gln Ile Leu Leu Lys Pro Ile Tyr Pro Gly Gln Leu His Met Leu
        435                 440                 445

Gly Lys Gln Leu His Thr Val Ile Tyr Pro Ile Phe Pro Ser Ser Pro
450                 455                 460

Ser Ser Leu Pro Leu Leu Ser Glu Leu Ile Gln Phe Ser Arg Arg Pro
465                 470                 475                 480

Ser Pro Val Gln Thr Gly Met Val Cys Ala Ala Asn Asp Asp Asp Glu
                485                 490                 495

Phe Ala Gln Thr Val Cys Lys Ser Phe Phe Tyr Ile Ser Lys Glu Ser
            500                 505                 510

Gly Thr Asp Ser Ala Leu Lys Phe Leu Tyr Lys Cys Leu Asn Ser Asp
        515                 520                 525

Ser Ser Ala Asp Leu Tyr Ser Leu Leu Glu Glu His Leu Pro Leu Ser
530                 535                 540

Glu His Asp Asp Asp Thr Leu Ala Asn Leu Lys Lys Asp Leu Ser Ser
545                 550                 555                 560

Ser Phe Phe Asp His Tyr Met Ser Lys Ser Asn Ser Trp Val Asn Arg
                565                 570                 575

Leu Gly Ile Asp Ser Ser Ala Ser Glu Val Ile Val Asn Gly Arg Ile
            580                 585                 590

Ile Ser His Asp Glu Asn Tyr Asp Arg Ser Met Tyr Gly Ile Phe Leu
        595                 600                 605

Glu Asp Ile Pro Glu Val Gln Ile Ala Val Ala Glu Gly Lys Ile Ser
610                 615                 620

Glu Asp Asp Asn Leu Leu Asp Phe Ile Leu Arg Asp Ala Ser Leu Thr
625                 630                 635                 640

Arg Asn Pro Leu Val Tyr Pro Ser Ala Lys Ser Ser Ile Lys Ser Ile
                645                 650                 655

Asp Ile Lys Arg Val Leu Glu Asn Val Gly Ser Leu Asn His Glu Asp
            660                 665                 670

Ile Leu Leu Ile Gly Ser Ser Asn Ala Lys Tyr Ser Phe Trp Leu Val
        675                 680                 685
```

-continued

Ala Asp Phe Asn Glu Lys Glu Gly Leu Glu Ile Leu Ser Leu Leu Ala
    690             695             700

Asp Leu Leu Ser Glu Asn Lys Asp Ala Asn Leu Met Leu Ile Gln Glu
705             710             715             720

Gly Lys Asn His Val Val Pro Pro Leu Phe Ala Lys Leu Leu Ser Ser
                725             730             735

Pro Lys Arg Ser Ser Lys His Leu Gln Glu Ile Leu Asn Ser Ser Leu
        740             745             750

Asp Pro Ser Ser Gly Val Val Asn Asp Met Asp Lys Ala Leu Lys Phe
        755             760             765

Leu Lys Lys Ser Lys Ala Val Val Lys Glu Leu Gly Leu Thr Gly Glu
    770             775             780

Cys Lys Ser Ala Leu Leu Asn Gly Arg Met Ile Cys Ser Phe Ser
785             790             795             800

Val Asp Ser Leu Asn Thr Ala Asp Leu Lys Met Leu Met Gln Met Glu
                805             810             815

Tyr Asp Asn Tyr Leu Ser Lys Leu Ser Asn Ile Ala Gly Ser Ser Arg
        820             825             830

Arg Leu Lys Asn Ser Arg Ala Ile Ser Phe Leu Ser Ser Tyr Leu Lys
    835             840             845

Thr Leu Glu Ser Thr Pro Met Ser Thr Ser Ser Pro Thr Lys Glu Glu
    850             855             860

Lys Leu Phe Pro Arg Asp Phe Ile Tyr Asn Lys Leu Gly Val Gly Asn
865             870             875             880

Ala Thr Phe Glu Thr Asp Asp Phe Ser Lys Ala Tyr Tyr Gln Phe Val
                885             890             895

Ala Val Leu Asp Pro Leu Ser Lys Asp Ser Gln Lys Trp Ser Ala Ile
            900             905             910

Leu Glu Ala Val Ser Lys Leu Asn Gly Val Gly Val Arg Ile His Leu
        915             920             925

Asn Pro Lys Gln Thr Leu Ser Glu Leu Pro Leu Thr Arg Phe Tyr Arg
    930             935             940

Tyr Ser Ile Ser Ala Glu Pro Glu Phe Asp Ala Leu Gly His Leu Glu
945             950             955             960

Glu Ser Tyr Val Glu Phe Asp Asn Leu Pro Ala Asp Thr Leu Leu Thr
                965             970             975

Met Asp Ile Glu Ala Arg Asp Ala Trp Thr Val Met Gln Lys Asp Val
            980             985             990

Asp Ile Asp Leu Phe Asn Ile Lys Leu Glu His Thr Ser Glu Ala Glu
        995             1000            1005

Ala Leu Asp Ser His Thr Ala Ile Tyr Glu Leu Lys Asn Ile Leu Val
    1010            1015            1020

Gln Gly Tyr Ser Gln Glu Glu Phe Arg Lys Ser Pro Pro Arg Gly Met
1025            1030            1035            1040

Gln Leu Lys Leu Gly Asn Leu Thr Asn Ser His Val Thr Asp Thr Ile
                1045            1050            1055

Val Leu Ser Asn Leu Gly Tyr Phe Gln Leu Lys Ala Asn Pro Gly Val
            1060            1065            1070

Trp Thr Leu Glu Pro Met Asp Gly Arg Ser Ser Gln Phe Tyr Glu Ile
        1075            1080            1085

Leu Ser Leu Asn Lys Lys Asn Ser Tyr Lys Asp Pro Gln Val Ile Val
    1090            1095            1100

Asp Ser Phe Glu Gly Val Thr Leu Asn Pro Val Met Arg Arg Lys Pro

```
                1105                1110                1115                1120

Gly Phe Glu Ser Ala Asp Ile Met Asp Glu Asp Leu Ser Ser His Lys
                         1125                1130                1135

Phe Phe Asp Lys Ile Lys Lys Ser Leu Ser Phe Phe Asn Phe Lys Arg
                     1140                1145                1150

Lys Glu Ala Ser Ile Asn Ile Phe Ser Val Ala Ser Gly His Leu Tyr
                     1155                1160                1165

Glu Arg Phe Leu Tyr Ile Met Thr Lys Ser Val Ile Glu His Thr Asp
                     1170                1175                1180

Lys Lys Val Lys Phe Trp Phe Ile Glu Asn Phe Leu Ser Pro Cys Phe
       1185                1190                1195                1200

Lys Ser Ser Ile Pro Ala Ile Ala Lys Lys Tyr Asn Phe Glu Tyr Glu
                         1205                1210                1215

Tyr Ile Thr Tyr Asn Trp Pro His Trp Leu Arg Lys Gln Glu Glu Lys
                     1220                1225                1230

Gln Arg Glu Ile Trp Gly Tyr Lys Ile Leu Phe Leu Asp Val Leu Phe
                     1235                1240                1245

Pro Leu Glu Leu His Lys Val Ile Tyr Val Asp Ala Gln Ile Val Arg
       1250                1255                1260

Ala Asp Leu Gln Glu Leu Met Asp Met Asp Leu His Gly Ala Pro Tyr
       1265                1270                1275                1280

Gly Tyr Thr Pro Met Cys Asp Ser Arg Glu Glu Met Glu Gly Phe Arg
                         1285                1290                1295

Phe Trp Lys Lys Gly Tyr Trp Lys Lys Phe Leu Arg Gly Leu Lys Tyr
                     1300                1305                1310

His Ile Ser Ala Leu Tyr Val Val Asp Leu Asp Arg Phe Arg Lys Met
                     1315                1320                1325

Gly Ala Gly Asp Leu Leu Arg Arg Gln Tyr Gln Leu Leu Ser Ala Asp
       1330                1335                1340

Pro Asn Ser Leu Ser Asn Leu Asp Gln Asp Leu Pro Asn His Leu Gln
       1345                1350                1355                1360

His Leu Ile Pro Ile Tyr Ser Leu Pro Gln Asp Trp Leu Trp Cys Glu
                         1365                1370                1375

Thr Trp Cys Ser Asp Glu Ser Leu Lys Thr Ala Lys Thr Ile Asp Leu
                     1380                1385                1390

Cys Gln Asn Pro Leu Thr Lys Glu Lys Lys Leu Asp Arg Ala Arg Arg
                     1395                1400                1405

Gln Val Ser Glu Trp Thr Ser Tyr Asp Asn Glu Ile Ala Ser Val Leu
           1410                1415                1420

Gln Thr Ala Ser Ser Gln Ser Asp Lys Glu Phe Glu Glu Lys Asp Asn
       1425                1430                1435                1440

Asn Ser Ser Pro Asp Glu Leu
                     1445

<210> SEQ ID NO 18
<211> LENGTH: 1365
<212> TYPE: PRT
<213> ORGANISM: Artificial Sequence
<220> FEATURE:
<223> OTHER INFORMATION: S. cerevisiae KRE5

<400> SEQUENCE: 18

Met Arg Leu Leu Ala Leu Val Leu Leu Leu Cys Ala Pro Leu Arg
  1               5                  10                  15

Ala Trp Thr Tyr Ser Leu Arg Tyr Gly Ile Pro Glu Ser Ala Gln Val
```

-continued

```
                20                  25                  30
Trp Ser Ile Leu Val His Leu Leu Gly Asp Val Asp Asn Gln Leu Leu
            35                  40                  45
Thr Asn Leu Tyr Pro Leu Val Thr Gly Leu Asp Asp Glu Ile Asp Ile
50                  55                  60
Gln Glu Asn Leu Val Ala Leu Thr Ser Asn Val Leu Arg Glu Arg Tyr
65                  70                  75                  80
Asp Lys Glu Asp Val Ala Asp Leu Leu Glu Leu Tyr Ala Ser Leu Tyr
                85                  90                  95
Pro Met Gly Met Ile Gln His Asp Ile Ser Ser Asn Ala Glu Gln Asp
                100                 105                 110
Asp Ala Asn Ser Ser Tyr Phe Val Leu Asn Gly Asn Arg Tyr Glu Lys
            115                 120                 125
Pro Asp Asp Val Phe Tyr Leu Lys Ser Lys Asp Leu Thr Ile Gln Gln
130                 135                 140
Lys Val Pro Asp Val Asp Val Ile Gln Pro Tyr Asp Val Val Ile Gly
145                 150                 155                 160
Thr Asn Ser Glu Ala Pro Ile Leu Ile Leu Tyr Gly Cys Pro Thr Val
                165                 170                 175
Ile Asp Ser Asp Phe Glu Glu Phe Asn Arg Asn Leu Phe Met Glu Ala
                180                 185                 190
Met Asn Gly Glu Gly Lys Phe Arg Phe Ile Trp Arg Ser Thr Cys Ser
                195                 200                 205
Leu Asp Gly Lys Ser Val Glu Tyr Pro Leu Thr His Pro Leu Glu Ile
            210                 215                 220
Thr Leu Gln Asn Gly Ser Arg Met Ser Ser Ile Pro Gln Leu Lys Lys
225                 230                 235                 240
Ile Leu Tyr Thr Val Pro Lys Glu Ile Leu Val Gly Ala Asp Asn Asp
                245                 250                 255
Asp Gln Leu His Asp Leu Glu Pro Glu Glu Leu Arg Glu Leu Asp Leu
            260                 265                 270
Arg Val Thr Ser Leu Ile Ser Glu Phe Tyr Gln Tyr Lys Lys Asp Ile
            275                 280                 285
Thr Ala Thr Leu Asn Phe Thr Lys Ser Ile Val Asn Asn Phe Pro Leu
            290                 295                 300
Ile Ser Lys Gln Leu Ile Lys Val Ser Val Asn Lys Asp Ile Ile
305                 310                 315                 320
Thr Ser Asn Glu Glu Leu Asn Ser Lys Gly Phe Asp Tyr Asn Met Leu
                325                 330                 335
Gly Leu Tyr Ile Asn Gly Gln Asn Trp Lys Ile Thr Ser Leu Thr Pro
            340                 345                 350
Tyr Asn Leu Leu Thr Ala Leu Lys Thr Glu Tyr Gln Ser Leu Leu Lys
            355                 360                 365
Ile Thr Asn Leu Leu Gln Glu Leu Glu Pro Ser Lys Cys Ile Leu Asp
            370                 375                 380
Ser Lys Phe Leu Leu Asn Lys Phe Ser Gln Phe Ser Leu Gly Lys Leu
385                 390                 395                 400
Gln Asn Leu Gln Pro Ile Lys Met Asp Leu His Thr Ile Pro Gly Phe
                405                 410                 415
Ser Glu Ser Val Ile Tyr Phe Asn Asp Ile Glu Ser Asp Pro Gln Tyr
                420                 425                 430
Asp Glu Leu Val Asn Ser Val Gln Ala Phe Phe Asp Lys Ser Lys Phe
            435                 440                 445
```

```
Gly Glu Leu Pro Glu Ile Lys Gln Asn Trp Ser Glu Ile Ile Phe Val
    450                 455                 460
Ile Asp Phe Ala Arg Leu Glu Asp Ser Glu Val Lys Glu Ala Leu Gly
465                 470                 475                 480
Gly Leu Val Arg Ala Val Asn Val Val Ser Gln Gly Tyr Pro Gln Arg
                485                 490                 495
Val Gly Leu Leu Pro Phe Ser Ser Asp Ser Asp Lys Ser Val Val Asn
                500                 505                 510
Lys Ile Tyr Glu Leu Lys Asn Ser Thr Asp Asn Leu Thr Glu Leu Lys
            515                 520                 525
Ser Phe Leu Glu Thr Met Leu Leu Ala Asp Gly Leu Ser Ala Asn Ala
    530                 535                 540
Lys His Ser Lys His Ile Pro Val Pro Asp Val Phe His Leu Leu Asp
545                 550                 555                 560
Glu Leu Gln Ile Asp Glu Thr Ser Ile Ile Asn Gly Glu Ile Tyr
                565                 570                 575
Pro Phe Arg Lys Asn Trp Asn Tyr Leu Ile Ala Lys Val Ile Lys Lys
            580                 585                 590
Asp Thr Glu Phe Ile Arg Lys Glu Leu Ser Asn Ser Ser Pro Lys Asn
                595                 600                 605
Lys Gln Ile Ser Val Arg Asp Leu Leu His Tyr Lys Ser Ala Asn Leu
            610                 615                 620
Arg His Asn Lys Tyr Thr Pro Asn Tyr Phe Ala Asp Ser Val Tyr Ser
625                 630                 635                 640
Ser Val Asn Asn Thr Ala Leu Glu Ser Val Cys Ser Glu Arg Ile Gly
                645                 650                 655
Tyr Tyr Thr Lys Asn Glu Glu Tyr Asn Leu Leu His Thr Ile Thr Leu
            660                 665                 670
Val Asp Asp Phe Gly Ser Ile His Ala Leu Lys Arg Leu Arg Asn Leu
            675                 680                 685
Leu His Thr Ser Phe Val Gly Val Arg Ile Arg Ile Ile His Val Gly
    690                 695                 700
Asp Ile Ser Asp Ile Trp Tyr Gln Leu Arg Gly Ser Leu Ser Gln Lys
705                 710                 715                 720
Asp Pro Ile Gly Ser Ile Asn Thr Phe Ile Asp Ala Leu Lys Leu Lys
                725                 730                 735
Lys Val Lys Ser His Thr Tyr Lys Lys Ser Gly Leu Asn Gln Leu Gly
            740                 745                 750
Leu His Lys Trp Leu Pro Asp Ile Pro Leu Phe Glu Leu Gln Lys Gly
    755                 760                 765
Ser Phe Ile Ala Leu Asn Gly Arg Phe Ile Ile Leu Ile Lys Met Lys
    770                 775                 780
Cys Gln Lys Gln Asn Ile Ser Lys Ala Lys Ile Ile Lys Arg Glu Ala
785                 790                 795                 800
Leu Arg Thr Ile Asp Ser Val Phe Ala Leu Asp Leu Leu Phe Pro Gly
                805                 810                 815
Phe Ser Gln Glu Ile Ile Asn Pro Asp Leu Ile Glu Met Ile Ser Ser
                820                 825                 830
Ile Leu Thr Arg Leu Phe Tyr Gln Gly Thr His Ile Tyr Asn Asn Gly
            835                 840                 845
Ile Asp Tyr Thr Thr Glu Ser Ser Leu Pro Arg Met Asp Leu Ser Glu
            850                 855                 860
```

```
Phe Phe Arg Pro Asn Asn Leu Thr Met Phe Glu Asp Gly Lys Ser Ala
865                 870                 875                 880

Ser Ile Asp Leu Leu Leu Ile Leu Asp Pro Leu Glu Glu Arg Thr Gln
                885                 890                 895

Met Ile Leu Ser Leu Val Glu Gln Phe Arg Pro Leu Lys Phe Val Asn
                900                 905                 910

Ile Gln Val Ile Leu Met Pro Thr Leu Glu Leu Asn Ile Val Pro Ile
            915                 920                 925

Arg Arg Ile Tyr Val Asp Asp Ala Asp Ile Val Lys Ser Ile Thr Ser
930                 935                 940

Glu Asp Ser Arg Ser Asp Pro Glu Val Asp Ile Glu Met Asp Val Pro
945                 950                 955                 960

Asn Ser Phe Ile Val Asp Asn Asn Tyr Arg Ile Lys Lys Leu Leu Ile
                965                 970                 975

Glu Leu His Ser Phe Ser Ser Lys Thr Val Leu Ser Thr Gly Asn Ile
                980                 985                 990

Asp Gly Met Gly Gly Val Cys Leu Ala Leu Val Asp Ser Ala Gly Asn
            995                 1000                1005

Ile Ile Asp Lys Thr Thr Thr Met Lys Thr Phe Gly Tyr Gly Gln Phe
    1010                1015                1020

His Thr Asp Lys Phe Leu Lys Gly Cys Tyr Ile Lys Ser Cys Asp Ser
1025                1030                1035                1040

Arg Tyr Thr Val Gln Ser Phe Ser Thr Asp Gly His Pro Asp Phe Ile
                1045                1050                1055

Pro Ser Asp Ser Leu Asp Ile Leu Ser Tyr Asn Pro Gln Lys Ile Ala
                1060                1065                1070

Val Lys Ile Ser Glu Glu Pro Thr His Glu Glu Tyr Glu Glu Gly
            1075                1080                1085

Arg Asn Asn Asp Thr Ile Ile Asn Ile Phe Thr Ile Leu Glu Ser Gly
                1090                1095                1100

Pro Asp Glu Glu Glu Arg Tyr Met Gln Met Ile Leu Ser Ile Leu Ser
1105                1110                1115                1120

Lys Cys Pro Glu Thr Gln Lys Val Asn Phe Phe Ile Leu Asp Gln Pro
                1125                1130                1135

Phe Ile Ser Asp Thr Leu Arg Lys Ser Cys Glu Tyr Ile Asn Ser Ser
                1140                1145                1150

Asp Glu Met Arg Gly Asn Val Ile Phe Leu Asn Tyr Glu Trp Pro Gln
                1155                1160                1165

Trp Leu Arg Pro Gln Arg Phe Ser Ser Arg Arg Asp Val Ser Arg
            1170                1175                1180

Phe Leu Phe Leu Asp Val Leu Leu Pro Gln Asn Ile Ser Lys Val Leu
1185                1190                1195                1200

Tyr Met Ser Pro Thr Glu Val Pro Leu Asp Pro Phe Asp Ile Phe Gln
                1205                1210                1215

Phe Gln Gly Leu Lys Arg Ala Pro Leu Gly Leu Phe Arg Met Ser Gly
                1220                1225                1230

Asp Gly Tyr Trp Lys Glu Gly Tyr Trp Glu Lys Met Leu Arg Glu Asn
                1235                1240                1245

Asn Leu Glu Phe Tyr Ser Thr Glu Pro Ala Phe Leu Val Asn Leu Glu
                1250                1255                1260

Arg Phe Arg Glu Leu Asp Ala Gly Asp Lys Tyr Arg Ile His Tyr Gln
1265                1270                1275                1280

Arg Ile Ser Thr Asp Ala Met Ser Leu Val Asn Ile Gly Gln Asp Leu
```

-continued

```
                    1285               1290                1295
Val Asn Asn Leu Gln Leu Glu Val Pro Ile Arg Phe Leu Lys Gly Ser
           1300                1305                1310

Tyr Lys Lys Leu Val Ile Asn Asp Glu Cys Val Ser Glu Trp Lys
           1315                1320                1325

Lys Lys Ile Asn Lys Phe Ala Ser Ser Pro Gly Asp Glu Asp Val Pro
           1330                1335                1340

Gly Glu Ser Val Ser Ser Lys Tyr Gln Asp Ser Asp Asn Ala Ala Pro
1345                1350                1355                1360

Leu His Asp Glu Leu
           1365

<210> SEQ ID NO 19
<211> LENGTH: 1626
<212> TYPE: PRT
<213> ORGANISM: Artificial Sequence
<220> FEATURE:
<223> OTHER INFORMATION: Consensus Sequence
      Xaa = any amino acid

<400> SEQUENCE: 19

Lys Xaa Ile Xaa Thr Ser Xaa Xaa Ala Xaa Xaa Xaa Xaa Trp Ser Leu
 1               5                  10                  15

Leu Xaa Glu Xaa Xaa Glu Xaa Leu Ala Xaa Glu Xaa Xaa Xaa Leu Phe
           20                  25                  30

Xaa Xaa Xaa Xaa Xaa Xaa Xaa Xaa Xaa Xaa Xaa Xaa Xaa Xaa Xaa Xaa
           35                  40                  45

Glu Xaa Asp Thr Xaa Xaa Xaa Xaa Tyr Xaa Ala Xaa Xaa Xaa Xaa Xaa
50                  55                  60

Xaa Arg Xaa Xaa Xaa Leu Ser Xaa Xaa Xaa Xaa Xaa Leu Leu Xaa Phe
65                  70                  75                  80

Xaa Leu Ser Leu Xaa Ser Xaa Xaa Pro Xaa Ile Gln Xaa Phe Xaa Gln
           85                  90                  95

Ile Ala Xaa Xaa Xaa Xaa Xaa Xaa Xaa Gly Xaa Cys Xaa Ser Xaa Xaa
           100                 105                 110

Phe Xaa Xaa Val Gly Xaa Xaa Xaa Xaa Xaa Cys Xaa Xaa Xaa Xaa Leu
           115                 120                 125

Xaa Lys Xaa Xaa Xaa Xaa Xaa Leu Xaa Xaa Xaa Xaa Xaa Xaa Xaa Xaa
           130                 135                 140

Val Leu Xaa Xaa Xaa Xaa Asp His Xaa Xaa Xaa Gly Ser Xaa Xaa Xaa
145                 150                 155                 160

Xaa Pro Xaa Xaa Ile Leu Tyr Gly Xaa Xaa Xaa Xaa Gly Xaa Xaa Xaa
           165                 170                 175

Phe Xaa Xaa Xaa Xaa His Xaa Leu Xaa Xaa Lys Xaa Xaa Asn Xaa Glu
           180                 185                 190

Gly Lys Xaa Xaa Tyr Ile Xaa Arg His Xaa Xaa Xaa Xaa Xaa Xaa Xaa
           195                 200                 205

Xaa Xaa Xaa Pro Val Xaa Leu Ser Gly Tyr Gly Val Glu Leu Xaa Xaa
           210                 215                 220

Lys Ser Thr Glu Tyr Lys Xaa Xaa Asp Asp Xaa Xaa Xaa Xaa Xaa Xaa
225                 230                 235                 240

Xaa Gly Xaa Xaa Xaa Xaa Xaa Xaa Xaa Xaa Xaa Xaa Xaa Xaa Xaa Xaa
           245                 250                 255

Xaa Gly Phe Xaa Phe Xaa Xaa Leu Lys Xaa Leu Xaa Pro Xaa Leu Xaa
           260                 265                 270
```

```
Xaa Xaa Leu Xaa Xaa Xaa Arg Xaa Xaa Leu Xaa Xaa Xaa Xaa Asp Glu
        275                 280                 285

Xaa Ala Xaa Leu Lys Xaa Trp Glu Leu Gln Asp Leu Xaa Xaa Gln Ala
        290                 295                 300

Ala Xaa Xaa Ile Xaa Xaa Xaa Xaa Xaa Xaa Xaa Xaa Xaa Xaa Xaa Xaa
305                 310                 315                 320

Xaa Leu Xaa Xaa Xaa Xaa Xaa Xaa Xaa Gln Asn Phe Pro Xaa Xaa Ala
                325                 330                 335

Arg Xaa Leu Xaa Xaa Xaa Xaa Xaa Val Ser Xaa Xaa Leu Arg Xaa Glu
        340                 345                 350

Val Xaa Xaa Asn Xaa Xaa Xaa Xaa Xaa Xaa Xaa Xaa Xaa Xaa Xaa Xaa
        355                 360                 365

Gly Xaa Xaa Leu Xaa Ile Asn Gly Leu Xaa Xaa Asp Xaa Xaa Xaa
370                 375                 380

Xaa Asp Xaa Phe Ser Leu Xaa Xaa Xaa Leu Lys Xaa Glu Xaa Xaa Xaa
385                 390                 395                 400

Xaa Xaa Xaa Xaa His Xaa Leu Gly Ile Xaa Xaa Xaa Xaa Xaa Xaa
                405                 410                 415

Ile Leu Xaa Xaa Xaa Xaa Xaa Xaa Xaa Xaa Xaa Phe Ala Xaa
        420                 425                 430

Asp Xaa Arg Xaa Xaa Xaa Xaa Xaa Xaa Xaa Asp Ile Arg Xaa Xaa
        435                 440                 445

Xaa Xaa Xaa Xaa Xaa Ala Xaa Xaa Trp Val Asn Xaa Ile Glu Xaa Asp
450                 455                 460

Xaa Xaa Tyr Xaa Xaa Trp Pro Xaa Ser Val Gln Xaa Leu Leu Xaa Pro
465                 470                 475                 480

Xaa Xaa Pro Gly Xaa Leu Arg Xaa Ile Xaa Lys Asn Leu Xaa Xaa Xaa
                485                 490                 495

Val Phe Val Val Asp Pro Xaa Xaa Xaa Xaa Xaa Xaa Xaa Xaa Xaa
                500                 505                 510

Xaa Xaa Xaa Xaa Phe Xaa Xaa Xaa Xaa Xaa Pro Xaa Arg Xaa Gly Xaa
        515                 520                 525

Val Phe Ala Val Asn Asp Xaa Xaa Xaa Xaa Xaa Xaa Xaa Asp Xaa
530                 535                 540

Xaa Val Ala Xaa Leu Xaa Xaa Phe Asn Tyr Val Ser Xaa Xaa Ser Asp
545                 550                 555                 560

Xaa Xaa Xaa Ala Leu Xaa Xaa Leu Xaa Xaa Ile Tyr Xaa Xaa Xaa Xaa
                565                 570                 575

Xaa Xaa Xaa Xaa Xaa Xaa Xaa Xaa Xaa Xaa Xaa Leu Glu Xaa
        580                 585                 590

Xaa Xaa Xaa Xaa Asp Xaa Xaa Xaa Ala Xaa Xaa Xaa Xaa Leu Xaa
        595                 600                 605

Xaa Xaa Ser Xaa Tyr Asp Xaa Xaa Arg Xaa Xaa Xaa Xaa Xaa Xaa
        610                 615                 620

Xaa Xaa Leu Gly Xaa Xaa Xaa Xaa Xaa Pro Xaa Val Leu Xaa Asn
625                 630                 635                 640

Gly Xaa Xaa Xaa Xaa Xaa Xaa Xaa Xaa Asp Xaa Asn Xaa Glu
                645                 650                 655

Xaa Xaa Ile Xaa Xaa Xaa Ile Xaa Xaa Xaa Thr Xaa Xaa Xaa Gln Xaa
                660                 665                 670

Ala Val Xaa Xaa Gly Xaa Leu Xaa Xaa Asp Xaa Xaa Val Xaa Xaa Xaa
        675                 680                 685

Xaa Xaa Leu Xaa Gln Xaa Xaa Val Xaa Pro Arg Xaa Asn Xaa Arg Ile
```

-continued

```
            690                 695                 700
Leu Xaa Ser Ala Xaa Xaa Xaa Xaa Tyr Xaa Asp Ile Xaa Xaa Xaa
705                 710                 715                 720

Xaa Xaa Xaa Asn Xaa Xaa Leu Xaa Xaa Val Xaa Xaa Xaa Xaa Leu
                725                 730                 735

Xaa Xaa Xaa Asp Xaa Xaa Xaa Xaa Xaa Xaa Xaa Xaa Lys Tyr Xaa
                740                 745                 750

Xaa Lys Xaa Xaa Xaa Ser Xaa Xaa Xaa Xaa Xaa Xaa Xaa Xaa Xaa
            755                 760                 765

Xaa Xaa Xaa Thr Xaa Xaa Trp Val Ala Asp Phe Xaa Xaa Xaa Gly
            770                 775                 780

Arg Xaa Xaa Leu Xaa Xaa Xaa Leu Xaa Xaa Xaa Xaa Xaa Xaa Xaa
785                 790                 795                 800

Val Arg Xaa Xaa Xaa Ile Xaa Asn Xaa Xaa Xaa Xaa Xaa Xaa Xaa
                805                 810                 815

Xaa Xaa Xaa Xaa Xaa Xaa Xaa Xaa Xaa Ala Ala Leu Xaa Xaa Xaa
                820                 825                 830

Pro Xaa Xaa Xaa Ala Lys Xaa Xaa Xaa Xaa Lys Xaa Xaa Lys Xaa Xaa
            835                 840                 845

Xaa Xaa Xaa Glu Xaa Xaa Xaa Xaa Xaa Xaa Xaa Xaa Xaa Xaa Xaa
            850                 855                 860

Val Gly Gly Met Asp Xaa Xaa Leu Xaa Xaa Xaa Xaa Xaa Xaa Xaa
865                 870                 875                 880

Xaa Lys Xaa Xaa Xaa Xaa Xaa Xaa Xaa Leu Xaa Xaa Xaa Xaa Xaa
                885                 890                 895

Xaa Xaa Val Leu Xaa Leu Xaa Lys Xaa Gln Arg Xaa Val Ile Xaa Asn
            900                 905                 910

Gly Arg Xaa Ile Gly Pro Leu Xaa Ser Xaa Glu Xaa Phe Xaa Xaa Ala
            915                 920                 925

Asp Phe Xaa Leu Leu Xaa Xaa Xaa Xaa Xaa Xaa Xaa Xaa Xaa Lys
            930                 935                 940

Ile Xaa Xaa Xaa Xaa Xaa Xaa Xaa Xaa Xaa Val Asn Xaa Xaa Xaa
945                 950                 955                 960

Xaa Xaa Xaa Xaa Ser Xaa Xaa Leu Xaa Xaa Leu Xaa Xaa Xaa Xaa
            965                 970                 975

Xaa Xaa Xaa Xaa Xaa Xaa Xaa Xaa Lys Xaa Glu Xaa Xaa Xaa Pro
            980                 985                 990

Xaa Xaa Xaa Xaa Xaa Asp Xaa His Ser Val Xaa Xaa Xaa Thr Leu Xaa
            995                 1000                1005

Xaa Xaa Xaa Xaa Xaa Xaa Xaa Xaa Asp Val Xaa Ala Val Leu Asp
            1010                1015                1020

Pro Leu Xaa Xaa Xaa Ala Gln Lys Leu Xaa Xaa Ile Leu Xaa Xaa Xaa
1025                1030                1035                1040

Xaa Xaa Leu Xaa Asn Xaa Xaa Xaa Xaa Xaa Leu Asn Pro Xaa Xaa
            1045                1050                1055

Xaa Leu Ser Xaa Xaa Pro Leu Lys Arg Phe Tyr Arg Tyr Xaa Xaa
            1060                1065                1070

Xaa Glu Xaa Xaa Phe Asp Ala Xaa Gly Xaa Xaa Xaa Xaa Xaa Xaa
            1075                1080                1085

Xaa Xaa Phe Xaa Xaa Leu Pro Xaa Xaa Pro Leu Leu Thr Xaa Xaa Leu
            1090                1095                1100

Xaa Xaa Pro Xaa Ser Xaa Trp Val Glu Xaa Val Xaa Xaa Xaa Tyr Asp
1105                1110                1115                1120
```

-continued

Leu Asp Asn Ile Lys Leu Glu Xaa Xaa Xaa Xaa Xaa Xaa Xaa Xaa
                    1125                1130                1135

Xaa Val Xaa Ala Glu Phe Xaa Leu Xaa Xaa Leu Leu Leu Xaa Gly Xaa
            1140                1145                1150

Cys Xaa Asp Xaa Xaa Xaa Gly Xaa Pro Pro Arg Gly Leu Gln Leu Xaa
        1155                1160                1165

Leu Gly Thr Xaa Xaa Asn Pro Xaa Xaa Xaa Asp Xaa Thr Ile Val Met
    1170                1175                1180

Ala Asn Leu Gly Tyr Phe Gln Leu Xaa Xaa Xaa Lys Ala Asn Pro Gly
1185                1190                1195                1200

Ala Xaa Trp Leu Xaa Xaa Arg Asp Gly Arg Ser Xaa Xaa Ile Tyr Xaa
        1205                1210                1215

Ile Xaa Ser His Xaa Xaa Gly Thr Xaa Xaa Xaa Xaa Asp Xaa Xaa Xaa
        1220                1225                1230

Xaa Xaa Xaa Xaa Gln Val Xaa Xaa Xaa Ser Phe Xaa Xaa Xaa Xaa Xaa
        1235                1240                1245

Xaa Val Xaa Val Xaa Lys Lys Pro Gly Met Xaa Xaa Xaa Xaa Leu Leu
        1250                1255                1260

Ser Asp Xaa Xaa Xaa Glu Xaa Xaa Xaa Glu Xaa Gly Xaa Xaa Trp Ser
1265                1270                1275                1280

Xaa Xaa Xaa Xaa Phe Xaa Xaa Xaa Xaa Xaa Xaa Xaa Xaa Xaa Xaa Xaa
            1285                1290                1295

Xaa Asp Xaa Xaa Xaa Ile Asn Ile Phe Ser Val Xaa Ala Ser Gly Xaa
        1300                1305                1310

His Leu Tyr Glu Arg Phe Leu Arg Ile Met Xaa Xaa Ser Val Leu Lys
        1315                1320                1325

Xaa Xaa Xaa Thr Lys Xaa Pro Val Lys Phe Trp Phe Leu Lys Asn Xaa
        1330                1335                1340

Tyr Leu Ser Pro Xaa Phe Lys Xaa Xaa Xaa Pro Xaa Xaa Ala Lys Xaa
1345                1350                1355                1360

Tyr Asn Phe Xaa Tyr Glu Leu Ile Xaa Xaa Xaa Tyr Lys Trp Pro Arg
            1365                1370                1375

Trp Leu His Gln Gln Xaa Xaa Xaa Glu Lys Gln Arg Xaa Ile Trp Gly
        1380                1385                1390

Tyr Lys Ile Leu Phe Leu Asp Val Leu Phe Pro Leu Xaa Val Xaa Lys
        1395                1400                1405

Val Ile Phe Val Asp Ala Asp Gln Ile Val Arg Xaa Asp Leu Xaa Glu
        1410                1415                1420

Leu Xaa Asp Phe Asp Xaa Leu Xaa Gly Ala Pro Tyr Gly Tyr Thr Pro
1425                1430                1435                1440

Phe Cys Asp Ser Arg Xaa Glu Met Asp Gly Phe Arg Phe Trp Lys Xaa
                    1445                1450                1455

Gly Tyr Xaa Xaa Trp His Leu Xaa Gly Arg Xaa Xaa Xaa Xaa Tyr His
            1460                1465                1470

Ile Ser Ala Leu Tyr Val Val Asp Leu Xaa Arg Phe Arg Lys Ile Ala
        1475                1480                1485

Ala Gly Asp Arg Leu Arg Gly Gln Tyr Gln Xaa Leu Ser Xaa Asp Pro
    1490                1495                1500

Asn Ser Leu Ser Asn Leu Asp Gln Asp Leu Pro Asn Asn Met Ile His
1505                1510                1515                1520

Gln Val Pro Ile Lys Ser Leu Pro Gln Xaa Xaa Xaa Xaa Trp Leu Trp
        1525                1530                1535

-continued

```
Cys Glu Thr Trp Cys Xaa Asp Xaa Ser Lys Lys Xaa Ala Lys Thr Ile
            1540                1545                1550

Asp Leu Cys Asn Asn Pro Xaa Thr Lys Glu Xaa Lys Leu Xaa Xaa Ala
        1555                1560                1565

Xaa Arg Ile Val Xaa Glu Xaa Trp Asp Tyr Asp Xaa Glu Ile Xaa Xaa
    1570                1575                1580

Leu Xaa Xaa Xaa Xaa Xaa Xaa Xaa Xaa Xaa Xaa Xaa Xaa Xaa Xaa Xaa
1585                1590                1595                1600

Xaa Xaa Xaa Xaa Xaa Xaa Xaa Xaa Xaa Xaa Xaa Xaa Xaa Xaa Xaa Xaa
                1605                1610                1615

Xaa Xaa Xaa Xaa Xaa Xaa His Xaa Glu Leu
            1620                1625
```

<210> SEQ ID NO 20
<211> LENGTH: 115
<212> TYPE: PRT
<213> ORGANISM: Artificial Sequence
<220> FEATURE:
<223> OTHER INFORMATION: UGGT-H. sap

<400> SEQUENCE: 20

```
Pro Leu Ala Val Asp Lys Ile Ile Phe Val Asp Ala Asp Gln Ile Val
1               5                   10                  15

Arg His Asp Leu Lys Glu Leu Arg Asp Phe Asp Leu Asp Gly Ala Pro
            20                  25                  30

Tyr Gly Tyr Thr Pro Phe Cys Asp Ser Arg Arg Glu Met Asp Gly Tyr
        35                  40                  45

Arg Phe Trp Lys Thr Gly Tyr Trp Ala Ser His Leu Leu Arg Arg Lys
    50                  55                  60

Tyr His Ile Ser Ala Leu Tyr Val Val Asp Leu Lys Lys Phe Arg Arg
65                  70                  75                  80

Ile Gly Ala Gly Asp Arg Leu Arg Ser Gln Tyr Gln Ala Leu Ser Gln
                85                  90                  95

Asp Pro Asn Ser Leu Ser Asn Leu Asp Gln Asp Leu Pro Asn Asn Met
            100                 105                 110

Ile His Gln
        115
```

<210> SEQ ID NO 21
<211> LENGTH: 73
<212> TYPE: PRT
<213> ORGANISM: Artificial Sequence
<220> FEATURE:
<223> OTHER INFORMATION: UGGT-A. tha

<400> SEQUENCE: 21

```
Pro Leu Ser Leu Glu Lys Val Ile Phe Val Asp Ala Asp Gln Ile Ile
1               5                   10                  15

Arg Xaa Asp Met Gly Glu Leu Tyr Asp Met Asp Ile Lys Gly Arg Pro
            20                  25                  30

Leu Ala Tyr Thr Pro Phe Cys Asp Asn Asn Arg Xaa Met Asp Gly Tyr
        35                  40                  45

Lys Phe Trp Lys Gln Gly Phe Trp Lys Glu His Leu Arg Gly Arg Pro
    50                  55                  60

Tyr His Ile Gln Cys Ser Ile Arg Cys
65                  70
```

<210> SEQ ID NO 22

-continued

```
<211> LENGTH: 115
<212> TYPE: PRT
<213> ORGANISM: Artificial Sequence
<220> FEATURE:
<223> OTHER INFORMATION: UGGT-O. sat

<400> SEQUENCE: 22
```

Pro Leu Ser Leu Arg Lys Val Ile Phe Val Asp Ala Asp Gln Ile Val
1               5                   10                  15

Arg Ala Asp Met Gly Glu Leu Tyr Asp Met Asn Leu Lys Gly Arg Pro
            20                  25                  30

Leu Ala Tyr Thr Pro Phe Cys Asp Asn Asn Lys Glu Met Asp Gly Tyr
        35                  40                  45

Arg Phe Trp Lys Gln Gly Phe Trp Lys Asp His Leu Arg Gly Arg Pro
    50                  55                  60

Tyr His Ile Ser Ala Leu Tyr Val Val Asp Leu Ala Lys Phe Arg Gln
65                  70                  75                  80

Thr Ala Ser Gly Asp Thr Leu Arg Val Phe Tyr Glu Thr Leu Ser Lys
                85                  90                  95

Asp Pro Asn Ser Leu Ser Asn Leu Asp Gln Asp Leu Pro Asn Tyr Ala
            100                 105                 110

Gln His Thr
        115

```
<210> SEQ ID NO 23
<211> LENGTH: 110
<212> TYPE: PRT
<213> ORGANISM: Artificial Sequence
<220> FEATURE:
<223> OTHER INFORMATION: GALT-E. col

<400> SEQUENCE: 23
```

Ile Asn Lys Ala Pro Lys Val Leu Tyr Leu Asp Ala Asp Ile Ile Cys
1               5                   10                  15

Gln Gly Thr Ile Glu Pro Leu Ile Asn Phe Ser Phe Pro Asp Asp Lys
            20                  25                  30

Val Ala Met Val Val Thr Glu Gly Gln Ala Asp Trp Trp Glu Lys Arg
        35                  40                  45

Ala His Ser Leu Gly Val Ala Gly Ile Ala Lys Gly Tyr Phe Asn Ser
    50                  55                  60

Gly Phe Leu Leu Ile Asn Thr Ala Gln Trp Ala Ala Gln Gln Val Ser
65                  70                  75                  80

Ala Arg Ala Ile Ala Met Leu Asn Glu Pro Glu Ile Ile Lys Lys Ile
                85                  90                  95

Thr His Pro Asp Gln Asp Val Leu Asn Met Leu Leu Ala Asp
            100                 105                 110

```
<210> SEQ ID NO 24
<211> LENGTH: 110
<212> TYPE: PRT
<213> ORGANISM: Artificial Sequence
<220> FEATURE:
<223> OTHER INFORMATION: GALT-S. typ

<400> SEQUENCE: 24
```

Gln Ile Lys Gln Ile Lys Val Leu Tyr Leu Asp Ala Asp Ile Ala Cys
1               5                   10                  15

Lys Gly Ser Ile Gln Glu Leu Ile Asp Leu Asn Phe Ala Glu Asn Glu
            20                  25                  30

```
Ile Ala Ala Val Val Ala Glu Gly Glu Leu Glu Trp Trp Thr Asn Ala
            35                  40                  45

Arg Leu Ser Leu Ala Thr Pro Gly Leu Val Ser Gly Tyr Phe Asn Ala
        50                  55                  60

Gly Phe Ile Leu Ile Xaa Ile Pro Leu Trp Thr Ala Glu Asn Ile Ser
65                  70                  75                  80

Lys Lys Ala Ile Glu Met Leu Lys Asp Pro Glu Val Val Gln Arg Ile
                85                  90                  95

Thr His Leu Asp Gln Asp Val Leu Asn Ile Phe Leu Val Asn
                100                 105                 110
```

<210> SEQ ID NO 25
<211> LENGTH: 106
<212> TYPE: PRT
<213> ORGANISM: Artificial Sequence
<220> FEATURE:
<223> OTHER INFORMATION: GLUT-E. col

<400> SEQUENCE: 25

```
Gly Leu Thr Leu Asp Arg Leu Leu Tyr Leu Asp Ala Asp Val Val Cys
 1               5                  10                  15

Lys Gly Asp Ile Ser Gln Leu Leu His Leu Gly Leu Asn Gly Ala Val
                20                  25                  30

Ala Ala Val Val Lys Asp Val Glu Pro Met Gln Glu Lys Ala Val Ser
            35                  40                  45

Arg Leu Ser Asp Pro Glu Leu Leu Gly Gln Tyr Phe Asn Ser Gly Val
        50                  55                  60

Val Tyr Leu Asp Leu Lys Lys Trp Ala Asp Ala Lys Leu Thr Glu Lys
65                  70                  75                  80

Ala Leu Ser Ile Leu Met Ser Lys Asp Asn Val Tyr Lys Tyr Pro Asp
                85                  90                  95

Gln Asp Val Met Asn Val Leu Leu Lys Gly
                100                 105
```

<210> SEQ ID NO 26
<211> LENGTH: 107
<212> TYPE: PRT
<213> ORGANISM: Artificial Sequence
<220> FEATURE:
<223> OTHER INFORMATION: GLUT-S. typ

<400> SEQUENCE: 26

```
Ser Lys Lys Val Asn Thr Leu Leu Tyr Leu Asp Ala Asp Val Val Cys
 1               5                  10                  15

Lys Gly Ser Leu Ala Asp Leu Leu Gln Leu Asp Leu Thr Glu Lys Ile
                20                  25                  30

Ala Ala Val Val Lys Asp Val Asp Ser Ile Gln Asn Lys Val Asn Glu
            35                  40                  45

Arg Leu Ser Ala Phe Asn Leu Gln Gly Gly Tyr Phe Asn Ser Gly Val
        50                  55                  60

Val Phe Val Asn Leu Lys Leu Trp Lys Glu Asn Ala Leu Thr Lys Lys
65                  70                  75                  80

Ala Phe Leu Leu Leu Ala Gly Lys Glu Ala Asp Ser Phe Lys Tyr Pro
                85                  90                  95

Asp Gln Asp Val Leu Asn Ile Leu Leu Gln Asp
                100                 105
```

<210> SEQ ID NO 27

```
<211> LENGTH: 106
<212> TYPE: PRT
<213> ORGANISM: Artificial Sequence
<220> FEATURE:
<223> OTHER INFORMATION: GLUT-H. inf

<400> SEQUENCE: 27

Ile Lys Asn Ile Glu Lys Ala Ile Tyr Ile Asp Val Asp Thr Leu Thr
 1               5                  10                  15

Asn Ser Ser Leu Gln Glu Leu Trp Asn Ile Asp Ile Thr Asn Tyr Tyr
            20                  25                  30

Leu Ala Ala Cys Arg Asp Thr Phe Ile Asp Val Lys Asn Glu Ala Tyr
        35                  40                  45

Lys Lys Thr Ile Gly Leu Glu Gly Tyr Ser Tyr Phe Asn Ala Gly Ile
 50                  55                  60

Leu Leu Ile Asn Leu Asn Lys Trp Lys Glu Glu Asn Ile Phe Gln Lys
65                  70                  75                  80

Ser Ile Asn Trp Met Asn Lys Tyr Asn Asn Val Met Lys Tyr Gln Asp
                85                  90                  95

Gln Asp Ile Leu Asn Gly Ile Cys Lys Gly
            100                 105

<210> SEQ ID NO 28
<211> LENGTH: 106
<212> TYPE: PRT
<213> ORGANISM: Artificial Sequence
<220> FEATURE:
<223> OTHER INFORMATION: GLYT-N. gon

<400> SEQUENCE: 28

Ile Ala Asp Cys Asp Lys Val Leu Tyr Leu Asp Thr Asp Val Leu Val
 1               5                  10                  15

Arg Asp Gly Leu Lys Pro Leu Trp Asp Thr Asp Leu Gly Gly Asn Trp
            20                  25                  30

Val Gly Ala Cys Ile Asp Leu Phe Val Glu Arg Gln Glu Gly Tyr Lys
        35                  40                  45

Gln Lys Ile Gly Met Ala Asp Gly Glu Tyr Tyr Phe Asn Ala Gly Val
 50                  55                  60

Leu Leu Ile Asn Leu Lys Lys Trp Arg Arg His Asp Ile Phe Lys Met
65                  70                  75                  80

Ser Cys Glu Trp Val Glu Gln Tyr Lys Asp Val Met Gln Tyr Gln Asp
                85                  90                  95

Gln Asp Ile Leu Asn Gly Leu Phe Lys Gly
            100                 105

<210> SEQ ID NO 29
<211> LENGTH: 105
<212> TYPE: PRT
<213> ORGANISM: Artificial Sequence
<220> FEATURE:
<223> OTHER INFORMATION: GSPA-B. sub

<400> SEQUENCE: 29

Asp Glu Ser Ile Lys Arg Met Ile Tyr Ile Asp Cys Asp Ala Leu Val
 1               5                  10                  15

Leu Glu Asp Ile Ser Lys Leu Trp Asp Leu Asp Ile Ala Pro Tyr Thr
            20                  25                  30

Val Ala Ala Val Glu Asp Ala Gly Gln His Glu Arg Leu Lys Glu Met
        35                  40                  45
```

```
Asn Val Thr Asp Thr Gly Lys Tyr Phe Asn Ser Gly Ile Met Ile Ile
            50                  55                  60

Asp Phe Glu Ser Trp Arg Lys Gln Asn Ile Thr Glu Lys Val Ile Asn
 65                  70                  75                  80

Phe Ile Asn Glu His Pro Asp Glu Asp Phe Leu Val Leu His Asp Gln
                     85                  90                  95

Asp Ala Leu Asn Ala Ile Leu Tyr Asp
                100                 105

<210> SEQ ID NO 30
<211> LENGTH: 121
<212> TYPE: PRT
<213> ORGANISM: Artificial Sequence
<220> FEATURE:
<223> OTHER INFORMATION: Q48480-K. p

<400> SEQUENCE: 30

Phe Arg Arg Tyr Asp Lys Val Val Phe Ile Asp Ser Asp Thr Val Val
  1               5                  10                  15

Lys Ala Asp Leu Gly Glu Leu Leu Asp Val Pro Leu Gly Asn Asn Leu
                 20                  25                  30

Val Ala Ala Val Lys Asp Ile Val Met Glu Gly Phe Val Lys Phe Ser
                 35                  40                  45

Ala Met Ser Ala Ser Asp Asp Gly Val Met Pro Ala Gly Glu Tyr Leu
 50                  55                  60

Gln Lys Thr Leu Asn Asn Asn Pro Asp Glu Tyr Phe Gln Ala Gly
 65                  70                  75                  80

Ile Ile Val Phe Asn Val Lys Gln Met Val Glu Glu Asn Thr Phe Ala
                 85                  90                  95

Glu Leu Met Arg Val Leu Lys Ala Lys Lys Tyr Trp Phe Leu Asp Gln
                100                 105                 110

Asp Ile Met Asn Lys Val Phe Tyr Ser
                115                 120

<210> SEQ ID NO 31
<211> LENGTH: 82
<212> TYPE: PRT
<213> ORGANISM: Artificial Sequence
<220> FEATURE:
<223> OTHER INFORMATION: GLYC-H. sap

<400> SEQUENCE: 31

Leu Thr Gln Tyr Ser Lys Cys Val Phe Met Asp Ala Asp Thr Leu Val
  1               5                  10                  15

Leu Ala Asn Ile Asp Asp Leu Phe Asp Arg Glu Glu Leu Ser Ala Ala
                 20                  25                  30

Pro Asp Pro Gly Trp Pro Asp Cys Phe Asn Ser Gly Val Phe Val Tyr
                 35                  40                  45

Gln Pro Ser Val Glu Thr Tyr Asn Gln Leu Leu His Leu Ala Ser Glu
 50                  55                  60

Gln Gly Ser Phe Asp Gly Gly Asp Gln Gly Ile Leu Asn Thr Phe Phe
 65                  70                  75                  80

Ser Ser

<210> SEQ ID NO 32
<211> LENGTH: 82
<212> TYPE: PRT
<213> ORGANISM: GLYC-O. cunArtificial Sequence
<220> FEATURE:
```

```
<223> OTHER INFORMATION: GLYC-O. cun

<400> SEQUENCE: 32

Leu Thr Gln Tyr Ser Lys Cys Val Phe Met Asp Ala Asp Thr Leu Val
 1               5                  10                  15

Leu Ala Asn Ile Asp Asp Leu Phe Glu Arg Glu Leu Ser Ala Ala
             20                  25                  30

Pro Asp Pro Gly Trp Pro Asp Cys Phe Asn Ser Gly Val Phe Val Tyr
             35                  40                  45

Gln Pro Ser Val Glu Thr Tyr Asn Gln Leu Leu His Val Ala Ser Glu
     50                  55                  60

Gln Gly Ser Phe Asp Gly Gly Asp Gln Gly Leu Leu Asn Thr Phe Phe
65                  70                  75                  80

Asn Ser

<210> SEQ ID NO 33
<211> LENGTH: 82
<212> TYPE: PRT
<213> ORGANISM: Artificial Sequence
<220> FEATURE:
<223> OTHER INFORMATION: GLYC-C. ele

<400> SEQUENCE: 33

Leu Thr Gln Tyr Thr Lys Cys Val Phe Leu Asp Ala Asp Thr Leu Val
 1               5                  10                  15

Leu Arg Asn Ala Asp Glu Leu Phe Thr Arg Pro Asp Phe Ser Ala Ala
             20                  25                  30

Ser Asp Ile Gly Trp Pro Asp Ser Phe Asn Ser Gly Val Phe Val Tyr
             35                  40                  45

Val Pro Asn Asn Glu Thr Tyr Arg Gln Leu Val Asp Phe Ala Val Thr
     50                  55                  60

His Gly Ser Tyr Asp Gly Gly Asp Gln Gly Leu Leu Asn Asp Phe Phe
65                  70                  75                  80

Ser Asn

<210> SEQ ID NO 34
<211> LENGTH: 117
<212> TYPE: PRT
<213> ORGANISM: Artificial Sequence
<220> FEATURE:
<223> OTHER INFORMATION: WSIP-O. sat

<400> SEQUENCE: 34

Phe Val Glu Tyr Glu Arg Met Val Tyr Leu Asp Ala Asp Ile Gln Val
 1               5                  10                  15

Phe Asp Asn Ile Asp His Leu Phe Asp Leu Asp Lys Gly Ala Phe Tyr
             20                  25                  30

Ala Val Lys Asp Cys Phe Cys Glu Lys Thr Trp Ser His Thr Pro Gln
             35                  40                  45

Tyr Asp Ile Gly Tyr Cys Gln Gln Arg Pro Asp Glu Val Ala Trp Pro
     50                  55                  60

Glu Arg Glu Leu Gly Pro Pro Pro Leu Tyr Phe Asn Ala Gly Met
65                  70                  75                  80

Phe Val His Glu Pro Gly Leu Gly Thr Ala Lys Asp Leu Leu Asp Ala
             85                  90                  95

Leu Val Val Thr Pro Pro Thr Pro Phe Ala Glu Gln Asp Phe Leu Asn
             100                 105                 110
```

```
Met Phe Phe Arg Glu
        115

<210> SEQ ID NO 35
<211> LENGTH: 87
<212> TYPE: PRT
<213> ORGANISM: Artificial Sequence
<220> FEATURE:
<223> OTHER INFORMATION: Q12096-S. c

<400> SEQUENCE: 35

Gln Thr Glu Phe Asp Arg Val Ile Tyr Leu Asp Asn Asp Ala Ile Leu
 1               5                  10                  15

Arg Ser Ser Leu Asp Glu Leu Phe Phe Leu Pro Asn Tyr Ile Lys Phe
            20                  25                  30

Ala Ala Pro Leu Thr Tyr Trp Phe Leu Ser Asn Ser Asp Leu Glu Lys
        35                  40                  45

Ser Tyr His Glu Thr Arg His Arg Glu Lys Gln Pro Ile Asn Leu Gln
    50                  55                  60

Ser Tyr Thr Lys Val Leu Thr Lys Arg Ile Gly Lys Gly Gln Met Ile
65                  70                  75                  80

Tyr Asn His Leu Pro Ser Leu
                85
```